(12) United States Patent
Raum et al.

(10) Patent No.: US 8,247,194 B2
(45) Date of Patent: Aug. 21, 2012

(54) PREPARATION OF SCFV ANTIBODY FRAGMENTS

(75) Inventors: Tobias Raum, Munich (DE); Julia Henckel, Munich (DE); Eva Krinner, Munich (DE); Silke Mittelstrass, Munich (DE); Andreas Wolf, Munich (DE)

(73) Assignee: Micromet AG, Munich (DE)

( * ) Notice: Subject to any disclaimer, the term of this patent is extended or adjusted under 35 U.S.C. 154(b) by 511 days.

(21) Appl. No.: 11/568,685

(22) PCT Filed: May 4, 2005

(86) PCT No.: PCT/EP2005/004893
§ 371 (c)(1),
(2), (4) Date: Dec. 3, 2007

(87) PCT Pub. No.: WO2005/105844
PCT Pub. Date: Nov. 10, 2005

(65) Prior Publication Data
US 2008/0193978 A1 Aug. 14, 2008

(30) Foreign Application Priority Data

May 5, 2004 (EP) .................... 04010702

(51) Int. Cl.
*C12P 21/04* (2006.01)
(52) U.S. Cl. .................................... 435/69.6
(58) Field of Classification Search .............. 435/69.6
See application file for complete search history.

(56) References Cited

U.S. PATENT DOCUMENTS 6,265,150 B1  7/2001  Terstappen et al. .............. 435/5

OTHER PUBLICATIONS

MacCallum et al. (J. Mol. Biol. (1996) 262:732-745).*
De Pascalis et al. (The Journal of Immunology (2002) 169, 3076-3084).*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. (J. Mol. Bio. (1999) 293, 865-881).*
Wu et al. (J. Mol. Biol. (1999) 294, 151-162).*
Kumar et al. (J. Biol. Chem. 275:35129-35136 (2000)).*
Smith-Gill et al. (J. Immunol. 139:4135-4144 (1987)).*
Song et al. (Biochem Biophys Res Comm 268:390-394 (2000)).*
Arndt et al. (2001) J Mol Biol 312: 221-228.*
Clackson et al., "Making Antibody Fragment Using Phage Display Libraries," *Nature*, 352:624-628, 1991.
Holt et al., "Domain Antibodies: Proteins For Therapy," *Trends in Biotechnology*, 21(11):484-490, 2003.
Lee et al., "Bivalent Antibody Phage Display Mimics Natural Immunoglobulin," *Journal of Immunological Methods*, 284:119-132, 2004.
Neri et al., "Targeting by Affinity-Matured Recombinant Antibody Fragments of an Angiogenesis Associated Fibronectin Isoform," *Nature Biotechnology*, 15(12):1271-1275, 1997.
Pack et al., "Improved Bivalent Miniantibodies, with Identical Avidity as Whole Antibodies, Produced by High Cell Density Fermentation of *Escherichia coli*," *BIO/Technology*, 11(11):1271-1277, 1993.
Pack et al., "Miniantibodies: Use of Amphipathic Helices to Produce Functional, Flexibly Linked Dimeric FV Fragments with High Avidity in *Escherichia coli*," *Biochemistry*, 31(6):1579-1584, 1992.
Pack et al., "Tetravalent Miniantibodies with High Avidity Assembling in *Escherichia coli*," *Journal of Molecular Biology*, 246(1):28-34, 1995.
Sblattero et al., "Exploiting Recombination in Single Bacteria to Make Large Phage Antibody Libraries," *Nature Biotechnology*, 18(1):75-80, 2000.

* cited by examiner

*Primary Examiner* — Lynn Bristol
(74) *Attorney, Agent, or Firm* — Fulbright & Jaworski

(57) ABSTRACT

The invention relates to methods of preparing antibody fragments. The invention further relates to antibody fragments prepared by said methods. The invention further relates to antibody variable regions comprised in antibody fragments producible by said methods.

15 Claims, 38 Drawing Sheets

Fig. 11

B32oN-10

Figure 1:
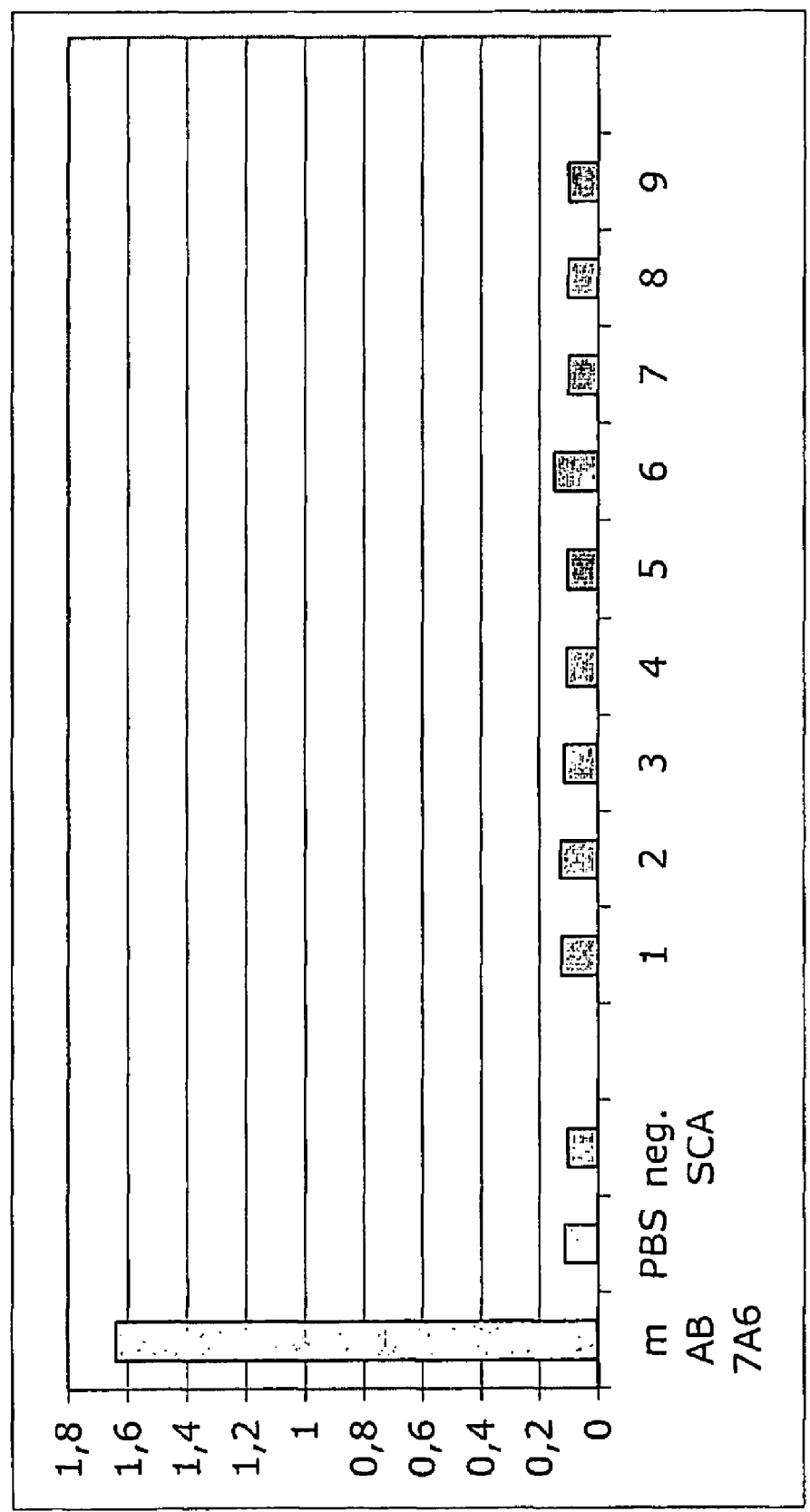

```
      E   L   Q   L   V   E   Q   S   G   A   A   L   V   K   P   G   D   S   V   K
  1   GAGCTGCAGCTGGTC  GAGCAGTCTGGAGCT  GCACTGGTGAAGCCT  GGGGACTCTGTGAAG
      CTCGACGTCGACCAG  CTCGTCAGACCTCGA  CGTGACCACTTCGGA  CCCCTGAGACACTTC

M   S   C   K   A   S   G   Y   P   F   T   D   Y   I   V   H   W   V   K   Q
 61   ATGTCTTGCAAAGCT  TCTGGTTATCCATTC  ACTGACTATATTGTA  CACTGGGTGAAGCAG
      TACAGAACGTTTCGA  AGACCAATAGGTAAG  TGACTGATATAACAT  GTGACCCACTTCGTC

S   H   G   K   S   L   D   W   I   G   Y   I   N   P   Y   S   G   D   T   K
121   AGTCATGGAAAGAGC  CTTGACTGGATTGGT  TATATTAATCCTTAC  AGTGGTGATACTAAG
      TCAGTACCTTTCTCG  GAACTGACCTAACCA  ATATAATTAGGAATG  TCACCACTATGATTC

F   N   E   K   F   K   S   K   A   T   L   T   V   D   K   S   S   S   T   A
181   TTCAATGAAAAGTTC  AAGAGTAAGGCCACG  TTGACTGTTGACAAG  TCCAGCAGCACAGCC
      AAGTTACTTTTCAAG  TTCTCATTCCGGTGC  AACTGACAACTGTTC  AGGTCGTCGTGTCGG

Y   M   E   F   S   R   L   T   S   E   D   S   A   I   Y   Y   C   A   R   S
241   TATATGGAGTTTAGC  CGATTGACATCTGAG  GATTCTGCAATCTAT  TACTGTGCAAGATCG
      ATATACCTCAAATCG  GCTAACTGTAGACTC  CTAAGACGTTAGATA  ATGACACGTTCTAGC

G   L   I   A   V   Y   F   D   Y   W   G   Q   G   T   T   V   T   V   S   S
301   GGTCTGATAGCAGTC  TACTTTGATTACTGG  GGCCAAGGGACCACG  GTCACCGTCTCCTCA
      CCAGACTATCGTCAG  ATGAAACTAATGACC  CCGGTTCCCTGGTGC  CAGTGGCAGAGGAGT

G   G   G   S   G   G   G   S   G   G   G   S   E   L   Q   M   T
361   GGTGGTGGTGGTTCT  GGCGGCGGCGGCTCC  GGTGGTGGTGGTTCT  GAGCTCCAGATGACC
      CCACCACCACCAAGA  CCGCCGCCGCCGAGG  CCACCACCACCAAGA  CTCGAGGTCTACTGG

Q   S   P   S   S   L   S   A   S   V   G   D   R   V   T   I   T   C   R   T
421   CAGTCTCCATCCTCC  CTGTCTGCATCTGTA  GGAGACAGAGTCACC  ATCACTTGCCGGACA
      GTCAGAGGTAGGAGG  GACAGACGTAGACAT  CCTCTGTCTCAGTGG  TAGTGAACGGCCTGT

S   Q   T   I   S   S   L   L   N   W   Y   Q   Q   K   P   G   K   A   P   K
481   AGTCAGACCATTAGC  AGTCTTTTAAATTGG  TATCAGCAGAAACCA  GGGAAAGCCCCTAAG
      TCAGTCTGGTAATCG  TCAGAAAATTTAACC  ATAGTCGTCTTTGGT  CCCTTTCGGGGATTC

L   L   I   Y   A   A   S   N   L   Q   S   G   V   P   S   R   F   S   G   S
541   CTCCTGATCTATGCT  GCATCCAATTTGCAA  AGTGGGGTCCCATCA  AGGTTCAGTGGCAGT
      GAGGACTAGATACGA  CGTAGGTTAAACGTT  TCACCCCAGGGTAGT  TCCAAGTCACCGTCA

G   S   G   T   D   F   T   L   T   I   S   G   L   Q   P   E   D   F   S   T
601   GGATCTGGGACAGAT  TTCACTCTCACCATC  AGCGGTCTGCAACCT  GAAGATTTTTCAACT
      CCTAGACCCTGTCTA  AAGTGAGAGTGGTAG  TCGCCAGACGTTGGA  CTTCTAAAAAGTTGA

Y   F   C   Q   Q   S   Y   S   F   P   R   T   F   G   Q   G   T   K   V   D
661   TACTTCTGTCAACAG  AGTTACAGTTTCCCT  CGAACGTTCGGCCAA  GGGACCAAAGTGGAT
      ATGAAGACAGTTGTC  TCAATGTCAAAGGGA  GCTTGCAAGCCGGTT  CCCTGGTTTCACCTA

I   K
721   ATCAAA
      TAGTTT
```

Fig. 12

B32oN-33

```
           E   L   Q   L   V       E   Q   S   G   A       A   L   V   K   P       G   D   S   V   K
  1   GAGCTGCAGCTGGTC  GAGCAGTCTGGAGCT  GCACTGGTGAAGCCT  GGGGACTCTGTGAAG
      CTCGACGTCGACCAG  CTCGTCAGACCTCGA  CGTGACCACTTCGGA  CCCCTGAGACACTTC

M   S   C   K   A       S   G   Y   P   F       T   D   Y   I   V       H   W   V   K   Q
 61   ATGTCTTGCAAAGCT  TCTGGTTATCCATTC  ACTGACTATATTGTA  CACTGGGTGAAGCAG
      TACAGAACGTTTCGA  AGACCAATAGGTAAG  TGACTGATATAACAT  GTGACCCACTTCGTC

S   H   G   K   S       L   D   W   I   G       Y   I   N   P   Y       S   G   D   T   K
121   AGTCATGGAAAGAGC  CTTGACTGGATTGGT  TATATTAATCCTTAC  AGTGGTGATACTAAG
      TCAGTACCTTTCTCG  GAACTGACCTAACCA  ATATAATTAGGAATG  TCACCACTATGATTC

F   N   E   K   F       K   S   K   A   T       L   T   V   D   K       S   S   S   T   A
181   TTCAATGAAAAGTTC  AAGAGTAAGGCCACG  TTGACTGTTGACAAG  TCCAGCAGCACAGCC
      AAGTTACTTTTCAAG  TTCTCATTCCGGTGC  AACTGACAACTGTTC  AGGTCGTCGTGTCGG

Y   M   E   F   S       R   L   T   S   E       D   S   A   I   Y       Y   C   A   R   S
241   TATATGGAGTTTAGC  CGATTGACATCTGAG  GATTCTGCAATCTAT  TACTGTGCAAGATCG
      ATATACCTCAAATCG  GCTAACTGTAGACTC  CTAAGACGTTAGATA  ATGACACGTTCTAGC

G   L   I   A   V       Y   F   D   Y   W       G   Q   G   T   T       V   T   V   S   S
301   GGTCTGATAGCAGTC  TACTTTGATTACTGG  GGCCAAGGGACCACG  GTCACCGTCTCCTCA
      CCAGACTATCGTCAG  ATGAAACTAATGACC  CCGGTTCCCTGGTGC  CAGTGGCAGAGGAGT

G   G   G   G   S       G   G   G   G   S       G   G   G   G   S       E   L   V   M   T
361   GGTGGTGGTGGTTCT  GGCGGCGGCGGCTCC  GGTGGTGGTGGTTCT  GAGCTCGTGATGACG
      CCACCACCACCAAGA  CCGCCGCCGCCGAGG  CCACCACCACCAAGA  CTCGAGCACTACTGC

Q   S   P   A   T       L   S   L   S   P       G   E   R   A   T       L   S   C   R   A
421   CAGTCTCCAGCCACC  CTGTCTTTGTCTCCA  GGGGAAAGAGCCACC  CTCTCCTGCAGGGCC
      GTCAGAGGTCGGTGG  GACAGAAACAGAGGT  CCCCTTTCTCGGTGG  GAGAGGACGTCCCGG

S   Q   S   V   R       T   Y   L   A   W       Y   Q   Q   K   P       G   Q   A   P   R
481   AGTCAGAGTGTTAGG  ACCTACTTAGCCTGG  TACCAACAGAAACCT  GGCCAGGCTCCCAGG
      TCAGTCTCACAATCC  TGGATGAATCGGACC  ATGGTTGTCTTTGGA  CCGGTCCGAGGGTCC

L   L   I   Y   A       A   S   H   R   A       T   G   I   P   A       R   F   S   G   S
541   CTCCTCATCTATGCT  GCATCCCACAGGGCC  ACTGGCATCCCAGCC  AGGTTCAGTGGCAGT
      GAGGAGTAGATACGA  CGTAGGGTGTCCCGG  TGACCGTAGGGTCGG  TCCAAGTCACCGTCA

G   S   G   T   D       F   T   L   T   I       S   R   L   E   P       E   D   F   A   V
601   GGGTCTGGGACAGAC  TTCACTCTCACCATC  AGCAGACTGGAGCCT  GAAGATTTTGCAGTG
      CCCAGACCCTGTCTG  AAGTGAGAGTGGTAG  TCGTCTGACCTCGGA  CTTCTAAAACGTCAC

Y   Y   C   Q   Q       Y   G   S   S   P       P   T   F   G   Q       G   T   K   V   E
661   TATTACTGTCAGCAG  TATGGTAGCTCACCT  CCGACGTTCGGCCAA  GGGACCAAGGTAGAG
      ATAATGACAGTCGTC  ATACCATCGAGTGGA  GGCTGCAAGCCGGTT  CCCTGGTTCCATCTC

I   K
721   ATCAAA
      TAGTTT
```

Fig. 13

B32oN-44

```
          E   L   Q   L   V     E   Q   S   G   A     A   L   V   K   P     G   D   S   V   K
   1    GAGCTGCAGCTGGTC  GAGCAGTCTGGAGCT  GCACTGGTGAAGCCT  GGGGACTCTGTGAAG
        CTCGACGTCGACCAG  CTCGTCAGACCTCGA  CGTGACCACTTCGGA  CCCCTGAGACACTTC

M   S   C   K   A     S   G   Y   P   F     T   D   Y   I   V     H   W   V   K   Q
  61    ATGTCTTGCAAAGCT  TCTGGTTATCCATTC  ACTGACTATATTGTA  CACTGGGTGAAGCAG
        TACAGAACGTTTCGA  AGACCAATAGGTAAG  TGACTGATATAACAT  GTGACCCACTTCGTC

S   H   G   K   S     L   D   W   I   G     Y   I   N   P   Y     S   G   D   T   K
 121    AGTCATGGAAAGAGC  CTTGACTGGATTGGT  TATATTAATCCTTAC  AGTGGTGATACTAAG
        TCAGTACCTTTCTCG  GAACTGACCTAACCA  ATATAATTAGGAATG  TCACCACTATGATTC

F   N   E   K   F     K   S   K   A   T     L   T   V   D   K     S   S   S   T   A
 181    TTCAATGAAAAGTTC  AAGAGTAAGGCCACG  TTGACTGTTGACAAG  TCCAGCAGCACAGCC
        AAGTTACTTTTCAAG  TTCTCATTCCGGTGC  AACTGACAACTGTTC  AGGTCGTCGTGTCGG

Y   M   E   F   S     R   L   T   S   E     D   S   A   I   Y     Y   C   A   R   S
 241    TATATGGAGTTTAGC  CGATTGACATCTGAG  GATTCTGCAATCTAT  TACTGTGCAAGATCG
        ATATACCTCAAATCG  GCTAACTGTAGACTC  CTAAGACGTTAGATA  ATGACACGTTCTAGC

G   L   I   A   V     Y   F   D   Y   W     G   Q   G   T   T     V   T   V   S   S
 301    GGTCTGATAGCAGTC  TACTTTGATTACTGG  GGCCAAGGGACCACG  GTCACCGTCTCCTCA
        CCAGACTATCGTCAG  ATGAAACTAATGACC  CCGGTTCCCTGGTGC  CAGTGGCAGAGGAGT

G   G   G   G   S     G   G   G   G   S     G   G   G   G   S     E   L   V   L   T
 361    GGTGGTGGTGGTTCT  GGCGGCGGCGGCTCC  GGTGGTGGTGGTTCT  GAGCTCGTGCTGACT
        CCACCACCACCAAGA  CCGCCGCCGCCGAGG  CCACCACCACCAAGA  CTCGAGCACGACTGA

Q   S   P   D   F     Q   S   V   T   P     K   E   K   V   T     I   T   C   R   A
 421    CAGTCTCCGGACTTT  CAGTCTGTGACTCCA  AAGGAGAAAGTCACC  ATCACCTGCCGGGCC
        GTCAGAGGCCTGAAA  GTCAGACACTGAGGT  TTCCTCTTTCAGTGG  TAGTGGACGGCCCGG

S   Q   S   I   G     S   S   L   H   W     Y   Q   Q   K   P     D   Q   P   P   K
 481    AGTCAGAGCATTGGT  AGTAGCTTACACTGG  TACCAGCAGAAACCA  GATCAGCCTCCAAAG
        TCAGTCTCGTAACCA  TCATCGAATGTGACC  ATGGTCGTCTTTGGT  CTAGTCGGAGGTTTC

L   L   I   K   F     A   S   Q   S   I     S   R   V   P   S     R   F   S   G   T
 541    CTCCTCATCAAATTT  GCTTCCCAGTCCATC  TCAAGGGTCCCCTCG  AGGTTCAGTGGCACT
        GAGGAGTAGTTTAAA  CGAAGGGTCAGGTAG  AGTTCCCAGGGGAGC  TCCAAGTCACCGTGA

G   S   G   T   D     F   T   L   T   I     N   S   L   E   A     E   D   A   A   T
 601    GGATCTGGGACAGAT  TTCACCCTCACCATC  AATAGCCTGGAAGCT  GAAGATGCTGCAACG
        CCTAGACCCTGTCTA  AAGTGGGAGTGGTAG  TTATCGGACCTTCGA  CTTCTACGACGTTGC

Y   Y   C   Q   Q     S   F   S   F   P     Y   T   F   G   Q     G   T   K   L   E
 661    TATTACTGTCAGCAG  AGCTTTAGTTTCCCG  TACACTTTTGGCCAG  GGGACCAAGCTGGAG
        ATAATGACAGTCGTC  TCGAAATCAAAGGGC  ATGTGAAAACCGGTC  CCCTGGTTCGACCTC

I   K
 721    ATCAAA
        TAGTTT
```

Fig. 14

B32oN-45

```
              E   L   Q   L   V       E   Q   S   G   A       A   L   V   K   P       G   D   S   V   K
  1   GAGCTGCAGCTGGTC  GAGCAGTCTGGAGCT  GCACTGGTGAAGCCT  GGGGACTCTGTGAAG
      CTCGACGTCGACCAG  CTCGTCAGACCTCGA  CGTGACCACTTCGGA  CCCCTGAGACACTTC

M   S   C   K   A       S   G   Y   P   F       T  |D   Y   I   V       H| W   V   K   Q
 61   ATGTCTTGCAAAGCT  TCTGGTTATCCATTC  ACTGACTATATTGTA  CACTGGGTGAAGCAG
      TACAGAACGTTTCGA  AGACCAATAGGTAAG  TGACTGATATAACAT  GTGACCCACTTCGTC

S   H   G   K   S       L   D   W   I   G      |Y   I   N   P   Y       S   G   D   T   K
121   AGTCATGGAAAGAGC  CTTGACTGGATTGGT  TATATTAATCCTTAC  AGTGGTGATACTAAG
      TCAGTACCTTTCTCG  GAACTGACCTAACCA  ATATAATTAGGAATG  TCACCACTATGATTC

F   N   E   K   F       K   S| K   A   T       L   T   V   D   K       S   S   S   T   A
181   TTCAATGAAAAGTTC  AAGAGTAAGGCCACG  TTGACTGTTGACAAG  TCCAGCAGCACAGCC
      AAGTTACTTTTCAAG  TTCTCATTCCGGTGC  AACTGACAACTGTTC  AGGTCGTCGTGTCGG

Y   M   E   F   S       R   L   T   S   E       D   S   A   I   Y       Y   C   A   R  |S
241   TATATGGAGTTTAGC  CGATTGACATCTGAG  GATTCTGCAATCTAT  TACTGTGCAAGATCG
      ATATACCTCAAATCG  GCTAACTGTAGACTC  CTAAGACGTTAGATA  ATGACACGTTCTAGC

G   L   I   A   V       Y   F   D   Y| W   G   Q   G   T   T       V   T   V   S   S
301   GGTCTGATAGCAGTC  TACTTTGATTACTGG  GGCCAAGGGACCACG  GTCACCGTCTCCTCA
      CCAGACTATCGTCAG  ATGAAACTAATGACC  CCGGTTCCCTGGTGC  CAGTGGCAGAGGAGT

G   G   G   S       G   G   G   G   S       G   G   G   S       E   L   V   M   T
361   GGTGGTGGTGGTTCT  GGCGGCGGCGGCTCC  GGTGGTGGTGGTTCT  GAGCTCGTGATGACC
      CCACCACCACCAAGA  CCGCCGCCGCCGAGG  CCACCACCACCAAGA  CTCGAGCACTACTGG

Q   S   P   S   S       V   S   A   S   V       G   D   R   V   T       I   A   C  |R   A
421   CAGTCTCCATCTTCC  GTGTCTGCATCTGTA  GGAGACAGAGTCACC  ATCGCTTGTCGGGCG
      GTCAGAGGTAGAAGG  CACAGACGTAGACAT  CCTCTGTCTCAGTGG  TAGCGAACAGCCCGC

S   Q   N   I   R       N   I   L   N| W   Y   Q   Q   R   P       G   K   A   P   Q
481   AGTCAGAACATTAGA  AACATTTTAAATTGG  TATCAACAGAGACCA  GGGAAGGCCCCTCAA
      TCAGTCTTGTAATCT  TTGTAAAATTTAACC  ATAGTTGTCTCTGGT  CCCTTCCGGGGAGTT

L   L   I   Y  |A   A   S   N   L   Q       S| G   V   P   S       R   F   S   G   S
541   CTCCTGATCTATGCT  GCCTCCAATTTACAA  AGTGGCGTCCCATCA  AGGTTCAGTGGCAGT
      GAGGACTAGATACGA  CGGAGGTTAAATGTT  TCACCGCAGGGTAGT  TCCAAGTCACCGTCA

G   S   G   T   D       F   T   L   T   I       N   S   L   Q   P       E   D   F   A   T
601   GGATCTGGGACAGAT  TTCACTCTCACCATC  AACAGTCTGCAACCT  GAAGATTTTGCAACT
      CCTAGACCCTGTCTA  AAGTGAGAGTGGTAG  TTGTCAGACGTTGGA  CTTCTAAAACGTTGA

Y   Y   C  |Q   Q       S   Y   S   M   P       R   T| F   G   G       G   T   K   V   E
661   TACTACTGTCAACAG  AGTTACAGTATGCCT  CGAACTTTCGGCGGA  GGGACCAAGGTGGAA
      ATGATGACAGTTGTC  TCAATGTCATACGGA  GCTTGAAAGCCGCCT  CCCTGGTTCCACCTT

I   K
721   ATCAAA
      TAGTTT
```

Fig. 15

B32oN-48

```
          E   L   Q   L   V    E   Q   S   G   A    A   L   V   K   P    G   D   S   V   K
  1   GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

M   S   C   K   A    S   G   Y   P   F    T   D   Y   I   V    H   W   V   K   Q
 61   ATGTCTTGCAAAGCT TCTGGTTATCCATTC ACTGACTATATTGTA CACTGGGTGAAGCAG
      TACAGAACGTTTCGA AGACCAATAGGTAAG TGACTGATATAACAT GTGACCCACTTCGTC

S   H   G   K   S    L   D   W   I   G    Y   I   N   P   Y    S   G   D   T   K
121   AGTCATGGAAAGAGC CTTGACTGGATTGGT TATATTAATCCTTAC AGTGGTGATACTAAG
      TCAGTACCTTTCTCG GAACTGACCTAACCA ATATAATTAGGAATG TCACCACTATGATTC

F   N   E   K   F    K   S   K   A   T    L   T   V   D   K    S   S   S   T   A
181   TTCAATGAAAAGTTC AAGAGTAAGGCCACG TTGACTGTTGACAAG TCCAGCAGCACAGCC
      AAGTTACTTTTCAAG TTCTCATTCCGGTGC AACTGACAACTGTTC AGGTCGTCGTGTCGG

Y   M   E   F   S    R   L   T   S   E    D   S   A   I   Y    Y   C   A   R   S
241   TATATGGAGTTTAGC CGATTGACATCTGAG GATTCTGCAATCTAT TACTGTGCAAGATCG
      ATATACCTCAAATCG GCTAACTGTAGACTC CTAAGACGTTAGATA ATGACACGTTCTAGC

G   L   I   A   V    Y   F   D   Y   W    G   Q   G   T   T    V   T   V   S   S
301   GGTCTGATAGCAGTC TACTTTGATTACTGG GGCCAAGGGACCACG GTCACCGTCTCCTCA
      CCAGACTATCGTCAG ATGAAACTAATGACC CCGGTTCCCTGGTGC CAGTGGCAGAGGAGT

G   G   G   G   S    G   G   G   G   S    G   G   G   G   S    E   L   V   L   T
361   GGTGGTGGTGGTTCT GGCGGCGGCGGCTCC GGTGGTGGTGGTTCT GAGCTCGTGCTGACT
      CCACCACCACCAAGA CCGCCGCCGCCGAGG CCACCACCACCAAGA CTCGAGCACGACTGA

Q   S   P   G   F    Q   S   V   T   P    K   E   K   V   T    I   T   C   R   A
421   CAGTCTCCAGGCTTT CAGTCTGTGACTCCA AAGGAGAAAGTCACC ATCACCTGCCGGGCC
      GTCAGAGGTCCGAAA GTCAGACACTGAGGT TTCCTCTTTCAGTGG TAGTGGACGGCCCGG

S   Q   S   I   G    S   S   L   H   W    Y   Q   Q   K   P    D   Q   P   P   K
481   AGTCAGAGCATTGGT AGTAGCTTACACTGG TACCAGCAGAAACCA GATCAGCCTCCAAAG
      TCAGTCTCGTAACCA TCATCGAATGTGACC ATGGTCGTCTTTGGT CTAGTCGGAGGTTTC

L   L   I   K   P    A   S   Q   S   I    S   G   V   P   S    R   F   S   G   S
541   CTCCTCATCAAATTT GCTTCCCAGTCCATC TCAGGGGTCCCCTCG AGGTTCAGTGGCAGT
      GAGGAGTAGTTTAAA CGAAGGGTCAGGTAG AGTCCCCAGGGGAGC TCCAAGTCACCGTCA

G   S   G   T   N    F   T   L   T   I    N   S   L   E   A    E   D   A   A   T
601   GGATCTGGGACAAAT TTCACCCTCACCATC AATAGCCTGGAAGCT GAAGATGCTGCAACC
      CCTAGACCCTGTTTA AAGTGGGAGTGGTAG TTATCGGACCTTCGA CTTCTACGACGTTGG

Y   Y   C   Q   Q    S   S   T   L   P    P   T   F   G   Q    G   T   K   V   E
661   TATTACTGTCAGCAG AGTAGTACTTTACCT CCCACTTTTGGCCAG GGGACCAAGGTGGAG
      ATAATGACAGTCGTC TCATCATGAAATGGA GGGTGAAAACCGGTC CCCTGGTTCCACCTC

I   K
721   ATCAAA
      TAGTTT
```

Fig. 16

B32oN-49

```
            E  L  Q  L  V     E  Q  S  G  A     A  L  V  K  P     G  D  S  V  K
  1   GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

M  S  C  K  A     S  G  Y  P  F     T  D  Y  I  V     H  W  V  K  Q
  61  ATGTCTTGCAAAGCT TCTGGTTATCCATTC ACTGACTATATTGTA CACTGGGTGAAGCAG
      TACAGAACGTTTCGA AGACCAATAGGTAAG TGACTGATATAACAT GTGACCCACTTCGTC

S  H  G  K  S     L  D  W  I  G     Y  I  N  P  Y     S  G  D  T  K
 121  AGTCATGGAAAGAGC CTTGACTGGATTGGT TATATTAATCCTTAC AGTGGTGATACTAAG
      TCAGTACCTTTCTCG GAACTGACCTAACCA ATATAATTAGGAATG TCACCACTATGATTC

F  N  E  K  F     K  S  K  A  T     L  T  V  D  K     S  S  S  T  A
 181  TTCAATGAAAAGTTC AAGAGTAAGGCCACG TTGACTGTTGACAAG TCCAGCAGCACAGCC
      AAGTTACTTTTCAAG TTCTCATTCCGGTGC AACTGACAACTGTTC AGGTCGTCGTGTCGG

Y  M  E  F  S     R  L  T  S  E     D  S  A  I  Y     Y  C  A  R  S
 241  TATATGGAGTTTAGC CGATTGACATCTGAG GATTCTGCAATCTAT TACTGTGCAAGATCG
      ATATACCTCAAATCG GCTAACTGTAGACTC CTAAGACGTTAGATA ATGACACGTTCTAGC

G  L  I  A  V     Y  F  D  Y  W     G  Q  G  T  T     V  T  V  S  S
 301  GGTCTGATAGCAGTC TACTTTGATTACTGG GGCCAAGGGACCACG GTCACCGTCTCCTCA
      CCAGACTATCGTCAG ATGAAACTAATGACC CCGGTTCCCTGGTGC CAGTGGCAGAGGAGT

G  G  G  G  S     G  G  G  G  S     G  G  G  G  S     E  L  V  L  T
 361  GGTGGTGGTGGTTCT GGCGGCGGCGGCTCC GGTGGTGGTGGTTCT GAGCTCGTGCTGACT
      CCACCACCACCAAGA CCGCCGCCGCCGAGG CCACCACCACCAAGA CTCGAGCACGACTGA

Q  S  P  D  F     Q  S  V  T  P     K  E  K  V  T     I  T  C  R  A
 421  CAGTCTCCAGACTTT CAGTCTGTGACTCCA AAGGAGAAAGTCACC ATCACCTGCCGGGCC
      GTCAGAGGTCTGAAA GTCAGACACTGAGGT TTCCTCTTTCAGTGG TAGTGGACGGCCCGG

S  Q  S  I  G     S  S  L  H  W     Y  Q  Q  K  P     D  Q  S  P  K
 481  AGTCAGAGCATTGGT AGTAGCTTACACTGG TACCAGCAGAAACCA GATCAGTCTCCAAAG
      TCAGTCTCGTAACCA TCATCGAATGTGACC ATGGTCGTCTTTGGT CTAGTCAGAGGTTTC

L  L  I  K  F     A  S  Q  S  L     S  G  V  P  S     R  F  S  G  S
 541  CTCCTCATCAAGTTT GCTTCCCAGTCCCTC TCAGGGGTCCCCTCG AGGTTCAGTGGCAGT
      GAGGAGTAGTTCAAA CGAAGGGTCAGGGAG AGTCCCCAGGGGAGC TCCAAGTCACCGTCA

G  S  G  T  D     F  T  L  T  I     S  S  L  Q  P     E  D  F  A  T
 601  GGATCTGGGACAGAT TTCACTCTCACCATC AGCAGTCTACAACCT GAAGATTTTGCAACT
      CCTAGACCCTGTCTA AAGTGAGAGTGGTAG TCGTCAGATGTTGGA CTTCTAAAACGTTGA

Y  Y  C  Q  Q     S  Y  T  T  P     P  T  F  G  G     G  T  K  V  E
 661  TACTACTGTCAACAG AGTTACACTACCCCC CCCACTTTCGGCGGA GGGACCAAGGTGGAA
      ATGATGACAGTTGTC TCAATGTGATGGGGG GGGTGAAAGCCGCCT CCCTGGTTCCACCTT

I  K
 721  ATCAAA
      TAGTTT
```

Fig. 17

B32oN-67

```
              E   L   Q   L   V     E   Q   S   G   A     A   L   V   K   P     G   D   S   V   K
  1   GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

M   S   C   K   A     S   G   Y   P   F     T   D   Y   I   V     H   W   V   K   Q
 61   ATGTCTTGCAAAGCT TCTGGTTATCCATTC ACTGACTATATTGTA CACTGGGTGAAGCAG
      TACAGAACGTTTCGA AGACCAATAGGTAAG TGACTGATATAACAT GTGACCCACTTCGTC

S   H   G   K   S     L   D   W   I   G     Y   I   N   P   Y     S   G   D   T   K
121   AGTCATGGAAAGAGC CTTGACTGGATTGGT TATATTAATCCTTAC AGTGGTGATACTAAG
      TCAGTACCTTTCTCG GAACTGACCTAACCA ATATAATTAGGAATG TCACCACTATGATTC

F   N   E   K   F     K   S   K   A   T     L   T   V   D   K     S   S   S   T   A
181   TTCAATGAAAAGTTC AAGAGTAAGGCCACG TTGACTGTTGACAAG TCCAGCAGCACAGCC
      AAGTTACTTTTCAAG TTCTCATTCCGGTGC AACTGACAACTGTTC AGGTCGTCGTGTCGG

Y   M   E   F   S     R   L   T   S   E     D   S   A   I   Y     Y   C   A   R   S
241   TATATGGAGTTTAGC CGGATTGACATCTGAG GATTCTGCAATCTAT TACTGTGCAAGATCG
      ATATACCTCAAATCG GCTAACTGTAGACTC CTAAGACGTTAGATA ATGACACGTTCTAGC

G   L   I   A   V     Y   F   D   Y     W   G   Q   G   T   T     V   T   V   S   S
301   GGTCTGATAGCAGTC TACTTTGATTACTGG GGCCAAGGGACCACG GTCACCGTCTCCTCA
      CCAGACTATCGTCAG ATGAAACTAATGACC CCGGTTCCCTGGTGC CAGTGGCAGAGGAGT

G   G   G   G   S     G   G   G   G   S     G   G   G   G   S     E   L   V   L   T
361   GGTGGTGGTGGTTCT GGCGGCGGCGGCTCC GGTGGTGGTGGTTCT GAGCTCGTGCTGACT
      CCACCACCACCAAGA CCGCCGCCGCCGAGG CCACCACCACCAAGA CTCGAGCACGACTGA

Q   S   P   G   F     Q   S   V   T   P     K   E   K   V   T     I   T   C   R   A
421   CAGTCTCCCGGCTTT CAGTCTGTGACTCCA AAGGAGAAAGTCACC ATCACCTGCCGGGCC
      GTCAGAGGGCCGAAA GTCAGACACTGAGGT TTCCTCTTTCAGTGG TAGTGGACGGCCCGG

S   Q   S   I   G     S   S   L   H   W     Y   Q   Q   K   P     D   Q   S   P   K
481   AGTCAGAGCATTGGT AGTAGCTTACACTGG TACCAGCAGAAACCA GATCAGTCTCCAAAG
      TCAGTCTCGTAACCA TCATCGAATGTGACC ATGGTCGTCTTTGGT CTAGTCAGAGGTTTC

L   L   I   K   F     A   S   Q   S   I     S   G   V   P   S     R   F   T   G   S
541   CTCCTCATCAAATTT GCTTCCCAGTCCATC TCAGGGGTCCCCTCG AGGTTCACTGGCAGT
      GAGGAGTAGTTTAAA CGAAGGGTCAGGTAG AGTCCCCAGGGGAGC TCCAAGTGACCGTCA

G   S   G   T   D     F   T   L   T   I     S   S   L   Q   P     E   D   I   A   T
601   GGATCTGGGACAGAT TTCACTCTCACCATC AGCAGTCTGCAACCT GAAGATATTGCAACT
      CCTAGACCCTGTCTA AAGTGAGAGTGGTAG TCGTCAGACGTTGGA CTTCTATAACGTTGA

Y   Y   C   Q   Q     S   Y   S   T   P     W   T   F   G   Q     G   T   K   L   E
661   TACTACTGTCAACAG AGTTACAGTACCCCT TGGACGTTCGGCCAA GGGACCAAGCTGGAG
      ATGATGACAGTTGTC TCAATGTCATGGGGA ACCTGCAAGCCGGTT CCCTGGTTCGACCTC

I   K
721   ATCAAA
      TAGTTT
```

Fig. 18

B32oN-73

```
         E   L   Q   L   V   E   Q   S   G   A   A   L   V   K   P   G   D   S   V   K
  1   GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

M   S   C   K   A   S   G   Y   P   F   T  |D   Y   I   V | H   W   V   K   Q
 61   ATGTCTTGCAAAGCT TCTGGTTATCCATTC ACTGACTATATTGTA CACTGGGTGAAGCAG
      TACAGAACGTTTCGA AGACCAATAGGTAAG TGACTGATATAACAT GTGACCCACTTCGTC

S   H   G   K   S   L   D   W   I   G  |Y   I   N   P   Y   S   G   D   T   K
121   AGTCATGGAAAGAGC CTTGACTGGATTGGT TATATTAATCCTTAC AGTGGTGATACTAAG
      TCAGTACCTTTCTCG GAACTGACCTAACCA ATATAATTAGGAATG TCACCACTATGATTC

|F   N   E   K   F   K   S | K   A   T   L   T   V   D   K   S   S   S   T   A
181   TTCAATGAAAAGTTC AAGAGTAAGGCCACG TTGACTGTTGACAAG TCCAGCAGCACAGCC
      AAGTTACTTTTCAAG TTCTCATTCCGGTGC AACTGACAACTGTTC AGGTCGTCGTGTCGG

Y   M   E   F   S   R   L   T   S   E   D   S   A   I   Y   Y   C   A   R  |S
241   TATATGGAGTTTAGC CGATTGACATCTGAG GATTCTGCAATCTAT TACTGTGCAAGATCG
      ATATACCTCAAATCG GCTAACTGTAGACTC CTAAGACGTTAGATA ATGACACGTTCTAGC

G   L   I   A   V   Y   F   D   Y | W   G   Q   G   T   T   V   T   V   S   S
301   GGTCTGATAGCAGTC TACTTTGATTACTGG GGCCAAGGGACCACG GTCACCGTCTCCTCA
      CCAGACTATCGTCAG ATGAAACTAATGACC CCGGTTCCCTGGTGC CAGTGGCAGAGGAGT

G   G   G   G   S   G   G   G   G   S   G   G   G   G   S   E   L   V   L   T
361   GGTGGTGGTGGTTCT GGCGGCGGCGGCTCC GGTGGTGGTGGTTCT GAGCTCGTGCTGACT
      CCACCACCACCAAGA CCGCCGCCGCCGAGG CCACCACCACCAAGA CTCGAGCACGACTGA

Q   S   P   G   F   Q   S   V   T   P   K   E   K   V   T   I   T   C  |R   A
421   CAGTCTCCCGGCTTT CAGTCTGTGACTCCA AAGGAGAAAGTCACC ATCACCTGCCGGGCC
      GTCAGAGGGCCGAAA GTCAGACACTGAGGT TTCCTCTTTCAGTGG TAGTGGACGGCCCGG

S   Q   S   I   G   S   S   L   H | W   Y   Q   Q   K   P   D   Q   S   P   K
481   AGTCAGAGCATTGGT AGTAGCTTACACTGG TACCAGCAGAAACCA GATCAGTCTCCAAAG
      TCAGTCTCGTAACCA TCATCGAATGTGACC ATGGTCGTCTTTGGT CTAGTCAGAGGTTTC

L   L   I   K  |F   A   S   Q   S   I   S | G   V   P   S   R   F   S   G   T
541   CTCCTCATCAAATTT GCTTCCCAGTCCATC TCAGGGGTCCCCTCG AGGTTCAGTGGCACT
      GAGGAGTAGTTTAAA CGAAGGGTCAGGTAG AGTCCCCAGGGGAGC TCCAAGTCACCGTGA

G   S   G   T   D   F   T   L   T   I   S   S   L   Q   P   E   D   I   A   T
601   GGATCTGGGACAGAT TTCACTCTCACCATC AGCAGTCTGCAACCT GAAGATATTGCAACT
      CCTAGACCCTGTCTA AAGTGAGAGTGGTAG TCGTCAGACGTTGGA CTTCTATAACGTTGA

Y   Y   C  |Q   Q   S   Y   S   T   P   W   T | F   G   Q   G   T   K   L   E
661   TACTACTGTCAACAG AGTTACAGTACCCCT TGGACGTTCGGCCAA GGGACCAAGCTGGAG
      ATGATGACAGTTGTC TCAATGTCATGGGGA ACCTGCAAGCCGGTT CCCTGGTTCGACCTC

I   K
721   ATCAAA
      TAGTTT
```

Fig. 19

B33oN-21

```
        E   L   Q   L   V    E   Q   S   G   A    A   L   V   K   P    G   D   S   V   K
  1   GAGCTGCAGCTGGTC     GAGCAGTCTGGAGCT     GCACTGGTGAAGCCT     GGGGACTCTGTGAAG
      CTCGACGTCGACCAG     CTCGTCAGACCTCGA     CGTGACCACTTCGGA     CCCCTGAGACACTTC

M   S   C   K   A    S   G   Y   P   F    T   D   Y   I   V    H   W   V   K   Q
 61   ATGTCTTGCAAAGCT     TCTGGTTATCCATTC     ACTGACTATATTGTA     CACTGGGTGAAGCAG
      TACAGAACGTTTCGA     AGACCAATAGGTAAG     TGACTGATATAACAT     GTGACCCACTTCGTC

S   H   G   K   S    L   D   W   I   G    Y   I   N   P   Y    S   G   D   T   K
121   AGTCATGGAAAGAGC     CTTGACTGGATTGGT     TATATTAATCCTTAC     AGTGGTGATACTAAG
      TCAGTACCTTTCTCG     GAACTGACCTAACCA     ATATAATTAGGAATG     TCACCACTATGATTC

F   N   E   K   F    K   S   K   A   T    L   T   V   D   K    S   S   S   T   A
181   TTCAATGAAAAGTTC     AAGAGTAAGGCCACG     TTGACTGTTGACAAG     TCCAGCAGCACAGCC
      AAGTTACTTTTCAAG     TTCTCATTCCGGTGC     AACTGACAACTGTTC     AGGTCGTCGTGTCGG

Y   M   E   F   S    R   L   T   S   E    D   S   A   I   Y    Y   C   A   R   S
241   TATATGGAGTTTAGC     CGATTGACATCTGAG     GATTCTGCAATCTAT     TACTGTGCAAGATCG
      ATATACCTCAAATCG     GCTAACTGTAGACTC     CTAAGACGTTAGATA     ATGACACGTTCTAGC

G   L   I   A   V    Y   F   D   Y   W    G   Q   G   T   T    V   T   V   S   S
301   GGTCTGATAGCAGTC     TACTTTGATTACTGG     GGCCAAGGGACCACG     GTCACCGTCTCCTCA
      CCAGACTATCGTCAG     ATGAAACTAATGACC     CCGGTTCCCTGGTGC     CAGTGGCAGAGGAGT

G   G   G   S    G   G   G   S    G   G   G   S    E   L   V   L   T
361   GGTGGTGGTGGTTCT     GGCGGCGGCGGCTCC     GGTGGTGGTGGTTCT     GAGCTCGTGCTGACT
      CCACCACCACCAAGA     CCGCCGCCGCCGAGG     CCACCACCACCAAGA     CTCGAGCACGACTGA

Q   S   P   D   F    Q   S   V   T   P    K   E   K   V   T    I   T   C   R   A
421   CAGTCTCCAGACTTT     CAGTCTGTGACTCCA     AAGGAGAAAGTCACC     ATCACCTGCCGGGCC
      GTCAGAGGTCTGAAA     GTCAGACACTGAGGT     TTCCTCTTTCAGTGG     TAGTGGACGGCCCGG

S   Q   S   I   G    S   S   L   H   W    Y   Q   Q   K   P    D   Q   S   P   K
481   AGTCAGAGCATTGGT     AGTAGCTTACACTGG     TACCAGCAGAAACCA     GATCAGTCTCCAAAG
      TCAGTCTCGTAACCA     TCATCGAATGTGACC     ATGGTCGTCTTTGGT     CTAGTCAGAGGTTTC

L   L   I   K   F    A   S   Q   S   L    S   G   V   P   S    R   F   S   G   S
541   CTCCTCATCAAGTTT     GCTTCCCAGTCCCTC     TCAGGGGTCCCCTCG     AGGTTCAGTGGCAGT
      GAGGAGTAGTTCAAA     CGAAGGGTCAGGGAG     AGTCCCCAGGGGAGC     TCCAAGTCACCGTCA

G   S   G   T   D    F   T   L   T   I    N   S   L   E   A    E   D   A   A   T
601   GGATCCGGGACAGAT     TTCACCCTCACCATC     AATAGCCTGGAAGCT     GAAGATGCTGCAACG
      CCTAGGCCCTGTCTA     AAGTGGGAGTGGTAG     TTATCGGACCTTCGA     CTTCTACGACGTTGC

Y   Y   C   Q   Q    S   Y   S   T   P    W   T   F   G   Q    G   T   K   L   E
661   TATTACTGTCAACAG     AGTTACAGTACCCCG     TGGACGTTCGGCCAA     GGGACCAAGCTGGAG
      ATAATGACAGTTGTC     TCAATGTCATGGGGC     ACCTGCAAGCCGGTT     CCCTGGTTCGACCTC

I   K
721   ATCAAA
      TAGTTT
```

Fig. 20

B33oN-22

```
          E  L  Q  L  V    E  Q  S  G  A    A  L  V  K  P    G  D  S  V  K
  1  GAGCTGCAGCTGGTC  GAGCAGTCTGGAGCT  GCACTGGTGAAGCCT  GGGGACTCTGTGAAG
     CTCGACGTCGACCAG  CTCGTCAGACCTCGA  CGTGACCACTTCGGA  CCCCTGAGACACTTC

M  S  C  K  A    S  G  Y  P  F    T  D  Y  I  V    H  W  V  K  Q
 61  ATGTCTTGCAAAGCT  TCTGGTTATCCATTC  ACTGACTATATTGTA  CACTGGGTGAAGCAG
     TACAGAACGTTTCGA  AGACCAATAGGTAAG  TGACTGATATAACAT  GTGACCCACTTCGTC

S  H  G  K  S    L  D  W  I  G    Y  I  N  P  Y    S  G  D  T  K
121  AGTCATGGAAAGAGC  CTTGACTGGATTGGT  TATATTAATCCTTAC  AGTGGTGATACTAAG
     TCAGTACCTTTCTCG  GAACTGACCTAACCA  ATATAATTAGGAATG  TCACCACTATGATTC

F  N  E  K  F    K  S  K  A  T    L  T  V  D  K    S  S  S  T  A
181  TTCAATGAAAAGTTC  AAGAGTAAGGCCACG  TTGACTGTTGACAAG  TCCAGCAGCACAGCC
     AAGTTACTTTTCAAG  TTCTCATTCCGGTGC  AACTGACAACTGTTC  AGGTCGTCGTGTCGG

Y  M  E  F  S    R  L  T  S  E    D  S  A  I  Y    Y  C  A  R  S
241  TATATGGAGTTTAGC  CGATTGACATCTGAG  GATTCTGCAATCTAT  TACTGTGCAAGATCG
     ATATACCTCAAATCG  GCTAACTGTAGACTC  CTAAGACGTTAGATA  ATGACACGTTCTAGC

G  L  I  A  V    Y  F  D  Y  W    G  Q  G  T  T    V  T  V  S  S
301  GGTCTGATAGCAGTC  TACTTTGATTACTGG  GGCCAAGGGACCACG  GTCACCGTCTCCTCA
     CCAGACTATCGTCAG  ATGAAACTAATGACC  CCGGTTCCCTGGTGC  CAGTGGCAGAGGAGT

G  G  G  G  S    G  G  G  G  S    G  G  G  G  S    E  L  V  L  T
361  GGTGGTGGTGGTTCT  GGCGGCGGCGGCTCC  GGTGGTGGTGGTTCT  GAGCTCGTGCTGACT
     CCACCACCACCAAGA  CCGCCGCCGCCGAGG  CCACCACCACCAAGA  CTCGAGCACGACTGA

Q  S  P  D  F    Q  S  V  T  P    K  E  K  V  T    I  T  C  R  A
421  CAGTCTCCAGACTTT  CAGTCTGTGACTCCA  AAGGAGAAAGTCACC  ATCACCTGCCGGGCC
     GTCAGAGGTCTGAAA  GTCAGACACTGAGGT  TTCCTCTTTCAGTGG  TAGTGGACGGCCCGG

S  Q  S  I  G    S  S  L  H  W    Y  Q  Q  K  P    D  Q  S  P  K
481  AGTCAGAGCATTGGT  AGTAGCTTACACTGG  TACCAGCAGAAACCA  GATCAGTCTCCAAAG
     TCAGTCTCGTAACCA  TCATCGAATGTGACC  ATGGTCGTCTTTGGT  CTAGTCAGAGGTTTC

L  L  I  K  F    A  S  Q  S  F    S  G  V  P  S    R  F  S  G  S
541  CTCCTCATCAAGTTT  GCTTCCAGTCCTTC  TCAGGGGTCCCCTCG  AGGTTCAGTGGCAGT
     GAGGAGTAGTTCAAA  CGAAGGGTCAGGAAG  AGTCCCCAGGGGAGC  TCCAAGTCACCGTCA

G  S  G  T  D    F  T  L  T  I    N  S  L  E  A    E  D  A  A  T
601  GGATCTGGGACAGAT  TTCACCCTCACCATC  AATAGCCTGGAAGCT  GAAGATGCTGCAACG
     CCTAGACCCTGTCTA  AAGTGGGAGTGGTAG  TTATCGGACCTTCGA  CTTCTACGACGTTGC

Y  Y  C  Q  Q    S  Y  S  T  P    P  T  F  G  Q    G  T  K  V  E
661  TATTACTGTCAACAG  AGTTACAGTACCCCT  CCGACGTTCGGCCAA  GGGACCAAGGTGGAG
     ATAATGACAGTTGTC  TCAATGTCATGGGGA  GGCTGCAAGCCGGTT  CCCTGGTTCCACCTC

I  K
721  ATCAAA
     TAGTTT
```

Fig. 21

B33oN-115

```
            E   L   Q   L   V     E   Q   S   G   A     A   L   V   K   P     G   D   S   V   K
  1    GAGCTGCAGCTGGTC   GAGCAGTCTGGAGCT   GCACTGGTGAAGCCT   GGGGACTCTGTGAAG
       CTCGACGTCGACCAG   CTCGTCAGACCTCGA   CGTGACCACTTCGGA   CCCCTGAGACACTTC

M   S   C   K   A     S   G   Y   P   F     T   D   Y   I   V     H   W   V   K   Q
 61    ATGTCTTGCAAAGCT   TCTGGTTATCCATTC   ACTGACTATATTGTA   CACTGGGTGAAGCAG
       TACAGAACGTTTCGA   AGACCAATAGGTAAG   TGACTGATATAACAT   GTGACCCACTTCGTC

S   H   G   K   S     L   D   W   I   G     Y   I   N   P   Y     S   G   D   T   K
121    AGTCATGGAAAGAGC   CTTGACTGGATTGGT   TATATTAATCCTTAC   AGTGGTGATACTAAG
       TCAGTACCTTTCTCG   GAACTGACCTAACCA   ATATAATTAGGAATG   TCACCACTATGATTC

F   N   E   K   F     K   S   K   A   T     L   T   V   D   K     S   S   S   T   A
181    TTCAATGAAAAGTTC   AAGAGTAAGGCCACG   TTGACTGTTGACAAG   TCCAGCAGCACAGCC
       AAGTTACTTTTCAAG   TTCTCATTCCGGTGC   AACTGACAACTGTTC   AGGTCGTCGTGTCGG

Y   M   E   F   S     R   L   T   S   E     D   S   A   I   Y     Y   C   A   R   S
241    TATATGGAGTTTAGC   CGATTGACATCTGAG   GATTCTGCAATCTAT   TACTGTGCAAGATCG
       ATATACCTCAAATCG   GCTAACTGTAGACTC   CTAAGACGTTAGATA   ATGACACGTTCTAGC

G   L   I   A   V     Y   F   D   Y   W     G   Q   G   T   T     V   T   V   S   S
301    GGTCTGATAGCAGTC   TACTTTGATTACTGG   GGCCAAGGGACCACG   GTCACCGTCTCCTCA
       CCAGACTATCGTCAG   ATGAAACTAATGACC   CCGGTTCCCTGGTGC   CAGTGGCAGAGGAGT

G   G   G   G   S     G   G   G   G   S     G   G   G   G   S     E   L   V   L   T
361    GGTGGTGGTGGTTCT   GGCGGCGGCGGCTCC   GGTGGTGGTGGTTCT   GAGCTCGTGCTGACT
       CCACCACCACCAAGA   CCGCCGCCGCCGAGG   CCACCACCACCAAGA   CTCGAGCACGACTGA

Q   S   P   D   F     Q   S   V   T   P     K   E   K   V   T     I   T   C   R   A
421    CAGTCTCCAGACTTT   CAGTCTGTGACTCCA   AAGGAGAAAGTCACC   ATCACCTGCCGGGCC
       GTCAGAGGTCTGAAA   GTCAGACACTGAGGT   TTCCTCTTTCAGTGG   TAGTGGACGGCCCGG

S   Q   S   I   G     S   S   L   H   W     Y   Q   Q   K   P     D   Q   S   P   K
481    AGTCAGAGCATTGGT   AGTAGCTTACACTGG   TACCAGCAGAAACCA   GATCAGTCTCCAAAG
       TCAGTCTCGTAACCA   TCATCGAATGTGACC   ATGGTCGTCTTTGGT   CTAGTCAGAGGTTTC

L   L   I   K   F     A   S   Q   S   L     S   G   V   P   S     R   F   S   G   S
541    CTCCTCATCAAGTTT   GCTTCCCAGTCCCTC   TCAGGGGTCCCCTCG   AGGTTCAGTGGCAGT
       GAGGAGTAGTTCAAA   CGAAGGGTCAGGGAG   AGTCCCCAGGGGAGC   TCCAAGTCACCGTCA

G   S   G   T   D     F   T   L   T   I     S   S   L   Q   P     E   D   F   A   T
601    GGATCTGGGACAGAT   TTCACTCTCACCATC   AGCAGTCTGCAACCT   GAAGATTTTGCAACT
       CCTAGACCCTGTCTA   AAGTGAGAGTGGTAG   TCGTCAGACGTTGGA   CTTCTAAAACGTTGA

Y   Y   C   Q   Q     S   Y   S   T   P     S   T   F   G   P     G   T   K   V   E
661    TACTACTGTCAACAG   AGTTACAGTACCCCT   AGTACTTTCGGCCCT   GGGACCAAGGTGGAG
       ATGATGACAGTTGTC   TCAATGTCATGGGGA   TCATGAAAGCCGGGA   CCCTGGTTCCACCTC

I   K
721    ATCAAA
       TAGTTT
```

Fig. 22

B33oN-35

```
              E   L   Q   L   V     E   Q   S   G   A     A   L   V   K   P     G   D   S   V   K
  1   GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

M   S   C   K   A     S   G   Y   P   F     T   D   Y   I   V     H   W   V   K   Q
 61   ATGTCTTGCAAAGCT TCTGGTTATCCATTC ACTGACTATATTGTA CACTGGGTGAAGCAG
      TACAGAACGTTTCGA AGACCAATAGGTAAG TGACTGATATAACAT GTGACCCACTTCGTC

S   H   G   K   S     L   D   W   I   G     Y   I   N   P   Y     S   G   D   T   K
121   AGTCATGGAAAGAGC CTTGACTGGATTGGT TATATTAATCCTTAC AGTGGTGATACTAAG
      TCAGTACCTTTCTCG GAACTGACCTAACCA ATATAATTAGGAATG TCACCACTATGATTC

F   N   E   K   F     K   S   K   A   T     L   T   V   D   K     S   S   S   T   A
181   TTCAATGAAAAGTTC AAGAGTAAGGCCACG TTGACTGTTGACAAG TCCAGCAGCACAGCC
      AAGTTACTTTTCAAG TTCTCATTCCGGTGC AACTGACAACTGTTC AGGTCGTCGTGTCGG

Y   M   E   F   S     R   L   T   S   E     D   S   A   I   Y     Y   C   A   R   S
241   TATATGGAGTTTAGC CGATTGACATCTGAG GATTCTGCAATCTAT TACTGTGCAAGATCG
      ATATACCTCAAATCG GCTAACTGTAGACTC CTAAGACGTTAGATA ATGACACGTTCTAGC

G   L   I   A   V     Y   F   D   Y   W     G   Q   G   T   T     V   T   V   S   S
301   GGTCTGATAGCAGTC TACTTTGATTACTGG GGCCAAGGGACCACG GTCACCGTCTCCTCA
      CCAGACTATCGTCAG ATGAAACTAATGACC CCGGTTCCCTGGTGC CAGTGGCAGAGGAGT

G   G   G   G   S     G   G   G   G   S     G   G   G   G   S     E   L   Q   M   T
361   GGTGGTGGTGGTTCT GGCGGCGGCGGCTCC GGTGGTGGTGGTTCT GAGCTCCAGATGACC
      CCACCACCACCAAGA CCGCCGCCGCCGAGG CCACCACCACCAAGA CTCGAGGTCTACTGG

Q   S   P   S   S     L   S   A   S   V     G   D   R   V   T     I   T   C   R   A
421   CAGTCTCCATCCTCC CTGTCTGCATCTGTA GGAGACAGAGTCACC ATCACCTGCCGGGCC
      GTCAGAGGTAGGAGG GACAGACGTAGACAT CCTCTGTCTCAGTGG TAGTGGACGGCCCGG

S   Q   S   I   G     S   S   L   H   W     Y   Q   Q   K   P     D   Q   S   P   K
481   AGTCAGAGCATTGGT AGTAGCTTACACTGG TACCAGCAGAAACCA GATCAGTCTCCAAAG
      TCAGTCTCGTAACCA TCATCGAATGTGACC ATGGTCGTCTTTGGT CTAGTCAGAGGTTTC

L   L   I   K   F     A   S   Q   S   F     S   G   V   P   S     R   F   G   G   S
541   CTCCTCATCAAGTTT GCTTCCCAGTCCTTC TCAGGGGTCCCCTCG AGGTTCGGTGGCAGT
      GAGGAGTAGTTCAAA CGAAGGGTCAGGAAG AGTCCCCAGGGGAGC TCCAAGCCACCGTCA

G   S   G   T   N     F   T   L   T   I     N   S   L   E   A     E   D   A   A   T
601   GGATCTGGGACAAAT TTCACCCTCACCATC AATAGCCTGGAAGCT GAAGATGCTGCAACC
      CCTAGACCCTGTTTA AAGTGGGAGTGGTAG TTATCGGACCTTCGA CTTCTACGACGTTGG

Y   Y   C   Q   Q     S   S   T   L   P     P   T   F   G   Q     G   T   K   L   E
661   TATTACTGTCAGCAG AGTAGTACTTTACCT CCCACTTTTGGCCAG GGGACCAAGCTGGAG
      ATAATGACAGTCGTC TCATCATGAAATGGA GGGTGAAAACCGGTC CCCTGGTTCGACCTC

I   K
721   ATCAAA
      TAGTTT
```

Fig. 23

B33oN-66

```
          E   L   Q   L   V     E   Q   S   G   A     A   L   V   K   P     G   D   S   V   K
  1    GAGCTGCAGCTGGTC   GAGCAGTCTGGAGCT   GCACTGGTGAAGCCT   GGGGACTCTGTGAAG
       CTCGACGTCGACCAG   CTCGTCAGACCTCGA   CGTGACCACTTCGGA   CCCCTGAGACACTTC

M   S   C   K   A     S   G   Y   P   F     T   D   Y   I   V     H   W   V   K   Q
 61    ATGTCTTGCAAAGCT   TCTGGTTATCCATTC   ACTGACTATATTGTA   CACTGGGTGAAGCAG
       TACAGAACGTTTCGA   AGACCAATAGGTAAG   TGACTGATATAACAT   GTGACCCACTTCGTC

S   H   G   K   S     L   D   W   I   G     Y   I   N   P   Y     S   G   D   T   K
121    AGTCATGGAAAGAGC   CTTGACTGGATTGGT   TATATTAATCCTTAC   AGTGGTGATACTAAG
       TCAGTACCTTTCTCG   GAACTGACCTAACCA   ATATAATTAGGAATG   TCACCACTATGATTC

F   N   E   K   F     K   S   K   A   T     L   T   V   D   K     S   S   S   T   A
181    TTCAATGAAAAGTTC   AAGAGTAAGGCCACG   TTGACTGTTGACAAG   TCCAGCAGCACAGCC
       AAGTTACTTTTCAAG   TTCTCATTCCGGTGC   AACTGACAACTGTTC   AGGTCGTCGTGTCGG

Y   M   E   F   S     R   L   T   S   E     D   S   A   I   Y     Y   C   A   R   S
241    TATATGGAGTTTAGC   CGATTGACATCTGAG   GATTCTGCAATCTAT   TACTGTGCAAGATCG
       ATATACCTCAAATCG   GCTAACTGTAGACTC   CTAAGACGTTAGATA   ATGACACGTTCTAGC

G   L   I   A   V     Y   F   D   Y   W     G   Q   G   T   T     V   T   V   S   S
301    GGTCTGATAGCAGTC   TACTTTGATTACTGG   GGCCAAGGGACCACG   GTCACCGTCTCCTCA
       CCAGACTATCGTCAG   ATGAAACTAATGACC   CCGGTTCCCTGGTGC   CAGTGGCAGAGGAGT

G   G   G   S     G   G   G   G   S     G   G   G   G   S     E   L   V   L   T
361    GGTGGTGGTGGTTCT   GGCGGCGGCGGCTCC   GGTGGTGGTGGTTCT   GAGCTCGTGCTGACT
       CCACCACCACCAAGA   CCGCCGCCGCCGAGG   CCACCACCACCAAGA   CTCGAGCACGACTGA

Q   S   P   D   F     Q   S   V   T   P     K   E   V   T     I   T   C   R   A
421    CAGTCTCCAGACTTT   CAGTCTGTGACTCCA   AAGGAGAAAGTCACC   ATCACCTGCCGGGCC
       GTCAGAGGTCTGAAA   GTCAGACACTGAGGT   TTCCTCTTTCAGTGG   TAGTGGACGGCCCGG

S   Q   S   I   G     S   N   L   H   W     Y   Q   Q   K   P     D   Q   S   P   K
481    AGTCAGAGCATTGGT   AGTAACTTACACTGG   TACCAGCAGAAACCA   GATCAGTCTCCAAAG
       TCAGTCTCGTAACCA   TCATTGAATGTGACC   ATGGTCGTCTTTGGT   CTAGTCAGAGGTTTC

L   L   I   K   F     A   S   Q   S   F     S   G   V   P   S     R   F   S   G   S
541    CTCCTCATCAAGTTT   GCTTCCCAGTCCTTC   TCAGGGGTCCCCTCG   AGGTTCAGTGGCAGT
       GAGGAGTAGTTCAAA   CGAAGGGTCAGGAAG   AGTCCCCAGGGGAGC   TCCAAGTCACCGTCA

G   S   G   T   D     F   S   L   T   I     N   S   L   E   A     E   D   A   A   T
601    GGATCTGGGACAGAT   TTCAGCCTCACCATC   AATAGCCTGGAAGCT   GAAGATGCTGCAACT
       CCTAGACCCTGTCTA   AAGTCGGAGTGGTAG   TTATCGGACCTTCGA   CTTCTACGACGTTGA

Y   Y   C   Q   Q     S   Y   S   T   P     P   T   F   G   Q     G   T   R   L   E
661    TACTACTGTCAACAG   AGTTACAGTACCCCT   CCCACCTTCGGCCAA   GGGACACGACTGGAG
       ATGATGACAGTTGTC   TCAATGTCATGGGGA   GGGTGGAAGCCGGTT   CCCTGTGCTGACCTC

I   K
721    ATTAAA
       TAATTT
```

Fig. 24

B33oN-67

```
        E   L   Q   L   V     E   Q   S   G   A     A   L   V   K   P     G   D   S   V   K
  1   GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

M   S   C   K   A     S   G   Y   P   F     T   D   Y   I   V     H   W   V   K   Q
 61   ATGTCTTGCAAAGCT TCTGGTTATCCATTC ACTGACTATATTGTA CACTGGGTGAAGCAG
      TACAGAACGTTTCGA AGACCAATAGGTAAG TGACTGATATAACAT GTGACCCACTTCGTC

S   H   G   K   S     L   D   W   I   G     Y   I   N   P   Y     S   G   D   T   K
121   AGTCATGGAAAGAGC CTTGACTGGATTGGT TATATTAATCCTTAC AGTGGTGATACTAAG
      TCAGTACCTTTCTCG GAACTGACCTAACCA ATATAATTAGGAATG TCACCACTATGATTC

F   N   E   K   F     K   S   K   A   T     L   T   V   D   K     S   S   S   T   A
181   TTCAATGAAAAGTTC AAGAGTAAGGCCACG TTGACTGTTGACAAG TCCAGCAGCACAGCC
      AAGTTACTTTTCAAG TTCTCATTCCGGTGC AACTGACAACTGTTC AGGTCGTCGTGTCGG

Y   M   E   F   S     R   L   T   S   E     D   S   A   I   Y     Y   C   A   R   S
241   TATATGGAGTTTAGC CGATTGACATCTGAG GATTCTGCAATCTAT TACTGTGCAAGATCG
      ATATACCTCAAATCG GCTAACTGTAGACTC CTAAGACGTTAGATA ATGACACGTTCTAGC

G   L   I   A   V     Y   F   D   Y   W     G   Q   G   T   T     V   T   V   S   S
301   GGTCTGATAGCAGTC TACTTTGATTACTGG GGCCAAGGGACCACG GTCACCGTCTCCTCA
      CCAGACTATCGTCAG ATGAAACTAATGACC CCGGTTCCCTGGTGC CAGTGGCAGAGGAGT

G   G   G   G   S     G   G   G   G   S     G   G   G   G   S     E   L   V   L   T
361   GGTGGTGGTGGTTCT GGCGGCGGCGGCTCC GGTGGTGGTGGTTCT GAGCTCGTGCTGACT
      CCACCACCACCAAGA CCGCCGCCGCCGAGG CCACCACCACCAAGA CTCGAGCACGACTGA

Q   S   P   D   F     Q   S   V   T   P     K   E   K   V   T     I   T   C   R   A
421   CAGTCTCCAGACTTT CAGTCTGTGACTCCA AAGGAGAAAGTCACC ATCACCTGCCGGGCC
      GTCAGAGGTCTGAAA GTCAGACACTGAGGT TTCCTCTTTCAGTGG TAGTGGACGGCCCGG

S   Q   S   I   G     S   S   L   H   W     Y   Q   Q   K   P     D   Q   S   P   K
481   AGTCAGAGCATTGGT AGTAGCTTACACTGG TACCAGCAGAAACCA GATCAGTCTCCAAAG
      TCAGTCTCGTAACCA TCATCGAATGTGACC ATGGTCGTCTTTGGT CTAGTCAGAGGTTTC

L   L   I   K   F     A   S   Q   S   I     S   G   V   P   S     R   F   S   G   S
541   CTCCTCATCAAATTT GCTTCCCAGTCCATC TCAGGGGTCCCATCG AGGTTCAGTGGCAGT
      GAGGAGTAGTTTAAA CGAAGGGTCAGGTAG AGTCCCCAGGGTAGC TCCAAGTCACCGTCA

G   S   G   T   D     F   T   L   T   I     S   S   L   Q   P     E   D   F   A   T
601   GGATCTGGGACAGAT TTCACTCTCACCATC AGCAGTCTGCAACCT GAAGATTTTGCAACT
      CCTAGACCCTGTCTA AAGTGAGAGTGGTAG TCGTCAGACGTTGGA CTTCTAAAACGTTGA

Y   Y   C   Q   Q     S   Y   S   T   P     P   T   F   G   P     G   T   K   L   E
661   TACTACTGTCAACAG AGTTACAGTACCCCT CCCACTTTCGGCCCT GGGACCAAGCTGGAG
      ATGATGACAGTTGTC TCAATGTCATGGGGA GGGTGAAAGCCGGGA CCCTGGTTCGACCTC

I   K
721   ATCAAA
      TAGTTT
```

Fig. 25

B33oN-69

```
              E   L   Q   L   V     E   Q   S   G   A     A   L   V   K   P     G   D   S   V   K
  1   GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

M   S   C   K   A     S   G   Y   P   F     T   D   Y   I   V     H   W   V   K   Q
 61   ATGTCTTGCAAAGCT TCTGGTTATCCATTC ACTGACTATATTGTA CACTGGGTGAAGCAG
      TACAGAACGTTTCGA AGACCAATAGGTAAG TGACTGATATAACAT GTGACCCACTTCGTC

S   H   G   K   S     L   D   W   I   G     Y   I   N   P   Y     S   G   D   T   K
121   AGTCATGGAAAGAGC CTTGACTGGATTGGT TATATTAATCCTTAC AGTGGTGATACTAAG
      TCAGTACCTTTCTCG GAACTGACCTAACCA ATATAATTAGGAATG TCACCACTATGATTC

F   N   E   K   F     K   S   K   A   T     L   T   V   D   K     S   S   S   T   A
181   TTCAATGAAAAGTTC AAGAGTAAGGCCACG TTGACTGTTGACAAG TCCAGCAGCACAGCC
      AAGTTACTTTTCAAG TTCTCATTCCGGTGC AACTGACAACTGTTC AGGTCGTCGTGTCGG

Y   M   E   F   S     R   L   T   S   E     D   S   A   I   Y     Y   C   A   R   S
241   TATATGGAGTTTAGC CGATTGACATCTGAG GATTCTGCAATCTAT TACTGTGCAAGATCG
      ATATACCTCAAATCG GCTAACTGTAGACTC CTAAGACGTTAGATA ATGACACGTTCTAGC

G   L   I   A   V     Y   F   D   Y   W     G   Q   G   T   T     V   T   V   S   S
301   GGTCTGATAGCAGTC TACTTTGATTACTGG GGCCAAGGGACCACG GTCACCGTCTCCTCA
      CCAGACTATCGTCAG ATGAAACTAATGACC CCGGTTCCCTGGTGC CAGTGGCAGAGGAGT

G   G   G   G   S     G   G   G   G   S     G   G   G   G   S     E   L   V   L   T
361   GGTGGTGGTGGTTCT GGCGGCGGCGGCTCC GGTGGTGGTGGTTCT GAGCTCGTGCTGACT
      CCACCACCACCAAGA CCGCCGCCGCCGAGG CCACCACCACCAAGA CTCGAGCACGACTGA

Q   S   P   D   F     Q   S   V   T   P     K   E   K   V   T     I   T   C   R   A
421   CAGTCTCCAGACTTT CAATCTGTGACTCCA AAGGAGAAAGTCACC ATCACCTGCCGGGCC
      GTCAGAGGTCTGAAA GTTAGACACTGAGGT TTCCTCTTTCAGTGG TAGTGGACGGCCCGG

S   Q   S   I   G     T   G   L   H   W     Y   Q   Q   K   P     D   Q   S   P   K
481   AGTCAGAGCATTGGT ACTGGCTTACACTGG TACCAGCAGAAACCG GATCAGTCTCCAAAG
      TCAGTCTCGTAACCA TGACCGAATGTGACC ATGGTCGTCTTTGGC CTAGTCAGAGGTTTC

L   L   I   K   F     A   S   Q   S   F     S   G   V   P   S     R   F   S   G   S
541   CTCCTCATCAAATTT GCTTCCCAGTCCTTC TCAGGGGTCCCCTCG AGGTTCAGTGGCAGT
      GAGGAGTAGTTTAAA CGAAGGGTCAGGAAG AGTCCCCAGGGGAGC TCCAAGTCACCGTCA

G   S   G   T   D     F   T   L   T   I     N   G   L   E   A     E   D   A   A   T
601   GGATCTGGGACAGAT TTCACCCTCACCATC AATGGCCTGGAAGCT GAAGATGCTGCAACG
      CCTAGACCCTGTCTA AAGTGGGAGTGGTAG TTACCGGACCTTCGA CTTCTACGACGTTGC

Y   Y   C   Q   Q     S   S   T   L   P     P   T   F   G   Q     G   T   K   L   E
661   TATTACTGTCAGCAG AGTAGTACTTTACCT CCCACTTTTGGCCAG GGGACCAAGCTGGAG
      ATAATGACAGTCGTC TCATCATGAAATGGA GGGTGAAAACCGGTC CCCTGGTTCGACCTC

I   K
721   ATCAAA
      TAGTTT
```

Fig. 26

B33oN-8

```
          E   L   Q   L   V     E   Q   S   G   A     A   L   V   K   P     G   D   S   V   K
  1   GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

M   S   C   K   A     S   G   Y   P   F     T   D   Y   I   V     H   W   V   K   Q
 61   ATGTCTTGCAAAGCT TCTGGTTATCCATTC ACTGACTATATTGTA CACTGGGTGAAGCAG
      TACAGAACGTTTCGA AGACCAATAGGTAAG TGACTGATATAACAT GTGACCCACTTCGTC

S   H   G   K   S     L   D   W   I   G     Y   I   N   P   Y     S   G   D   T   K
121   AGTCATGGAAAGAGC CTTGACTGGATTGGT TATATTAATCCTTAC AGTGGTGATACTAAG
      TCAGTACCTTTCTCG GAACTGACCTAACCA ATATAATTAGGAATG TCACCACTATGATTC

F   N   E   K   F     K   S   K   A   T     L   T   V   D   K     S   S   S   T   A
181   TTCAATGAAAAGTTC AAGAGTAAGGCCACG TTGACTGTTGACAAG TCCAGCAGCACAGCC
      AAGTTACTTTTCAAG TTCTCATTCCGGTGC AACTGACAACTGTTC AGGTCGTCGTGTCGG

Y   M   E   F   S     R   L   T   S   E     D   S   A   I   Y     Y   C   A   R   S
241   TATATGGAGTTTAGC CGATTGACATCTGAG GATTCTGCAATCTAT TACTGTGCAAGATCG
      ATATACCTCAAATCG GCTAACTGTAGACTC CTAAGACGTTAGATA ATGACACGTTCTAGC

G   L   I   A   V     Y   F   D   Y   W     G   Q   G   T   T     V   T   V   S   S
301   GGTCTGATAGCAGTC TACTTTGATTACTGG GGCCAAGGGACCACG GTCACCGTCTCCTCA
      CCAGACTATCGTCAG ATGAAACTAATGACC CCGGTTCCCTGGTGC CAGTGGCAGAGGAGT

G   G   G   G   S     G   G   G   G   S     G   G   G   G   S     E   L   V   L   T
361   GGTGGTGGTGGTTCT GGCGGCGGCGGCTCC GGTGGTGGTGGTTCT GAGCTCGTGCTGACT
      CCACCACCACCAAGA CCGCCGCCGCCGAGG CCACCACCACCAAGA CTCGAGCACGACTGA

Q   S   P   G   F     Q   S   V   T   P     K   E   K   V   T     I   T   C   R   A
421   CAGTCTCCAGGCTTT CAGTCTGTGACTCCA AAGGAGAAAGTCACC ATCACCTGCCGGGCC
      GTCAGAGGTCCGAAA GTCAGACACTGAGGT TTCCTCTTTCAGTGG TAGTGGACGGCCCGG

S   Q   S   I   G     S   S   L   N   W     Y   Q   Q   K   P     D   Q   P   P   K
481   AGTCAGAGCATTGGT AGTAGCTTAAACTGG TACCAGCAGAAACCA GATCAGCCTCCAAAG
      TCAGTCTCGTAACCA TCATCGAATTTGACC ATGGTCGTCTTTGGT CTAGTCGGAGGTTTC

L   L   I   K   F     A   S   Q   S   I     S   G   V   S   S     R   F   S   G   T
541   CTCCTCATCAAATTC GCTTCGCAGTCCATC TCAGGGGTCTCTTCG AGGTTCAGTGGCACT
      GAGGAGTAGTTTAAG CGAAGCGTCAGGTAG AGTCCCCAGAGAAGC TCCAAGTCACCGTGA

G   S   G   T   D     F   T   L   T   I     S   S   L   Q   P     E   D   V   A   T
601   GGATCTGGGACAGAT TTCACCCTCACTATC AGCAGCCTGCAGCCT GAAGATGTTGCAACT
      CCTAGACCCTGTCTA AAGTGGGAGTGATAG TCGTCGGACGTCGGA CTTCTACAACGTTGA

Y   Y   C   Q   Q     S   Y   S   T   P     P   T   F   G   Q     G   T   K   L   E
661   TATTACTGTCAACAG AGTTACAGTACCCCT CCGACGTTCGGCCAA GGGACCAAGCTGGAG
      ATAATGACAGTTGTC TCAATGTCATGGGGA GGCTGCAAGCCGGTT CCCTGGTTCGACCTC

I   K
721   ATCAAA
      TAGTTT
```

Fig. 27

C32oN-10

```
              E   L   Q   L   V    E   Q   S   G   A    A   L   V   K   P    G   D   S   V   K
  1         GAGCTGCAGCTGGTC   GAGCAGTCTGGAGCT   GCACTGGTGAAGCCT   GGGGACTCTGTGAAG
              CTCGACGTCGACCAG   CTCGTCAGACCTCGA   CGTGACCACTTCGGA   CCCCTGAGACACTTC

M   S   C   K   A    S   G   Y   P   F    T │ D   Y   I   V │  H   W   V   K   Q
 61         ATGTCTTGCAAAGCT   TCTGGTTATCCATTC   ACT GACTATATTGTA  CAC TGGGTGAAGCAG
              TACAGAACGTTTCGA   AGACCAATAGGTAAG   TGA CTGATATAACAT  GTG ACCCACTTCGTC

S   H   G   K   S    L   D   W   I   G  │ Y   I   N   P   Y    S   G   D   T   K
121         AGTCATGGAAAGAGC   CTTGACTGGATTGGT   TATATTAATCCTTAC   AGTGGTGATACTAAG
              TCAGTACCTTTCTCG   GAACTGACCTAACCA   ATATAATTAGGAATG   TCACCACTATGATTC

│ F   N   E   K   F    K   S │ K   A   T    L   T   V   D   K    S   S   S   T   A
181         TTCAATGAAAAGTTC   AAGAGT AAGGCCACG   TTGACTGTTGACAAG   TCCAGCAGCACAGCC
              AAGTTACTTTTCAAG   TTCTCA TTCCGGTGC   AACTGACAACTGTTC   AGGTCGTCGTGTCGG

Y   M   E   F   S    R   L   T   S   E    D   S   A   I   Y    Y   C   A   R │ S
241         TATATGGAGTTTAGC   CGATTGACATCTGAG   GATTCTGCAATCTAT   TACTGTGCAAGA TCG
              ATATACCTCAAATCG   GCTAACTGTAGACTC   CTAAGACGTTAGATA   ATGACACGTTCT AGC

G   L   I   A   V    Y   F   D   Y │ W    G   Q   G   T   T    V   T   V   S   S
301         GGTCTGATAGCAGTC   TACTTTGATTAC TGG   GGCCAAGGGACCACG   GTCACCGTCTCCTCA
              CCAGACTATCGTCAG   ATGAAACTAATG ACC   CCGGTTCCCTGGTGC   CAGTGGCAGAGGAGT

G   G   G   G   S    G   G   G   G   S    G   G   G   S    E   L   V   L   T
361         GGTGGTGGTGGTTCT   GGCGGCGGCGGCTCC   GGTGGTGGTGGTTCT   GAGCTCGTGCTGACT
              CCACCACCACCAAGA   CCGCCGCCGCCGAGG   CCACCACCACCAAGA   CTCGAGCACGACTGA

Q   S   P   D   F    Q   S   V   T   P    K   E   K   V   T    I   T   C │ R   A
421         CAGTCTCCAGACTTT   CAGTCTGTGACTCCA   AAGGAGAAAGTCACC   ATCACCTGC CGGGCC
              GTCAGAGGTCTGAAA   GTCAGACACTGAGGT   TTCCTCTTTCAGTGG   TAGTGGACG GCCCGG

│ S   Q   S   I   G    S   S   L   H │ W    Y   Q   Q   K   P    D   Q   S   P   K
481         AGTCAGAGCATTGGT   AGTAGCTTACAC TGG   TACCAGCAGAAACCA   GATCAGTCTCCAAAG
              TCAGTCTCGTAACCA   TCATCGAATGTG ACC   ATGGTCGTCTTTGGT   CTAGTCAGAGGTTTC

L   L   I   K │ F    A   S   Q   S   L    S │ G   V   P   S    R   F   S   G   S
541         CTCCTCATCAAG TTT   GCTTCCCAGTCCCTC   TCA GGGGTCCCCTCG   AGGTTCAGTGGCAGT
              GAGGAGTAGTTC AAA   CGAAGGGTCAGGGAG   AGT CCCCAGGGGAGC   TCCAAGTCACCGTCA

G   S   G   T   D    F   T   L   T   I    N   S   L   E   A    E   D   F   A   T
601         GGATCTGGGACAGAT   TTCACCCTCACCATC   AATAGCCTGGAAGCT   GAAGATTTTGCAACT
              CCTAGACCCTGTCTA   AAGTGGGAGTGGTAG   TTATCGGACCTTCGA   CTTCTAAAACGTTGA

Y   Y   C │ Q   Q    S   Y   S   T   P    S   T │ F   G   P    G   T   K   V   E
661         TACTACTGT CAACAG   AGTTACAGTACCCCT   AGTACT TTCGGCCCT   GGGACCAAGGTGGAG
              ATGATGACA GTTGTC   TCAATGTCATGGGGA   TCATGA AAGCCGGGA   CCCTGGTTCCACCTC

I   K
721         ATCAAA
              TAGTTT
```

Fig. 28

C32oN-21

```
          E   L   Q   L   V    E   Q   S   G   A    A   L   V   K   P    G   D   S   V   K
  1   GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

M   S   C   K   A    S   G   Y   P   F    T   D   Y   I   V    H   W   V   K   Q
 61   ATGTCTTGCAAAGCT TCTGGTTATCCATTC ACTGACTATATTGTA CACTGGGTGAAGCAG
      TACAGAACGTTTCGA AGACCAATAGGTAAG TGACTGATATAACAT GTGACCCACTTCGTC

S   H   G   K   S    L   D   W   I   G    Y   I   N   P   Y    S   G   D   T   K
121   AGTCATGGAAAGAGC CTTGACTGGATTGGT TATATTAATCCTTAC AGTGGTGATACTAAG
      TCAGTACCTTTCTCG GAACTGACCTAACCA ATATAATTAGGAATG TCACCACTATGATTC

F   N   E   K   F    K   S   K   A   T    L   T   V   D   K    S   S   S   T   A
181   TTCAATGAAAAGTTC AAGAGTAAGGCCACG TTGACTGTTGACAAG TCCAGCAGCACAGCC
      AAGTTACTTTTCAAG TTCTCATTCCGGTGC AACTGACAACTGTTC AGGTCGTCGTGTCGG

Y   M   E   F   S    R   L   T   S   E    D   S   A   I   Y    Y   C   A   R   S
241   TATATGGAGTTTAGC CGATTGACATCTGAG GATTCTGCAATCTAT TACTGTGCAAGATCG
      ATATACCTCAAATCG GCTAACTGTAGACTC CTAAGACGTTAGATA ATGACACGTTCTAGC

G   L   I   A   V    Y   F   D   Y    W   G   Q   G   T   T    V   T   V   S   S
301   GGTCTGATAGCAGTC TACTTTGATTACTGG GGCCAAGGGACCACG GTCACCGTCTCCTCA
      CCAGACTATCGTCAG ATGAAACTAATGACC CCGGTTCCCTGGTGC CAGTGGCAGAGGAGT

G   G   G   G   S    G   G   G   G   S    G   G   G   G   S    E   L   V   L   T
361   GGTGGTGGTGGTTCT GGCGGCGGCGGCTCC GGTGGTGGTGGTTCT GAGCTCGTGCTGACT
      CCACCACCACCAAGA CCGCCGCCGCCGAGG CCACCACCACCAAGA CTCGAGCACGACTGA

Q   S   P   G   F    Q   S   V   T   P    K   E   K   V   T    I   T   C   R   A
421   CAGTCTCCCGGCTTT CAGTCTGTGACTCCA AAGGAGAAAGTCACC ATCACCTGCCGGGCC
      GTCAGAGGGCCGAAA GTCAGACACTGAGGT TTCCTCTTTCAGTGG TAGTGGACGGCCCGG

S   Q   S   I   G    S   S   L   H   W    Y   Q   Q   K   P    D   Q   S   P   K
481   AGTCAGAGCATTGGT AGTAGCTTACACTGG TACCAGCAGAAACCA GATCAGTCTCCAAAG
      TCAGTCTCGTAACCA TCATCGAATGTGACC ATGGTCGTCTTTGGT CTAGTCAGAGGTTTC

L   L   I   K   F    A   S   Q   S   I    S   G   V   P   S    R   F   S   G   T
541   CTCCTCATCAAATTT GCTTCCCAGTCCATC TCAGGGGTCCCCTCG AGGTTCAGTGGCACT
      GAGGAGTAGTTTAAA CGAAGGGTCAGGTAG AGTCCCCAGGGGAGC TCCAAGTCACCGTGA

G   S   G   T   D    F   T   L   T   I    N   S   L   E   A    E   D   A   A   T
601   GGATCTGGGACAGAT TTCACCCTCACCATC AATAGCCTGGAAGCT GAAGATGCTGCAACC
      CCTAGACCCTGTCTA AAGTGGGAGTGGTAG TTATCGGACCTTCGA CTTCTACGACGTTGG

Y   Y   C   Q   Q    S   S   T   L   P    P   T   F   G   Q    G   T   K   L   E
661   TATTACTGTCAGCAG AGTAGTACTTTACCT CCCACTTTTGGCCAG GGGACCAAGCTGGAG
      ATAATGACAGTCGTC TCATCATGAAATGGA GGGTGAAAACCGGTC CCCTGGTTCGACCTC

I   K
721   ATCAAA
      TAGTTT
```

Fig. 29

C32oN-34

```
          E   L   Q   L   V    E   Q   S   G   A    A   L   V   K   P    G   D   S   V   K
  1   GAGCTGCAGCTGGTC  GAGCAGTCTGGAGCT  GCACTGGTGAAGCCT  GGGGACTCTGTGAAG
      CTCGACGTCGACCAG  CTCGTCAGACCTCGA  CGTGACCACTTCGGA  CCCCTGAGACACTTC

M   S   C   K   A    S   G   Y   P   F    T   D   Y   I   V    H   W   V   K   Q
 61   ATGTCTTGCAAAGCT  TCTGGTTATCCATTC  ACTGACTATATTGTA  CACTGGGTGAAGCAG
      TACAGAACGTTTCGA  AGACCAATAGGTAAG  TGACTGATATAACAT  GTGACCCACTTCGTC

S   H   G   K   S    L   D   W   I   G    Y   I   N   P   Y    S   G   D   T   K
121   AGTCATGGAAAGAGC  CTTGACTGGATTGGT  TATATTAATCCTTAC  AGTGGTGATACTAAG
      TCAGTACCTTTCTCG  GAACTGACCTAACCA  ATATAATTAGGAATG  TCACCACTATGATTC

F   N   E   K   F    K   S   K   A   T    L   T   V   D   K    S   S   S   T   A
181   TTCAATGAAAAGTTC  AAGAGTAAGGCCACG  TTGACTGTTGACAAG  TCCAGCAGCACAGCC
      AAGTTACTTTTCAAG  TTCTCATTCCGGTGC  AACTGACAACTGTTC  AGGTCGTCGTGTCGG

Y   M   E   F   S    R   L   T   S   E    D   S   A   I   Y    Y   C   A   R   S
241   TATATGGAGTTTAGC  CGATTGACATCTGAG  GATTCTGCAATCTAT  TACTGTGCAAGATCG
      ATATACCTCAAATCG  GCTAACTGTAGACTC  CTAAGACGTTAGATA  ATGACACGTTCTAGC

G   L   I   A   V    Y   F   D   Y   W    G   Q   G   T   T    V   T   V   S   S
301   GGTCTGATAGCAGTC  TACTTTGATTACTGG  GGCCAAGGGACCACG  GTCACCGTCTCCTCA
      CCAGACTATCGTCAG  ATGAAACTAATGACC  CCGGTTCCCTGGTGC  CAGTGGCAGAGGAGT

G   G   G   G   S    G   G   G   G   S    G   G   G   G   S    E   L   V   L   T
361   GGTGGTGGTGGTTCT  GGCGGCGGCGGCTCC  GGTGGTGGTGGTTCT  GAGCTCGTGCTGACT
      CCACCACCACCAAGA  CCGCCGCCGCCGAGG  CCACCACCACCAAGA  CTCGAGCACGACTGA

Q   S   P   D   F    Q   S   V   T   P    K   E   R   V   T    I   T   C   R   A
421   CAGTCTCCAGACTTT  CAGTCTGTGACTCCA  AAGGAGAGAGTCACC  ATCACCTGCCGGGCC
      GTCAGAGGTCTGAAA  GTCAGACACTGAGGT  TTCCTCTCTCAGTGG  TAGTGGACGGCCCGG

S   Q   T   I   G    N   N   L   H   W    Y   Q   Q   K   P    G   Q   S   P   K
481   AGTCAGACCATTGGT  AATAACTTACACTGG  TACCAGCAGAAACCA  GGTCAGTCTCCAAAG
      TCAGTCTGGTAACCA  TTATTGAATGTGACC  ATGGTCGTCTTTGGT  CCAGTCAGAGGTTTC

L   L   I   K   F    A   S   Q   S   F    S   G   V   P   S    R   F   S   G   S
541   CTCCTCATCAAGTTT  GCTTCCCAGTCCTTC  TCAGGGGTCCCCTCG  AGGTTCAGTGGCAGT
      GAGGAGTAGTTCAAA  CGAAGGGTCAGGAAG  AGTCCCCAGGGGAGC  TCCAAGTCACCGTCA

G   S   G   T   D    F   T   L   T   I    N   S   L   E   A    E   D   A   A   T
601   GGATCTGGGACAGAT  TTCACCCTCACCATC  AATAGCCTGGAAGCT  GAAGATGCTGCAACT
      CCTAGACCCTGTCTA  AAGTGGGAGTGGTAG  TTATCGGACCTTCGA  CTTCTACGACGTTGA

Y   Y   C   Q   Q    S   Y   S   T   P    W   T   F   G   Q    G   T   K   V   E
661   TATTACTGTCAACAG  AGTTACAGTACCCCG  TGGACGTTCGGCCAA  GGGACCAAGGTGGAA
      ATAATGACAGTTGTC  TCAATGTCATGGGGC  ACCTGCAAGCCGGTT  CCCTGGTTCCACCTT

I   K
721   ATCAAA
      TAGTTT
```

Fig. 30

C32oN-46

```
            E   L   Q   L   V     E   Q   S   G   A     A   L   V   K   P     G   D   S   V   K
  1     GAGCTGCAGCTGGTC   GAGCAGTCTGGAGCT   GCACTGGTGAAGCCT   GGGGACTCTGTGAAG
        CTCGACGTCGACCAG   CTCGTCAGACCTCGA   CGTGACCACTTCGGA   CCCCTGAGACACTTC

M   S   C   K   A     S   G   Y   P   F     T   D   Y   I   V     H   W   V   K   Q
 61     ATGTCTTGCAAAGCT   TCTGGTTATCCATTC   ACTGACTATATTGTA   CACTGGGTGAAGCAG
        TACAGAACGTTTCGA   AGACCAATAGGTAAG   TGACTGATATAACAT   GTGACCCACTTCGTC

S   H   G   K   S     L   D   W   I   G     Y   I   N   P   Y     S   G   D   T   K
121     AGTCATGGAAAGAGC   CTTGACTGGATTGGT   TATATTAATCCTTAC   AGTGGTGATACTAAG
        TCAGTACCTTTCTCG   GAACTGACCTAACCA   ATATAATTAGGAATG   TCACCACTATGATTC

F   N   E   K   F     K   S   K   A   T     L   T   V   D   K     S   S   S   T   A
181     TTCAATGAAAAGTTC   AAGAGTAAGGCCACG   TTGACTGTTGACAAG   TCCAGCAGCACAGCC
        AAGTTACTTTTCAAG   TTCTCATTCCGGTGC   AACTGACAACTGTTC   AGGTCGTCGTGTCGG

Y   M   E   F   S     R   L   T   S   E     D   S   A   I   Y     Y   C   A   R   S
241     TATATGGAGTTTAGC   CGATTGACATCTGAG   GATTCTGCAATCTAT   TACTGTGCAAGATCG
        ATATACCTCAAATCG   GCTAACTGTAGACTC   CTAAGACGTTAGATA   ATGACACGTTCTAGC

G   L   I   A   V     Y   F   D   Y   W     G   Q   G   T   T     V   T   V   S   S
301     GGTCTGATAGCAGTC   TACTTTGATTACTGG   GGCCAAGGGACCACG   GTCACCGTCTCCTCA
        CCAGACTATCGTCAG   ATGAAACTAATGACC   CCGGTTCCCTGGTGC   CAGTGGCAGAGGAGT

G   G   G   G   S     G   G   G   G   S     G   G   G   G   S     E   L   V   L   T
361     GGTGGTGGTGGTTCT   GGCGGCGGCGGCTCC   GGTGGTGGTGGTTCT   GAGCTCGTGCTGACT
        CCACCACCACCAAGA   CCGCCGCCGCCGAGG   CCACCACCACCAAGA   CTCGAGCACGACTGA

Q   S   P   D   F     Q   S   V   T   P     K   E   K   V   T     I   T   C   R   A
421     CAGTCTCCAGACTTT   CAGTCTGTGACTCCA   AAGGAGAAAGTCACC   ATCACCTGCCGGGCC
        GTCAGAGGTCTGAAA   GTCAGACACTGAGGT   TTCCTCTTTCAGTGG   TAGTGGACGGCCCGG

S   Q   S   I   G     S   S   L   H   W     Y   Q   Q   K   P     D   Q   S   P   K
481     AGTCAGAGTATTGGT   AGTAGCTTACACTGG   TACCAGCAGAAACCA   GATCAGTCTCCAAAG
        TCAGTCTCATAACCA   TCATCGAATGTGACC   ATGGTCGTCTTTGGT   CTAGTCAGAGGTTTC

L   L   I   K   F     A   S   Q   S   L     S   G   V   P   S     R   F   S   G   S
541     CTCCTCATCAAGTTT   GCTTCCCAGTCCCTC   TCAGGGGTCCCATCA   AGGTTCAGTGGCAGT
        GAGGAGTAGTTCAAA   CGAAGGGTCAGGGAG   AGTCCCCAGGGTAGT   TCCAAGTCACCGTCA

G   S   G   T   D     F   T   L   T   I     S   S   L   Q   P     E   D   F   A   T
601     GGATCTGGGACAGAT   TTCACTCTCACCATC   AGCAGTCTGCAACCT   GAAGATTTTGCAACT
        CCTAGACCCTGTCTA   AAGTGAGAGTGGTAG   TCGTCAGACGTTGGA   CTTCTAAAACGTTGA

Y   Y   C   Q   Q     S   Y   S   T   P     P   T   F   G   Q     G   T   K   V   E
661     TACTACTGTCAACAG   AGTTACAGTACCCCT   CCAACGTTCGGCCAA   GGGACCAAGGTGGAA
        ATGATGACAGTTGTC   TCAATGTCATGGGGA   GGTTGCAAGCCGGTT   CCCTGGTTCCACCTT

I   K
721     ATCAAA
        TAGTTT
```

Fig. 31

C32oN-89

```
              E   L   Q   L   V     E   Q   S   G   A     A   L   V   K   P     G   D   S   V   K
  1    GAGCTGCAGCTGGTC  GAGCAGTCTGGAGCT  GCACTGGTGAAGCCT  GGGGACTCTGTGAAG
       CTCGACGTCGACCAG  CTCGTCAGACCTCGA  CGTGACCACTTCGGA  CCCCTGAGACACTTC

M   S   C   K   A     S   G   Y   P   F     T   D   Y   I   V     H   W   V   K   Q
 61    ATGTCTTGCAAAGCT  TCTGGTTATCCATTC  ACTGACTATATTGTA  CACTGGGTGAAGCAG
       TACAGAACGTTTCGA  AGACCAATAGGTAAG  TGACTGATATAACAT  GTGACCCACTTCGTC

S   H   G   K   S     L   D   W   I   G     Y   I   N   P   Y     S   G   D   T   K
121    AGTCATGGAAAGAGC  CTTGACTGGATTGGT  TATATTAATCCTTAC  AGTGGTGATACTAAG
       TCAGTACCTTTCTCG  GAACTGACCTAACCA  ATATAATTAGGAATG  TCACCACTATGATTC

F   N   E   K   F     K   S   K   A   T     L   T   V   D   K     S   S   S   T   A
181    TTCAATGAAAAGTTC  AAGAGTAAGGCCACG  TTGACTGTTGACAAG  TCCAGCAGCACAGCC
       AAGTTACTTTTCAAG  TTCTCATTCCGGTGC  AACTGACAACTGTTC  AGGTCGTCGTGTCGG

Y   M   E   F   S     R   L   T   S   E     D   S   A   I   Y     Y   C   A   R   S
241    TATATGGAGTTTAGC  CGATTGACATCTGAG  GATTCTGCAATCTAT  TACTGTGCAAGATCG
       ATATACCTCAAATCG  GCTAACTGTAGACTC  CTAAGACGTTAGATA  ATGACACGTTCTAGC

G   L   I   A   V     Y   F   D   Y   W     G   Q   G   T   T     V   T   V   S   S
301    GGTCTGATAGCAGTC  TACTTTGATTACTGG  GGCCAAGGGACCACG  GTCACCGTCTCCTCA
       CCAGACTATCGTCAG  ATGAAACTAATGACC  CCGGTTCCCTGGTGC  CAGTGGCAGAGGAGT

G   G   G   S     G   G   G   G   S     G   G   G   G   S     E   L   V   L   T
361    GGTGGTGGTGGTTCT  GGCGGCGGCGGCTCC  GGTGGTGGTGGTTCT  GAGCTCGTGTTGACG
       CCACCACCACCAAGA  CCGCCGCCGCCGAGG  CCACCACCACCAAGA  CTCGAGCACAACTGC

Q   S   P   S   S     L   S   A   S   V     G   D   R   V   T     I   T   C   R   A
421    CAGTCTCCATCCTCC  CTGTCTGCATCTGTA  GGAGACAGAGTCACC  ATCACTTGCCGGGCA
       GTCAGAGGTAGGAGG  GACAGACGTAGACAT  CCTCTGTCTCAGTGG  TAGTGAACGGCCCGT

S   Q   S   I   S     R   Y   L   N   W     Y   Q   Q   K   P     G   K   P   P   K
481    AGTCAGAGCATTAGC  AGGTATTTAAATTGG  TATCAACAAAAACCA  GGGAAACCCCCTAAG
       TCAGTCTCGTAATCG  TCCATAAATTTAACC  ATAGTTGTTTTTGGT  CCCTTTGGGGGATTC

L   L   I   F   V     A   S   N   L   Q     T   G   V   P   S     R   F   S   G   S
541    CTCCTGATCTTTGTT  GCATCCAATTTGCAA  ACTGGGGTCCCATCA  AGGTTCAGTGGCAGT
       GAGGACTAGAAACAA  CGTAGGTTAAACGTT  TGACCCCAGGGTAGT  TCCAAGTCACCGTCA

G   S   G   T   D     F   T   L   T   I     S   S   L   E   P     E   D   F   A   V
601    GGATCTGGGACAGAT  TTCACTCTCACCATC  AGCAGCCTAGAGCCT  GAAGATTTTGCAGTT
       CCTAGACCCTGTCTA  AAGTGAGAGTGGTAG  TCGTCGGATCTCGGA  CTTCTAAAACGTCAA

Y   Y   C   Q   Q     R   S   N   W   P     L   T   F   G   G     G   T   K   V   D
661    TATTACTGTCAGCAG  CGTAGCAACTGGCCC  CTCACTTTCGGCGGA  GGGACCAAAGTGGAT
       ATAATGACAGTCGTC  GCATCGTTGACCGGG  GAGTGAAAGCCGCCT  CCCTGGTTTCACCTA

I   K
721    ATCAAA
       TAGTTT
```

Fig. 32

C32oN-92

```
          E  L  Q  L  V   E  Q  S  G  A   L  V  K  P   G  D  S  V  K
  1   GAGCTGCAGCTGGTC GAGCAGTCTGGAGCT GCACTGGTGAAGCCT GGGGACTCTGTGAAG
      CTCGACGTCGACCAG CTCGTCAGACCTCGA CGTGACCACTTCGGA CCCCTGAGACACTTC

M  S  C  K  A   S  G  Y  P  F   T │D  Y  I  V   H│W  V  K  Q
 61   ATGTCTTGCAAAGCT TCTGGTTATCCATTC ACT GACTATATTGTA CAC TGGGTGAAGCAG
      TACAGAACGTTTCGA AGACCAATAGGTAAG TGA CTGATATAACAT GTG ACCCACTTCGTC

S  H  G  K  S   L  D  W  I  G  │Y  I  N  P  Y   S  G  D  T  K
121   AGTCATGGAAAGAGC CTTGACTGGATTGGT │TATATTAATCCTTAC AGTGGTGATACTAAG
      TCAGTACCTTTCTCG GAACTGACCTAACCA │ATATAATTAGGAATG TCACCACTATGATTC

F  N  E  K  F   K  S│K  A  T   L  T  V  D  K   S  S  S  T  A
181   TTCAATGAAAAGTTC AAGAGT AAGGCCACG TTGACTGTTGACAAG TCCAGCAGCACAGCC
      AAGTTACTTTTCAAG TTCTCA TTCCGGTGC AACTGACAACTGTTC AGGTCGTCGTGTCGG

Y  M  E  F  S   R  L  T  S  E   D  S  A  I  Y   C  A  R│S
241   TATATGGAGTTTAGC CGATTGACATCTGAG GATTCTGCAATCTAT TACTGTGCAAGA TCG
      ATATACCTCAAATCG GCTAACTGTAGACTC CTAAGACGTTAGATA ATGACACGTTCT AGC

│G  L  I  A  V   Y  F  D  Y│W   G  Q  G  T  T   V  T  V  S  S
301    GGTCTGATAGCAGTC TACTTTGATTAC TGG GGCCAAGGGACCACG GTCACCGTCTCCTCA
       CCAGACTATCGTCAG ATGAAACTAATG ACC CCGGTTCCCTGGTGC CAGTGGCAGAGGAGT

G  G  G  G  S   G  G  G  G  S   G  G  G  G  S   E  L  V  L  T
361   GGTGGTGGTGGTTCT GGCGGCGGCGGCTCC GGTGGTGGTGGTTCT GAGCTCGTGCTGACT
      CCACCACCACCAAGA CCGCCGCCGCCGAGG CCACCACCACCAAGA CTCGAGCACGACTGA

Q  S  P  D  F   Q  S  V  T  P   K  E  K  V  T   I  T  C│R  A
421   CAGTCTCCAGACTTT CAGTCTGTGACTCCA AAGGAGAAAGTCACC ATCACCTGC CGGGCC
      GTCAGAGGTCTGAAA GTCAGACACTGAGGT TTCCTCTTTCAGTGG TAGTGGACG GCCCGG

S  Q  S  I  G   S  S  L  H│W   Y  Q  Q  K  P   D  Q  S  P  K
481   AGTCAGAGCATTGGT AGTAGCTTACAC TGG TACCAGCAGAAACCA GATCAGTCTCCAAAG
      TCAGTCTCGTAACCA TCATCGAATGT ACC ATGGTCGTCTTTGGT CTAGTCAGAGGTTTC

L  L  I  K│F   A  S  Q  S  L   S│G  V  P  S   R  F  S  G  S
541   CTCCTCATCAAG TTT GCTTCCCAGTCCCTC TCA GGGGTCCCCTCG AGGTTCAGTGGCAGT
      GAGGAGTAGTTC AAA CGAAGGGTCAGGGAG AGT CCCCAGGGGAGC TCCAAGTCACCGTCA

G  S  G  T  D   F  A  L  T  I   N  S  L  E  A   E  D  A  A  T
601   GGATCTGGGACAGAT TTCGCCCTCACCATC AATAGCCTGGAAGCT GAAGATGCTGCAACC
      CCTAGACCCTGTCTA AAGCGGGAGTGGTAG TTATCGGACCTTCGA CTTCTACGACGTTGG

Y  Y  C│Q  Q   S  S  T  L  P   P  T│F  G  Q   G  T  K  L  E
661   TATTACTGT CAGCAG AGTAGTACTTTACCT CCCACT TTTGGCCAG GGGACCAAGCTGGAG
      ATAATGACA GTCGTC TCATCATGAAATGGA GGGTGA AAACCGGTC CCCTGGTTCGACCTC

I  K
721   ATCAAA
      TAGTTT
```

Fig. 33

C33oN-32

```
           E  L  Q  L  V    E  Q  S  G  A    L  V  K  P       G  D  S  V  K
  1    GAGCTGCAGCTGGTC GAGCAGTCTGGAGCT GCACTGGTGAAGCCT GGGGACTCTGTGAAG
       CTCGACGTCGACCAG CTCGTCAGACCTCGA CGTGACCACTTCGGA CCCCTGAGACACTTC

M  S  C  K  A    S  G  Y  P  F    T  D  Y  I  V    H  W  V  K  Q
 61    ATGTCTTGCAAAGCT TCTGGTTATCCATTC ACTGACTATATTGTA CACTGGGTGAAGCAG
       TACAGAACGTTTCGA AGACCAATAGGTAAG TGACTGATATAACAT GTGACCCACTTCGTC

S  H  G  K  S    L  D  W  I  G    Y  I  N  P  Y    S  G  D  T  K
121    AGTCATGGAAAGAGC CTTGACTGGATTGGT TATATTAATCCTTAC AGTGGTGATACTAAG
       TCAGTACCTTTCTCG GAACTGACCTAACCA ATATAATTAGGAATG TCACCACTATGATTC

F  N  E  K  F    K  S  K  A  T    L  T  V  D  K    S  S  S  T  A
181    TTCAATGAAAAGTTC AAGAGTAAGGCCACG TTGACTGTTGACAAG TCCAGCAGCACAGCC
       AAGTTACTTTTCAAG TTCTCATTCCGGTGC AACTGACAACTGTTC AGGTCGTCGTGTCGG

Y  M  E  F  S    R  L  T  S  E    D  S  A  I  Y    Y  C  A  R  S
241    TATATGGAGTTTAGC CGATTGACATCTGAG GATTCTGCAATCTAT TACTGTGCAAGATCG
       ATATACCTCAAATCG GCTAACTGTAGACTC CTAAGACGTTAGATA ATGACACGTTCTAGC

G  L  I  A  V    Y  F  D  Y    W  G  Q  G  T  T    V  T  V  S  S
301    GGTCTGATAGCAGTC TACTTTGATTACTGG GGCCAAGGGACCACG GTCACCGTCTCCTCA
       CCAGACTATCGTCAG ATGAAACTAATGACC CCGGTTCCCTGGTGC CAGTGGCAGAGGAGT

G  G  G  G  S    G  G  G  G  S    G  G  G  G  S    E  L  V  L  T
361    GGTGGTGGTGGTTCT GGCGGCGGCGGCTCC GGTGGTGGTGGTTCT GAGCTCGTGCTGACT
       CCACCACCACCAAGA CCGCCGCCGCCGAGG CCACCACCACCAAGA CTCGAGCACGACTGA

Q  S  P  E  F    Q  S  V  A  P    K  E  K  V  T    I  T  C  R  A
421    CAGTCTCCAGAGTTT CAGTCTGTGGCTCCA AAGGAGAAAGTCACC ATCACCTGCCGGGCC
       GTCAGAGGTCTCAAA GTCAGACACCGAGGT TTCCTCTTTCAGTGG TAGTGGACGGCCCGG

S  Q  S  I  G    S  S  L  H    W  Y  Q  Q  K  P    D  Q  S  P  K
481    AGTCAGAGCATTGGT AGTAGCTTACACTGG TACCAGCAGAAACCA GATCAGTCTCCAAAG
       TCAGTCTCGTAACCA TCATCGAATGTGACC ATGGTCGTCTTTGGT CTAGTCAGAGGTTTC

L  L  I  K    F  A  S  Q  S  F    S  G  V  P  S    R  F  G  G  S
541    CTCCTCATCAAGTTT GCTTCCCAGTCCTTC TCAGGGGTCCCCTCG AGGTTCGGTGGCAGT
       GAGGAGTAGTTCAAA CGAAGGGTCAGGAAG AGTCCCCAGGGGAGC TCCAAGCCACCGTCA

G  S  G  T  N    F  T  L  T  I    N  S  L  E  A    E  D  A  A  T
601    GGATCTGGGACAAAT TTCACCCTCACCATC AATAGCCTGGAAGCT GAAGATGCTGCAACC
       CCTAGACCCTGTTTA AAGTGGGAGTGGTAG TTATCGGACCTTCGA CTTCTACGACGTTGG

Y  Y  C    Q  Q  S  S  T  L  P    P  T    F  G  Q    G  T  K  L  E
661    TATTACTGTCAGCAG AGTAGTACCTTACCT CCCACTTTTGGCCAG GGGACCAAGCTGGAG
       ATAATGACAGTCGTC TCATCATGGAATGGA GGGTGAAAACCGGTC CCCTGGTTCGACCTC

I  K
721    ATCAAA
       TAGTTT
```

Fig. 34

C33oN-33

```
        E   L   Q   L   V     E   Q   S   G   A     A   L   V   K   P     G   D   S   V   K
  1   GAGCTGCAGCTGGTC   GAGCAGTCTGGAGCT   GCACTGGTGAAGCCT   GGGGACTCTGTGAAG
      CTCGACGTCGACCAG   CTCGTCAGACCTCGA   CGTGACCACTTCGGA   CCCCTGAGACACTTC

M   S   C   K   A     S   G   Y   P   F     T  |D   Y   I   V   H| W   V   K   Q
 61   ATGTCTTGCAAAGCT   TCTGGTTATCCATTC   ACT|GACTATATTGTA  CAC|TGGGTGAAGCAG
      TACAGAACGTTTCGA   AGACCAATAGGTAAG   TGA|CTGATATAACAT  GTG|ACCCACTTCGTC

S   H   G   K   S     L   D   W   I   G    |Y   I   N   P   Y     S   G   D   T   K
121   AGTCATGGAAAGAGC   CTTGACTGGATTGGT  |TATATTAATCCTTAC   AGTGGTGATACTAAG
      TCAGTACCTTTCTCG   GAACTGACCTAACCA  |ATATAATTAGGAATG   TCACCACTATGATTC

|F   N   E   K   F     K   S| K   T     L   T   V   D   K     S   S   S   T   A
181    |TTCAATGAAAAGTTC   AAGAGT|AAGGCCACG   TTGACTGTTGACAAG   TCCAGCAGCACAGCC
       |AAGTTACTTTTCAAG   TTCTCA|TTCCGGTGC   AACTGACAACTGTTC   AGGTCGTCGTGTCGG

Y   M   E   F   S     R   L   T   S   E     D   S   A   I   Y     Y   C   A   R |S
241   TATATGGAGTTTAGC   CGATTGACATCTGAG   GATTCTGCAATCTAT   TACTGTGCAAGA|TCG
      ATATACCTCAAATCG   GCTAACTGTAGACTC   CTAAGACGTTAGATA   ATGACACGTTCT|AGC

|G   L   I   A   V     Y   F   D   Y| W   G   Q   G   T   T     V   T   V   S   S
301    |GGTCTGATAGCAGTC   TACTTTGATTAC|TGG   GGCCAAGGGACCACG   GTCACCGTCTCCTCA
       |CCAGACTATCGTCAG   ATGAAACTAATG|ACC   CCGGTTCCCTGGTGC   CAGTGGCAGAGGAGT

G   G   G   G   S     G   G   G   G   S     G   G   G   G   S     E   L   V   L   T
361   GGTGGTGGTGGTTCT   GGCGGCGGCGGCTCC   GGTGGTGGTGGTTCT   GAGCTCGTGCTGACT
      CCACCACCACCAAGA   CCGCCGCCGCCGAGG   CCACCACCACCAAGA   CTCGAGCACGACTGA

Q   S   P   D   F     Q   S   V   T   P     K   E   K   V   T     I   T   C |R   A
421   CAGTCTCCAGACTTT   CAGTCTGTGACTCCA   AAGGAGAAAGTCACC   ATCACCTGC|CGGGCC
      GTCAGAGGTCTGAAA   GTCAGACACTGAGGT   TTCCTCTTTCAGTGG   TAGTGGACG|GCCCGG

|S   Q   S   I   G     S   S   L   H| W   Y   Q   Q   K   P     D   Q   S   P   K
481    |AGTCAGAGCATTGGT   AGTAGCTTACAC|TGG   TACCAGCAGAAACCA   GATCAGTCTCCAAAG
       |TCAGTCTCGTAACCA   TCATCGAATGTG|ACC   ATGGTCGTCTTTGGT   CTAGTCAGAGGTTTC

L   L   I   K |F   A   S   Q   S   L   S| G   V   P   S   R   F   S   G   S
541   CTCCTCATCAAG|TTT   GCTTCCCAGTCCCTC   TCA|GGGGTCCCCTCG   AGGTTCAGTGGCAGT
      GAGGAGTAGTTC|AAA   CGAAGGGTCAGGGAG   AGT|CCCCAGGGGAGC   TCCAAGTCACCGTCA

G   S   G   T   D     F   T   L   T   I     N   S   L   E   A     E   D   A   A   T
601   GGATCTGGGACAGAT   TTCACCCTCACCATC   AATAGCCTGGAAGCT   GAAGATGCTGCAACT
      CCTAGACCCTGTCTA   AAGTGGGAGTGGTAG   TTATCGGACCTTCGA   CTTCTACGACGTTGA

Y   Y   C |Q   Q   S   Y   S   T   P   S   T| F   G   P   G   T   K   V   E
661   TACTACTGT|CAACAG   AGTTACAGTACCCCT   AGTACT|TTCGGCCCT   GGGACCAAGGTGGAG
      ATGATGACA|GTTGTC   TCAATGTCATGGGGA   TCATGA|AAGCCGGGA   CCCTGGTTCCACCTC

I   K
721   ATCAAA
      TAGTTT
```

Fig. 35

C33oN-49

```
         E   L   Q   L   V     E   Q   S   G   A     A   L   V   K   P     G   D   S   V   K
  1    GAGCTGCAGCTGGTC   GAGCAGTCTGGAGCT   GCACTGGTGAAGCCT   GGGGACTCTGTGAAG
       CTCGACGTCGACCAG   CTCGTCAGACCTCGA   CGTGACCACTTCGGA   CCCCTGAGACACTTC

M   S   C   K   A     S   G   Y   P   F     T   D   Y   I   V     H   W   V   K   Q
  61   ATGTCTTGCAAAGCT   TCTGGTTATCCATTC   ACTGACTATATTGTA   CACTGGGTGAAGCAG
       TACAGAACGTTTCGA   AGACCAATAGGTAAG   TGACTGATATAACAT   GTGACCCACTTCGTC

S   H   G   K   S     L   D   W   I   G     Y   I   N   P   Y     S   G   D   T   K
 121   AGTCATGGAAAGAGC   CTTGACTGGATTGGT   TATATTAATCCTTAC   AGTGGTGATACTAAG
       TCAGTACCTTTCTCG   GAACTGACCTAACCA   ATATAATTAGGAATG   TCACCACTATGATTC

F   N   E   K   F     K   S   K   A   T     L   T   V   D   K     S   S   S   T   A
 181   TTCAATGAAAAGTTC   AAGAGTAAGGCCACG   TTGACTGTTGACAAG   TCCAGCAGCACAGCC
       AAGTTACTTTTCAAG   TTCTCATTCCGGTGC   AACTGACAACTGTTC   AGGTCGTCGTGTCGG

Y   M   E   F   S     R   L   T   S   E     D   S   A   I   Y     Y   C   A   R   S
 241   TATATGGAGTTTAGC   CGATTGACATCTGAG   GATTCTGCAATCTAT   TACTGTGCAAGATCG
       ATATACCTCAAATCG   GCTAACTGTAGACTC   CTAAGACGTTAGATA   ATGACACGTTCTAGC

G   L   I   A   V     Y   F   D   Y   W     G   Q   G   T   T     V   T   V   S   S
 301   GGTCTGATAGCAGTC   TACTTTGATTACTGG   GGCCAAGGGACCACG   GTCACCGTCTCCTCA
       CCAGACTATCGTCAG   ATGAAACTAATGACC   CCGGTTCCCTGGTGC   CAGTGGCAGAGGAGT

G   G   G   G   S     G   G   G   G   S     G   G   G   G   S     E   L   V   L   T
 361   GGTGGTGGTGGTTCT   GGCGGCGGCGGCTCC   GGTGGTGGTGGTTCT   GAGCTCGTGCTGACT
       CCACCACCACCAAGA   CCGCCGCCGCCGAGG   CCACCACCACCAAGA   CTCGAGCACGACTGA

Q   S   P   D   F     Q   S   V   T   P     K   E   K   V   T     I   T   C   R   A
 421   CAGTCTCCAGACTTT   CAGTCTGTGACTCCA   AAGGAGAAAGTCACC   ATCACCTGCCGGGCC
       GTCAGAGGTCTGAAA   GTCAGACACTGAGGT   TTCCTCTTTCAGTGG   TAGTGGACGGCCCGG

S   Q   S   I   G     S   S   L   H   W     Y   Q   Q   K   P     D   Q   S   P   K
 481   AGTCAGAGCATTGGT   AGTAGCTTACACTGG   TACCAGCAGAAACCA   GATCAGTCTCCAAAG
       TCAGTCTCGTAACCA   TCATCGAATGTGACC   ATGGTCGTCTTTGGT   CTAGTCAGAGGTTTC

L   L   I   K   F     A   S   Q   S   F     S   G   V   P   S     R   F   S   G   S
 541   CTCCTCATCAAGTTT   GCTTCCCAGTCCTTC   TCAGGGGTCCCCTCG   AGGTTCAGTGGCAGT
       GAGGAGTAGTTCAAA   CGAAGGGTCAGGAAG   AGTCCCCAGGGGAGC   TCCAAGTCACCGTCA

G   S   G   T   D     F   T   L   T   I     N   S   L   E   A     E   D   A   A   T
 601   GGATCTGGGACAGAT   TTCACCCTCACCATC   AATAGCCTGGAAGCT   GAAGATGCTGCAACG
       CCTAGACCCTGTCTA   AAGTGGGAGTGGTAG   TTATCGGACCTTCGA   CTTCTACGACGTTGC

Y   Y   C   Q   Q     S   Y   S   T   P     W   T   F   G   Q     G   T   K   L   E
 661   TATTACTGTCAACAG   AGTTACAGTACCCCG   TGGACGTTCGGCCAA   GGGACCAAGCTGGAG
       ATAATGACAGTTGTC   TCAATGTCATGGGGC   ACCTGCAAGCCGGTT   CCCTGGTTCGACCTC

I   K
 721   ATCAAA
       TAGTTT
```

PREPARATION OF SCFV ANTIBODY FRAGMENTS

This application is a national phase application under 35 U.S.C. §371 of International Application No. PCT/EP 2005/004893 filed 4 May 2005, which claims priority to European Patent Application No.: EP 04 010 702.1 filed 5 May 2004. The entire text of each of the above-referenced disclosures is specifically incorporated herein by reference without disclaimer.

The invention relates to methods of preparing antibody fragments. Further, the invention relates to antibody fragments prepared by said methods. Further, the invention relates to antibody variable regions comprised in antibody fragments producible by said methods.

Antibody fragments offer many advantages over full immunoglobulin molecules when used as an active agent in a therapeutic regimen. For example, being of smaller size than their full size immunoglobulin counterparts, antibody fragments can achieve higher levels of tissue penetration when administered to a patient in need thereof, and therefore higher therapeutic efficacy than a larger immunoglobulin molecule of comparable antigen specificity. Further, due to this smaller size, antibody fragments are often more easily and economically producible than their full immunoglobulin counterparts of comparable antigen specificity. This is especially the case where the antibody is a single chain antibody fragment. A single chain antibody fragment is an antibody fragment which unifies at least one each of a variable region from the antibody heavy chain ("VH") and a variable region from the antibody light chain ("VL") into a single polypeptide chain, the respective VH and VL regions being separated by a peptide linker chosen so as to allow formation of a unified antigen binding site by complementarity determining regions ("CDRs") of the VH and VL domains. Finally, the modular construction of antibody fragments, comprising at least one VH and VL region, allows for a greater degree of flexibility in the design and construction of such fragments than possible for full immunoglobulin molecules, production of the latter often requiring the use of special cell lines to achieve the complex folding and, often, glycosylation patterns necessary for a desired biological activity.

The researcher seeking to develop antibody fragments useful in therapy will often already have access to a full immunoglobulin molecule of the desired specificity, either directly or via a suitable hybridoma cell line. Starting from such an immunoglobulin, he may make a corresponding antibody fragment comprising both the VH and VL regions of the "parent" immunoglobulin molecule. Such a corresponding antibody fragment may for example take the form of a Fab fragment, a (Fab)2 fragment, an scFv fragment (i.e. a single chain antibody ("SCA") unifying both VH and VL as part of a single polypeptide chain, as described above) or even a bivalent single chain antibody comprising two scFv fragments on a single polypeptide chain. In the latter case, the bivalent single chain antibody may comprise one scFv derived from the parent immunoglobulin molecule (bivalent bispecific single chain antibody), or two such scFvs (bivalent monospecific single chain antibody, or diabody).

However, it is often the case that direct conversion of a parent immunoglobulin molecule into an antibody fragment, that is to say, recombinant incorporation of the VH and VL regions comprised in one binding arm of the parent immunoglobulin molecule into a corresponding antibody fragment intended to have the same antigen binding specificity as the parent immunoglobulin molecule, leads to an antibody fragment which is not, or is not sufficiently expressible in soluble form. This problem is especially common when the corresponding antibody fragment is intended to be an scFv, regardless of whether this scFv is intended to be produced in monovalent form, or as part of a larger construct in bivalent form.

The inability to recombinantly express or sufficiently express such a corresponding antibody fragment in soluble form makes it impossible or, in the best case, much less feasible to exploit the advantages outlined above for antibody fragments in a contemplated regimen of therapy. In such a situation, the researcher seeking to develop antibody fragments useful in therapy is often left with the choice of either using the parent immunoglobulin antibody in full form or direct cleavage products thereof (e.g. Fab) as an active therapeutic agent, or finding or developing another full immunoglobulin with the desired specificity to use as a starting point for the construction of another corresponding antibody fragment which, he hopes, will not suffer the same problems as the first antibody fragment. The first scenario is unsatisfactory, since it implies accepting certain disadvantages associated with full immunoglobulin molecules which may not be in standing with the particular therapeutic regimen contemplated. The second scenario is unsatisfactory for several reasons. First, another immunoglobulin suitable for use as a new starting point for a new corresponding antibody fragment is not always available. Second, development of a new immunoglobulin with the desired antigen binding specificity can take a long time, and is in any case a costly undertaking, typically involving as it does the use of research animals from which a new hybridoma may be derived. Finally, even if another suitable immunoglobulin is already available, or another suitable immunoglobulin is developed, significant risk still remains that a corresponding antibody fragment resulting from such a new immunoglobulin will suffer the same problems of recombinant expressibility as experienced for the corresponding antibody fragment derived from the first immunoglobulin. In the case that no other immunoglobulin was available, and a new immunoglobulin had to be developed, such risk is especially acute, since the time and resources devoted to such development stand to be rendered worthless in retrospect.

There therefore exists a need for a method of preparing an antibody fragment from an immunoglobulin in cases where attempts at direct conversion of this immunoglobulin into an antibody fragment have failed. The aim of the invention is therefore to provide a method allowing such preparation.

Accordingly, a first aspect of the invention provides a method of preparing an antibody fragment of a source immunoglobulin, which source immunoglobulin specifically binds to an antigen of interest, a corresponding antibody fragment of which source immunoglobulin exhibits insufficient soluble recombinant expression, comprising:

(a) providing a nucleic acid molecule encoding a first antibody variable region or fragment thereof comprised in the source immunoglobulin, wherein the first antibody variable region or fragment thereof is a heavy chain variable region (VH) or a light chain variable region (VL), or a fragment of either of these;

(b) respectively combining (i) the nucleic acid molecule encoding the first antibody VH or VL region or fragment of either with (ii) a plurality of nucleic acid molecules encoding a diverse population of a second antibody variable region or fragment thereof, wherein the second antibody variable region or fragment thereof is a light chain variable region (VL) or a heavy chain variable region (VH), or a fragment of either of these, whereby a first population of combined nucleic acid molecules is obtained;

(c) introducing the first population of combined nucleic acid molecules into a display system chosen from a phage display system, a prokaryotic display system, a eukaryotic display system, or an mRNA display system;

(d) selecting at least one first antibody fragment displayed in step (c) and comprising the VH and VL region, or a fragment of either or both of these, which specifically binds to the antigen of interest; and (e) isolating the at least one first antibody fragment selected in step (d);

characterized in that the nucleic acid molecule encoding the first antibody variable region or fragment thereof or the nucleic acid molecule encoding the second antibody variable region or fragment thereof is operably linked to a nucleic acid molecule encoding an N-terminal, cis-acting amphipathic polypeptide moiety such that said N-terminal, cis-acting amphipathic polypeptide moiety, when translated, is linked to the N-terminal end of the first or second antibody variable region.

According to a preferred embodiment of the present invention, the nucleic acid molecule encoding the first antibody variable region or fragment thereof is obtained by PCR amplification of at least one polynucleotide comprised in a hybridoma cell or B cell which produces the source immunoglobulin; or peptide sequencing of at least one portion of the source immunoglobulin to determine the primary amino acid sequence of the at least one portion of the source immunoglobulin, followed by synthesis of a corresponding nucleic acid molecule capable of encoding the at least one portion of the source immunoglobulin sequenced.

According to another preferred embodiment of the present invention, the method of preparing an antibody fragment of a source immunoglobulin further comprises the following steps:

(a) respectively combining (i) the nucleic acid molecule encoding the second antibody variable region or fragment thereof with (ii) a plurality of nucleic acid molecules encoding a diverse population of a third antibody variable region or fragment thereof, wherein the third antibody variable region or fragment thereof is a heavy chain variable region (VH) or a light chain variable region (VL), or a fragment of either of these, whereby a second population of combined nucleic acid molecules is obtained;

(b) introducing the second population of combined nucleic acid molecules into a display system chosen from a phage display system, a prokaryotic display system, a eukaryotic display system, or an mRNA display system;

(c) selecting at least one second antibody fragment displayed in step (c) and comprising the VH and VL region, or a fragment of either or both of these, which specifically binds to the antigen of interest; and (d) isolating the at least one second antibody fragment selected in step (d);

characterized in that the nucleic acid molecule encoding the second antibody variable region or fragment thereof or the nucleic acid molecule encoding the third antibody variable region or fragment thereof is operably linked to a nucleic acid molecule encoding an N-terminal, cis-acting amphipathic polypeptide moiety such that said N-terminal, cis-acting amphipathic polypeptide moiety, when translated, is linked to the N-terminal end of the second or third antibody variable region.

Further preferred embodiments of the present invention are set out in the accompanying claims 3 and 5 to 15.

As used in the context of the present invention, the expressions "soluble expression" or "expressed in soluble form" or "expression in soluble form" or "solubly expressed" or other comparable expressions refer to a scenario in which an antibody fragment is expressed and/or secreted in a form allowing it to specifically bind to a desired antigen. One of skill in the art understands such a scenario as implying a native state of said antibody fragment in which the polypeptide chain/s of the antibody fragment is/are folded so as to allow the CDRs comprised within the VH and VL regions to spatially interact to form a single unified antigen binding site. Such folding is understood within the present invention as being stable enough such that the unified antigen binding site created by the mutual interaction of the CDRs persists under normal physiological conditions, i.e. the VH and VL regions do not continuously part and re-associate, but rather a single stable structure in which the VH and VL regions remain associated is formed. "Soluble expression" and other like terms such as those indicated above exclude the scenario in which the antibody fragment is expressed as inclusion bodies; such inclusion bodies are insoluble, and would require laborious refolding in order to render the antibody fragment capable of specifically binding to a desired antigen.

In the context of the present invention, the term "recombinant" encompasses all processes involving genetic sequences which are present in a form derived from, but not per se present in nature. For example, the incorporation of two genetic sequences encoding two discrete polypeptides individually found in nature into a new genetic sequence encoding a single protein not found in nature, said protein comprising each of these two discrete polypeptides, would be a "recombinant" process in the sense of the present invention. By the same token, the resulting protein comprising each of the two polypeptides mentioned above would be a "recombinant" protein, and its expression in a suitable host system, be it prokaryotic or eukaryotic, would be considered to be recombinant expression in the sense of the present invention.

As used in the context of the present invention, the terms "insufficient", "not sufficient" or other comparable terms refer in the context of soluble recombinant expression to the fact that said soluble recombinant expression (see above) being either absent or of such a low level as to render the conversion of a source immunoglobulin into a corresponding antibody fragment practically and/or economically unfeasible. Here it is noted that where soluble expression of a corresponding antibody fragment is unfeasible or of limited feasibility, such expression will generally also be of limited economic feasibility.

As used in the context of the present invention, the term "amphipathic polypeptide moiety" denotes a polypeptide having both hydrophobic and hydrophilic regions, each region being spatially defined and distinct from the other. One example of an "amphipathic polypeptide moiety" as used herein is a polypeptide comprising both hydrophilic and hydrophobic amino acids and in which, when the polypeptide forms a stable alpha-helix, the hydrophilic residues are spatially disposed on one side of the alpha helix, while the hydrophobic residues are spatially disposed on the other side of the alpha helix. Imagining such an alpha helix as an extended tube, then, the cross-section of this tube at any point would yield a circle, one hemisphere of which presents predominantly hydrophilic amino acid side chains to the outer environment, and the other hemisphere of which presents predominantly hydrophobic amino acid side chains to the outer environment. Another example of an "amphipathic polypeptide moiety" as used herein is a polypeptide beta sheet or even a globular polypeptide, one face of which presents predominantly hydrophilic amino acid side chains to the outer environment, and the other hemisphere of which presents predominantly hydrophobic amino acid side chains to the outer environment. An amphipathic polypeptide moiety may comprise one or more hydrophilic and/or hydrophobic regions, as described above.

As used in the context of the present invention, the term "operably associated" refers to a joining such that, upon translation of, e.g., a first and/or second antibody fragment, e.g., the amphipathic polypeptide moiety is also co-translated as part of the same polypeptide chain as, e.g., the first and/or second antibody variable region. Such joining should allow sufficient spatial degrees of freedom of the, e.g., amphipathic polypeptide moiety with respect to the, e.g., antibody fragment so as to allow spatial interaction between the former and the latter. Practically, this may be accomplished by interposing a polypeptide chain of sufficient length between the, e.g., amphipathic polypeptide moiety and, e.g., an antibody variable region to which it is attached such that the, e.g., amphipathic polypeptide moiety may "fold back" on the, e.g., antibody variable region and spatially interact with it.

The amphipathic polypeptide moiety is "N-terminal", meaning that it is located at the amino-terminus of the translated polypeptide. Since the amphipathic polypeptide moiety is located, N-terminally, on the same polypeptide chain as the first and second or, as the case may be, as the second and third antibody variable regions, it is able to interact with the variable region which is first translated in the translating step ("cis-acting"), in order to stabilize this region until the variable region which is second translated can complex with the first translated region, thereby possibly displacing the amphipathic polypeptide moiety, and forming a complex between the two antibody variable regions which remains stable and soluble even in the absence of the amphipathic polypeptide moiety.

As used in the context of the present invention, the expression "corresponding antibody fragment" refers to an antibody fragment which has been produced without the inventive method. As such, a "corresponding antibody fragment" will be the result of transferring, usually by recombinant technology, the VH and VL regions of the source immunoglobulin into a desired antibody fragment format. It is immaterial for the meaning of the expression "corresponding antibody fragment" as used according to the present invention what the format of the antibody fragment is; as long as the antibody fragment comprises both the VH and VL regions as they are each present in the source immunoglobulin, it is to be considered a "corresponding antibody fragment".

As used in the context of the present invention, the expression "source immunoglobulin" refers to any immunoglobulin molecule in full form, i.e. including Fc portion, but not necessarily including glycosylation decoration, which, when used as the starting point in making a corresponding antibody fragment, produces a corresponding antibody fragment which exhibits insufficient soluble recombinant expression (in the sense explained above). It follows, then, that an immunoglobulin used as a starting point in making a corresponding antibody fragment which does exhibit sufficient soluble expression (in the sense explained above) is not to be regarded as a "source immunoglobulin" within the sense of this term.

As used in the context of the present invention, the expression "antigen binding properties" refers to any parameter of an antibody fragment which is descriptive of the interaction of this antibody fragment with the antigen of interest. Such "antigen binding properties" may for example include, but are not limited to, the specificity of binding with respect to an antigen of choice and the strength of binding, i.e. binding affinity, with respect to this antigen.

As used in the context of the present invention, the term "complementary" refers to a state of mutual spatial and/or electrostatic compatibility between two antibody variable regions, for example between a VH and VL region, which allows and/or fosters stable formation of a complex between these two regions. As such, "complementary" antibody variable regions fit together in a spatial, three-dimensional sense, and this fitting may be promoted by specific and/or non-specific electrostatic interactions between the amino acid side chains of one antibody variable region with those of the other antibody variable region. The term "complementary" also encompasses the scenario in which the proper (i.e. naïve) three-dimensional folding of one respective antibody variable domain depends on the presence of another antibody variable domain, and vice-versa. This latter scenario is one in which the two antibody variable domains are "complementary," at least in part due to a mutual induction of fit.

Within the meaning of the invention, an antibody fragment is "selectable" when, after having been translated into a polypeptide from a corresponding nucleic acid molecule, the antibody fragment is rendered accessible from outside the system allowing correlation between genotype and phenotype such that the antigen binding properties of the antibody fragment can be ascertained in a qualitative or quantitative sense. If an antibody fragment is selectable, it has obviously been translated and recombinantly expressed in soluble form. As such, the requirement that the antibody fragment be "selectable" aims at determining which antibody fragment/s of the larger pool of antibody fragments which were recombinantly expressible in soluble form also bind to the antigen of interest, i.e. the antigen bound by the source immunoglobulin.

The method according to the invention provides an efficient and reliable way of recovering, in an antibody fragment, desired antigen binding properties hitherto observed in a source immunoglobulin, when standard efforts to convert this source immunoglobulin to a corresponding antibody fragment have failed. As such, the method according to the invention eliminates the dependency on full immunoglobulin molecules as active binding agents, e.g. of medicaments, where the use of antibody fragments of identical or comparable antigen specificity would be either desirable or necessary for a particular therapeutic application. By facilitating the production of alternate antibody-based binding agents, the method of the invention significantly expands the palette of antibody-based therapeutic agents open for use when treating a particular disease.

It has surprisingly been observed that by providing the amphipathic polypeptide moiety as defined above, the soluble recombinant expression of new combinations of antibody variable regions is promoted. A lack of recombinant solubility may arise for any number of reasons. For example, the polypeptide being expressed may contain predominantly hydrophobic amino acids, or at least bear such hydrophobic amino acids to the external hydrophilic environment. In another possible scenario, the charges of charged amino acids in contact with the aqueous (hydrophilic) environment may be neutralized by counterions in solution such that the charged amino acids are no longer able to interact hydrophilically with their environment, thereby leading to a decrease in overall polypeptide solubility (i.e. isoelectric precipitation). Without being bound by theory, the inventors believe that the amphipathic polypeptide moiety non-covalently associates with, say, a predominantly hydrophobic partner protein or with a predominantly hydrophobic region of a partner protein. Such association in effect "converts" the hydrophobic nature of the partner protein to a hydrophilic nature since, seen from the standpoint of the solution in the aqueous environment, the hydrophobic amino acid side chains of the partner protein have been replaced by the hydrophilic amino acid side chains in the amphipathic polypeptide moiety. In this way the aqueous solubility of a partner protein, for example a first or second antibody fragment as in the present method, is greatly enhanced by an effective chaperoning provided by the amphipathic polypeptide moiety. A similar effect of interaction between the amphipathic polypeptide moiety and regions of the partner protein/polypeptide is conceivable in the phenomenon of isoelectric precipitation mentioned above. In such a scenario, the amphipathic polypeptide moiety would likely displace any charge-neutralizing moieties from the outer surface of the partner polypeptide, thereby increasing the latter's solubility.

The inventors believe that such chaperoning may be important in the translation step of the present inventive method. Here, a translated first antibody variable region which alone may not be sufficiently recombinantly expressible in soluble form is kept—by virtue of the amphipathic polypeptide moiety—soluble long enough to form a complex with a complementary second antibody variable region. A complex of first and second complementary antibody variable regions then likely has sufficient solubility to exist in stably folded form in the absence of the amphipathic polypeptide moiety. In effect, then, the amphipathic polypeptide moiety chaperones an otherwise insoluble first antibody variable region to a second antibody variable region such that a complex of first and second antibody variable regions is formed which is also soluble in the absence of the amphipathic polypeptide moiety. In the absence of the amphipathic polypeptide moiety, such a complex would not likely have formed at all, and certainly would not have formed in the time available before the selecting step, since the first antibody variable region would not have sufficient solubility in aqueous solution to form a complex with the second antibody variable region.

Analogous reasoning may also be applied to chaperoning of an otherwise insoluble second antibody variable region prior to the latter's forming a complex with a first antibody variable region.

After a sufficiently soluble first and/or second antibody fragment has/ve been identified in the selection step of the inventive method, the amphipathic polypeptide moiety and any additional polypeptide linking the amphipathic polypeptide moiety to an antibody variable region may be removed, either at the polypeptide level (e.g. by incorporating a suitable protease cleavage site just outside the antibody variable region), or at the nucleotide level (e.g. by omitting the nucleic acid molecule encoding the amphipathic polypeptide moiety and any linking polypeptide in a nucleic acid molecule to be incorporated into a vector for separate recombinant expression).

According to an embodiment of the present method, amphipathic polypeptide moieties suitable for this purpose may be chosen from the pro regions of any of the following polypeptides: papain, cruzain, thermolysin, cathepsin B, cathepsin L, protease A, protease B, IgA protease and carboxypeptidase Y; the N2 domain of filamentous phage (e.g. M13); or any polypeptide moiety which comprises an amphipathic region as determined by the publicly available internet program available from the German Cancer Research Center at, the world-wide-web dkfz-heidelberg.de/tbi/bioinfo/Individual/HelicalWheel/.

According to an embodiment of the present method, amphipathic polypeptide moieties suitable for this purpose may be chosen from the pro regions of any of the following polypeptides: papain, cruzain, thermolysin, cathepsin B, cathepsin L, protease A, protease B, IgA protease and carboxypeptidase Y; the N2 domain of filamentous phage (e.g. M13); or any polypeptide moiety which comprises an amphipathic region as determined by the publicly available internet program at www.dkfz-heidelberg.de/tbi/bioinfo/Individual/HelicalWheel/.

It should be noted that the provision of a nucleic acid molecule encoding the first antibody variable region may be effected by any number of methods. In principle, any method which allows conversion of the primary amino acid sequence of the first antibody variable region into a base sequence of a nucleic acid molecule which, when translated, will result in the primary amino acid sequence of the first antibody variable domain, is acceptable and within the scope of the invention as a way of "providing a nucleic acid molecule encoding a first antibody variable domain". One way of providing a nucleic acid molecule encoding a first antibody variable region may be by PCR amplification of at least one polynucleotide comprised in an immortalized hybridoma cell which produces the source immunoglobulin, for example PCR amplification of an mRNA molecule encoding a first antibody variable region. Another way may be by PCR amplification of at least one polynucleotide comprised in a non-immortalized lymphocyte in or isolated from a blood sample, said lymphocyte producing the source immunoglobulin.

Another way of "providing a nucleic acid molecule encoding a first antibody variable domain" is by direct peptide sequencing of at least a portion of the source immunoglobulin to determine a primary amino acid sequence. From this primary amino acid sequence, it is possible to construct at least one nucleic acid molecule which, when translated, results in the amino acid sequence of the first antibody variable domain. This way of providing a nucleic acid molecule encoding a first antibody variable domain has the advantage of great flexibility in construction of a nucleic acid molecule. Due to the degeneracy of the genetic code, there will exist a large number of possible nucleic acid molecules which, when translated, will lead to the primary sequence of the first antibody variable domain. For each amino acid in the first antibody variable region for which there exists more than one codon, there also exists the possibility of optimizing the codon chosen. For example, it may be that of several potential codons, one is known to be most the common codon for the amino acid in question in the particular expression system to be used later in the inventive method. Choosing at this position this most commonly used codon, and then repeating the same process for each of the degenerate codons encountered in the sequence of the first antibody variable region therefore leads to a nucleic acid molecule which, when translated in the system of choice later in the method, is likely to lead to the highest expression levels. In this way, an optimization of expression profile in the system of choice is achieved.

Alternatively, a slowing down of the translation process may be desirable in some circumstances, for example to allow the emerging protein or polypeptide chain time to properly fold. Here, it is within the ambit of the invention to choose codons such that the speed of translation is reduced to allow this effect. One of ordinary skill in the art understands how to manipulate codon usage to achieve such effects.

The above method of direct peptide sequencing followed by construction of a suitable nucleic acid molecule would lead to a polypeptide which is identical to the first antibody variable region. It should also be appreciated, however, that the nucleic acid molecule obtained in this manner need not necessarily lead to a polypeptide exhibiting a sequence which is identical to that of the first antibody variable region comprised in the source immunoglobulin. It is also possible to effect changes in the individual codons of the resulting nucleotide acid sequence such that the polypeptide is more suitable for use as a therapeutic agent. For example, the primary amino acid sequence of the first antibody variable region may be evaluated by known methods for determining the presence of potential T cell epitopes (for example as described in WO 92/10755, WO 00/34317, WO 98/52976, WO 02/079415, WO 02/012899 and WO 02/069232) which, if left unchanged in the first antibody variable region, would likely trigger an immunogenic response in the body of a patient to whom the resulting antibody fragment has been administered. Should T cell epitopes be found to exist, amino acid mutations may be performed at the nucleic acid level to eliminate or at least reduce the presence of such T cell epitopes in the finally translated polypeptide molecule. Such mutations will likely be of a conservative nature, i.e. will be of the sort which retains to as great an extent as possible the chemical characteristics (e.g. molecular weight, molecular shape, electronegativity, electrostatic charge, etc.) of the amino acid side chain, so as to perturb the folding of the first antibody variable region as little as possible in the final antibody fragment (i.e. in the "first antibody fragment").

In general, then, de novo amino acid sequencing may allow the researcher a great deal of freedom to tailor the nucleic acid molecule at the most fundamental level so as to fulfil the various requirements set upon the antibody fragment finally obtained.

As stated above, the inventive method may advantageously be used to render expressible an antibody fragment derived from a source immunoglobulin, where the corresponding antibody fragment derived directly from the source immunoglobulin was previously not at all recombinantly expressible in soluble form (i.e. expression which is under the detection limit using standard detection methods, for example ELISA). However, the teaching of the inventive method can also be employed to enhance the soluble recombinant expressibility of an antibody fragment derived from a source immunoglobulin in the event that the corresponding antibody fragment derived directly from the source immunoglobulin was previously recombinantly expressible in soluble form, but only poorly so.

Accordingly, one embodiment of the invention provides the additional steps of evaluating the ability of the isolated first antibody fragment to be recombinantly expressed in soluble form, and isolating at least one first antibody fragment, the soluble recombinant expression properties of which have been improved relative to those of said corresponding antibody fragment. As such, the method of the invention as described above allows an improvement in the recombinant expressibility of an antibody fragment derived from a source immunoglobulin (i.e. non-expressible antibody fragment rendered expressible, or poorly expressible antibody fragment rendered more expressible).

One of ordinary skill in the art understands how to evaluate the soluble recombinant expressibility of polypeptides such as the isolated first antibody fragment, the primary indicator of recombinant expressibility being the yield of said first antibody fragment in a recombinant expression system identical to that used to express a corresponding antibody fragment directly derived from the source immunoglobulin. Comparative yields may be measured by known methods, for example SDS-PAGE, Western blot, antigen binding ELISA, BIAcore and/or spectroscopic methods ($OD_{280}$). Alternatively, a functional readout may be used in evaluating the soluble recombinant expressibility of a first antibody fragment as compared to that of a corresponding antibody fragment. Such functional readouts may for example be antibody fragment binding (e.g. ELISA, immunoblot, BIAcore, FACS analysis, isothermal titration calorimetry (ITC), fluorescent correlation spectroscopy (FCS) and/or Scatchard analysis), neutralization (e.g. competitive binding assays, inhibition of cell proliferation or inhibition of signal transduction) and/or FACS analysis.

Whether or not the isolated first antibody fragment represents a qualitative or a quantitative improvement in the soluble recombinant expressibility of a corresponding antibody fragment, this first antibody fragment comprises a first antibody variable region identical to or, in the event that mutations have been made at the nucleic acid level following peptide sequencing of at least a portion of the source immunoglobulin as described above, derived from a variable region of the source immunoglobulin as well as a complementary second antibody variable region originating from the plurality of nucleic acid molecules. So one variable region comprised in the first antibody fragment originates from the source immunoglobulin, while the other variable region originates from elsewhere, i.e. from a source of the researcher's choice. Ideally, this source may be a diverse library of different antibody variable domains obtained, for example, from blood cells, for example human blood cells.

A further embodiment of the method according to the invention entails an iterative application of the method. In a first round (described above) the first antibody variable region is held constant while being randomly combined, at the nucleic acid level, with many different potential nucleic acid molecules encoding a second antibody variable region. The present embodiment provides a second round in which now the second antibody variable region present in the first antibody fragment (the first antibody fragment being derived in the first iterative round) is held constant and is randomly combined, at the nucleic acid level, with many different potential nucleic acid molecules encoding a third antibody variable region complementary to the second antibody variable region. The plurality of nucleic acid molecules encoding a third antibody variable region may be for example a diverse library of different antibody variable domains obtained, for example, from blood cells, for example human blood cells.

As such, the second antibody fragment isolated after the second iterative round described according to the present embodiment will not comprise a first antibody variable region from the source immunoglobulin, since the first antibody variable region will have been replaced in the second iterative round of the method by the third antibody variable region. This embodiment has the advantage that the natures (i.e. origins) of the second and third antibody variable chains comprised in the second antibody fragment may be tuned as desired by choosing the natures (i.e. origins) of the plurality of nucleic acid molecules encoding diverse populations of second and third antibody variable regions used in the first and second iterative rounds, respectively. In this way, the present embodiment of the inventive method may be used to optimize the immunogenic potential of a second antibody fragment intended for use in a particular patient species. Specifically, in the event that the second antibody fragment is intended for eventual use in a human patient, the pluralities of nucleic acid molecules encoding diverse populations of second and third antibody variable regions used in, respectively, the first and second iterative rounds of the method may each be of human origin. In this way, the second antibody fragment obtained is not only one in which the soluble recombinant expressibility of the second antibody fragment has been made possible or enhanced, but also one which comprises only sequences which will be least likely to elicit an unwanted host immune response when administered to a human patient. Similar considerations may be applied to the preparation of second antibody fragments intended for use in veterinary applications, for example as therapeutic agents for primate, feline, canine, equine, fish, bird, or tylopod subjects.

A further embodiment of the method of the invention provides the additional steps of evaluating the ability of the isolated second antibody fragment to be recombinantly expressed in soluble form, and isolating at least one second antibody fragment, the expression and general properties (physical, biophysical, chemical properties) of which have been improved relative. to those of a corresponding antibody fragment or relative to the isolated first antibody fragment. This embodiment is analogous to the embodiment discussed above as optionally following a first iterative round of the inventive method and has the advantage that it is possible to achieve a quantitative enhancement of the soluble recombinant expressibility of the isolated second antibody fragment relative to the isolated first antibody fragment and/or the corresponding antibody fragment produced directly from the source immunoglobulin.

According to a further embodiment of the method of the invention, the nucleic acid molecules encoding the first and the second antibody variable regions or fragments thereof making up the first population of combined nucleic acid molecules; and/or the nucleic acid molecules encoding the second and the third antibody variable regions or fragments thereof making up the second population of combined nucleic acid molecules are introduced into said system as a single continuous nucleic acid molecule or as two discrete nucleic acid molecules. Introduction of said sequences into said system as a single contiguous nucleic acid molecule will result, when this single contiguous nucleic acid molecule is translated, in a single polypeptide chain. This single polypeptide chain may comprise both a VH and VL region, i.e. may be a single chain antibody in which the VH and VL regions are disposed, for example via a suitable polypeptide linker, so as to allow association between complementary VH and VL polypeptides. Introduction of said molecules into said system as two discrete nucleic acid molecules will result, when these molecules are translated, in two discrete polypeptide chains. In this latter case, the nature of the system allowing correlation between the genotype of a member of the first or second population of combined nucleic acid molecules with the phenotype of a respective first or second antibody fragment must be such as to allow covalent or non-covalent association of the first with the second antibody variable region or, as the case may be, of the second with the third antibody variable region.

This embodiment of the method of the invention has the advantage that in rendering an antibody fragment recombinantly expressible in soluble form (or enhancing its recombinant expressibility in soluble form), the researcher is not limited to a specific antibody format. Starting from a source immunoglobulin, the researcher might choose to create both the first and second antibody fragments in the form of a single chain antibody, or he might choose first to create a Fab-like construct (i.e. a Fab or (Fab')2 fragment) as the first antibody fragment before converting it to a single chain (i.e. scFv format) in the second antibody fragment. The researcher is also free to perform only the first iteration of the method, in which case he might choose to convert a source immunoglobulin into either a solubly expressible scFv or Fab format.

In an especially preferred embodiment of the method of the invention, the first or first and second antibody fragments are prepared as scFv antibody fragments. According to this especially preferred embodiment, then, soluble recombinant expressibility of an antibody fragment derived from a source immunoglobulin is made possible or enhanced in the form of an scFv antibody fragment.

According to a further embodiment of the inventive method, the system allowing correlation of the genotype of the first or second population of combined nucleic acid molecules with the phenotype of, respectively, a first or second antibody fragment may be a phage display system, a ribosome display system, a display system involving eukaryotic cells, a display system involving prokaryotic cells, a system for intracellular selection, covalent display, puromycin display, Cys-display or mRNA display. Of these systems, a phage display system is especially preferred due to its established nature and ease of performance for the skilled practitioner. According to a further embodiment, the display system involving prokaryotic cells is a E. coli display method. The skilled person is well acquainted with the above display systems and thus knows that an mRNA display system is unsuitable for use in the event that an antibody fragment comprising two or more distinct polypeptide chains is to be produced. This renders any kind of mRNA display unsuitable for use in the present invention for production of i.a. a Fab antibody fragment or a (Fab)2 antibody fragment.

The system should be employed, and the first or second population of combined nucleic acid molecules incorporated into this system such that the first or first and second antibody fragment, when translated within the system, become/s selectable. Selection occurs according to two criteria: (a) the antibody fragment must have been recombinantly expressed in soluble form and (b) the antibody fragment must bind to the antigen of interest. If criterion (b) is fulfilled, then criterion (a) is necessarily present as well; an antibody fragment which is selectable has also been recombinantly expressed in soluble form. For the purposes of the present embodiment of the invention, it is advantageous to fashion the first population or first and second populations of nucleic acid molecules such that, when translated in said system, the portion of the resulting antibody fragment responsible for specifically binding to an antigen of interest, i.e. the CDRs of the first and second antibody variable regions or of the second and third antibody variable regions, are accessible from outside said system, e.g. by an antigen of interest outside the system. For example, in the event that a phage display system is employed, it is advantageous to fashion the point of connection of the antibody fragment to be selected to the outer coat protein of the phage particle such that the CDRs of the first and second antibody variable regions or, as the case may be, of the second and third antibody variable regions are directed away from the phage particle. This may for example be achieved when introducing the first or second population of combined nucleic acid molecules by covalently anchoring the antibody fragment to a phage coat protein, for example cpIII or cpVIII of a filamentous phage particle, for example via a peptidic linkage located in the antibody fragment at a position distal to the CDRs. In this way, the antibody fragment remains anchored to its phage particle, without the point of anchoring interfering with the ability of the antibody fragment to specifically bind to an antigen of interest. So once such an antibody fragment has been translated and recombinantly expressed in soluble form, it will also remain selectable with respect to its ability to specifically bind to an antigen of interest.

According to a further embodiment, the nucleic acid molecules encoding the first, second and/or third antibody variable regions or fragments thereof are derived from the same or different species. The benefits of varying the species of origin of the antibody variable regions or fragments thereof in terms of the nature of the final antibody fragment product obtained have been explained above. In particular, it should be noted that the ability to independently vary the origin of the antibody variable regions obtained allows the researcher to align the species of origin of these antibody variable regions with the species for which treatment of a disease is contemplated using an antibody fragment prepared by methods described herein. In this way, decoupling the origin of the final antibody fragment obtained from the origin of the source immunoglobulin allows alignment of the origin of the antibody fragment with the species intended for treatment so as to minimize any potential unwanted immunogenic side effects following administration.

According to an especially preferred embodiment, the source immunoglobulin and the nucleic acid molecule encoding the first antibody variable region or fragment thereof may be of non-human origin, and the nucleic acid molecule encoding the second and/or third antibody variable region or fragment thereof may be of human origin, or at least 85%, 90% or 95% of the nucleic acid molecule are of human origin. Preferably, one CDR such as CDR1, CDR2, or CDR3, the latter being especially preferred, is of non-human origin, the remainder of the CDRs being human. An important advantage of this embodiment is that immunoglobulin molecules of non-human origin for which, up to now, conversion into a corresponding antibody fragment has been impossible or unfeasible may now be converted into corresponding antibody fragments. At the same time, the resulting antibody fragments may be optimized for administration to a human subject. In this way, the researcher now has access to the formidable diversity of available, non-human immunoglobulin molecules as antibody fragments in therapeutically relevant form.

In a further particularly preferred embodiment, the source immunoglobulin and the nucleic acid molecule encoding the first antibody variable region or fragment thereof are of rodent origin, preferably of murine or rat origin. This is advantageous since the majority of immunoglobulin molecules or hybridoma cell lines available are of rodent, especially of murine or rat origin. This opens significant avenues for the preparation of antibody fragments of partly or completely human origin starting from any of the multitude of commercially available immunoglobulin molecules or hybridoma cell lines of rodent (e.g. murine or rat) origin.

According to a further embodiment of the invention, the first, second and third antibody variable regions or fragments thereof may independently be a VH region or a fragment thereof, or a VL region or a fragment thereof. It is therefore irrelevant whether the first antibody variable region derived from the source immunoglobulin is a VH or a VL region. Given the high degree of mutual compatibility between VH and VL regions, two scenarios immediately arise in this context. In the first scenario, the first antibody variable region or fragment thereof is a VH region or fragment thereof. In this case, an antibody variable region complementary for the first antibody variable region will most likely be a VL region and, if a further iterative round of the method is performed as described above, a third antibody variable region complementary to the second antibody variable region will be a VH region. In the second, converse scenario, if the first antibody variable region or fragment thereof is a VL region or fragment thereof, the second antibody variable region or fragment thereof will likely be a VH region and any third antibody variable region or fragment thereof will likely be a VL region. Generally, therefore, given that a VH region will most likely pair with a complementary VL region and a VL region will most likely pair with a complementary VH region, the choice of the first antibody variable region as a VH or VL region is very likely to be sufficient to determine the identity of the second antibody variable region and any third antibody variable region in the final antibody fragment product(s).

It should be noted, however, that it is within the ambit of this embodiment of the invention that a VH region may be complementary to another VH region, or that a VL region may be complementary to another VL region. In this case, the choice of the first antibody variable region as VH or VL region need not determine the identity of the second and third antibody variable regions. As a result, it is not excluded from the ambit of this embodiment of the invention that the first or first and second antibody fragments obtained as products of the methods described herein comprise two VH regions or two VL regions, the main criteria for selection of such antibody fragments being that the antibody fragment product is both recombinantly expressible, or sufficiently recombinantly expressible in soluble form and specifically binds to the antigen of interest, the antigen of interest being the same antigen as that bound by the source immunoglobulin.

A further aspect of the invention provides a first antibody fragment obtainable by the methods described in the foregoing. This first antibody fragment may advantageously be in the form of an scFv fragment or a Fab fragment. The first antibody fragment has the advantage that it is expressible in soluble form and specifically binds the same antigen as the source immunoglobulin, whereas a corresponding antibody fragment, i.e. an antibody fragment converted directly from the source immunoglobulin without first performing the inventive method, would not have been obtainable, either at all or in sufficient amount in soluble form. Seen this way, the first antibody fragment represents a molecular species in which the antigen binding properties of the source immunoglobulin have been "rescued" in the form of an antibody fragment.

As described above, the first antibody fragment will comprise the first antibody variable region derived from the source immunoglobulin. According to one embodiment of this aspect of the invention, the first antibody variable region comprised in the first antibody fragment is present in modified form as compared to the form in which it is comprised in the source immunoglobulin. Modification may advantageously take place at the nucleotide level, for example prior to combination of the nucleic acid molecule encoding the first antibody variable region with a plurality of nucleic acid molecules encoding a diverse population of a second antibody variable region complementary to the first antibody variable region. According to an especially preferred embodiment, the first antibody variable region is modified so as to render it less likely to elicit a host immune response when administered to a subject as a therapeutic agent. Such modifications may for example include humanization (i.e. CDR-grafting or modification to correspond to a close human germline sequence, for example as described in WO 91/09968 and U.S. Pat. No. 6,407,213) and/or deimmunization of the first antibody variable region (for example as described in WO 92/10755, WO 00/34317, WO 98/52976, WO 02/079415, WO 02/012899 and WO 02/069232). When the second antibody variable region comprised in the first antibody fragment is chosen to be of human origin, but the source immunoglobulin—and hence the first antibody variable region—is of non-human origin, humanization and/or deimmunization (the latter taking into account known human T cell epitopes) of the first antibody variable region results in a first antibody fragment which is very unlikely to elicit an immunogenic response when introduced into a human patient.

According to another exemplary embodiment of this aspect of the invention, the first antibody fragment comprises a region exhibiting the amino acid sequence as set out in SEQ ID NO: 1, or a modified version of SEQ ID NO: 1 ("modified" is to be understood as within the meaning as set out in the preceding paragraph). SEQ ID NO: 1 represents the VH of a hybridoma-derived immunoglobulin which specifically binds to human granulocyte macrophage colony stimulating factor (GM-CSF). As a full immunoglobulin molecule with an Fc portion, this may not be suitable for implementation as a therapeutic agent. However, direct incorporation of the VH and VL regions of this immunoglobulin into, for example, a corresponding scFv fragment yields a molecular species which is not expressible in soluble form (i.e. the immunoglobulin qualifies as a "source immunoglobulin" as defined hereinabove). Only by performing at least one round of the method as described hereinabove is an scFv obtainable in soluble form which also demonstrated the same binding characteristics (i.e. anti-GM-CSF) as the source immunoglobulin. As such, the method as disclosed hereinabove allows the "rescue" of the antigen binding properties of the anti-GM-CSF source immunoglobulin in the form of an scFv comprising the VH of the source immunoglobulin, said scFv being more suitable for use for many kinds of therapy than the source immunoglobulin. As indicated above, the skilled person will readily recognize that the source immunoglobulin and the antibody fragments having anti GM-CSF specificity, which are described in great detail in the examples, represent just one antibody (specificity) and that the method of the present invention is likewise useful for the preparation of any other antibody fragments of specificity other than for (human) GM-CSF, regardless of what this other binding specificity might be. As such, the inventive method represents a method of general applicability for converting any source immunoglobulin (specific for any antigen) to an antibody fragment having the same specificity as said source immunoglobulin, where previous attempts at such conversion by simple transfer of e.g. the variable regions of said source immunoglobulin into a desired antibody fragment have resulted in an antibody fragment which is not recombinantly, solubly expressible. The GM-CSF antigen as described in the appended examples is thus merely illustrative of the method's functionality, and is not to be interpreted as in any way restrictive to the term "antigen of interest".

Modification of SEQ ID NO: 1 within the first antibody fragment as outlined above in order to render the molecule less likely to elicit an immune response when introduced into a subject, especially a human subject, is within the ambit of this embodiment.

A further aspect of the invention provides a first or second antibody variable region or fragment thereof, as derived from the first antibody fragment obtained by the methodology described hereinabove. In a preferred embodiment, the second antibody variable region is a VL, especially preferred a VL comprising a region exhibiting any VL amino acid sequence as shown in any of FIGS. 11-35.

Further aspects of the invention in this context provide a polypeptide comprising the VL region as shown in any of FIGS. 11-35, any nucleic acid molecule encoding such a polypeptide, and any nucleic acid molecules hybridizing with the nucleic acid molecule encoding such a polypeptide under stringent conditions (for example as described in Sambrook, Cold Spring Harbor Laboratory Press 1989, Second Edition).

A further aspect of the invention provides a second antibody fragment obtainable by the methods described in the foregoing. This second antibody fragment may advantageously be in the form of an scFv fragment or a Fab fragment. The second antibody fragment has the advantage that it is recombinantly expressible in soluble form and specifically binds the same antigen as both the source immunoglobulin and the first antibody fragment, whereas a corresponding antibody fragment, i.e. an antibody fragment converted directly from the source immunoglobulin without first performing the inventive method, would not have been obtainable, either at all or in sufficient amount in soluble form. Seen this way, the second antibody fragment represents a molecular species in which the antigen binding properties of both the source immunoglobulin and the first antibody fragment have been "rescued" in the form of an antibody fragment.

While modification of sequences comprised in the second antibody fragment to lessen the propensity of the second antibody fragment to elicit an immunogenic response from a host subject into which the second antibody fragment is introduced is possible in an analogous sense as already described above for modification of the first antibody variable region, such modification will generally not be necessary. This is because it will be possible to construct the combinations between first and second antibody variable regions on the one hand, and between second and third antibody variable regions on the other hand such that second and third antibody variable regions each stem from libraries which have been developed using the same species as the species to which the second antibody is to be administered as a therapeutic agent. It is more often practical to modulate the immunogenic properties of the second antibody fragment in this manner than it would be to derive, say, a third antibody variable region from a species other than that to which the second antibody fragment is to be administered, and then subsequently humanize and/or deimmunize said third antibody variable region.

A further aspect of the invention provides a second or a third antibody variable region derived from the second antibody fragment. In a preferred embodiment, the third antibody variable region is a VH.

Further aspects of the invention in this context provide a polypeptide comprising said VH, any nucleic acid molecule encoding such a polypeptide, and any nucleic acid molecules hybridizing with the nucleic acid molecule encoding such a polypeptide.

A further aspect of the invention provides a composition comprising a first and/or second antibody fragment as set out hereinabove. In a preferred embodiment, the composition comprises a first, second and/or third antibody variable region as set out herein above. In an especially preferred embodiment the composition comprises a VL exhibiting an amino acid sequence corresponding to the amino acid sequence of the VL region in any of FIGS. 11-35.

A further aspect of the invention provides a use of a composition as set out above for the preparation of a medicament. According to a preferred embodiment, the medicament is suitable for administration to a subject for the treatment of autoimmune diseases or inflammatory conditions. According to an especially preferred embodiment of the invention, such autoimmune diseases may be chosen from one or more of the following diseases or conditions: rheumatoid arthritis, chronic obstructive pulmonary disease (COPD), asthma, multiple sclerosis (MS), and psoriasis. According to another especially preferred embodiment of the invention, such inflammatory conditions include chronic inflammatory conditions and/or airway inflammation.

Further details and advantages of the invention will be explained in light of the following non-limiting figures and examples.

FIGURE LEGENDS

FIG. 1: Recombinant human GM-CSF-specific ELISA-analysis of periplasmic preparations of nine clones containing SCA fragments of the maternal anti-human GM-CSF antibody (i.e. the "corresponding antibody fragment" derived from direct conversion of the "source immunoglobulin" into SCA format). Preparations of soluble SCA fragments were added to wells of an ELISA-plate which had been coated with a soluble recombinant human GM-CSF antigen (*E. coli* material). Detection of SCA-fragments bound to immobilized recombinant human GM-CSF antigen was carried out using a Penta-His antibody (Qiagen, 1 µg/mL PBS) detected with horseradish peroxidase-conjugated goat anti-mouse IgG Fab2 specific polyclonal antibody (Jackson, 1 µg/mL PBS). The signal was developed by adding ABTS (2,2'-Azino-di[3-ethylbenzthiazoline sulfonate (6)] diammonium sal5t) substrate solution and detected at a wavelength of 405 nm. The OD-values (y axis) were measured at 405 nm by an ELISA reader. Clone numbers are presented on the x axis, the murine anti human-GM-CSF antibody 7A6 was used as a positive control, an irrelevant SCA containing periplasmic preparation was used as a negative control.

Figure 2:
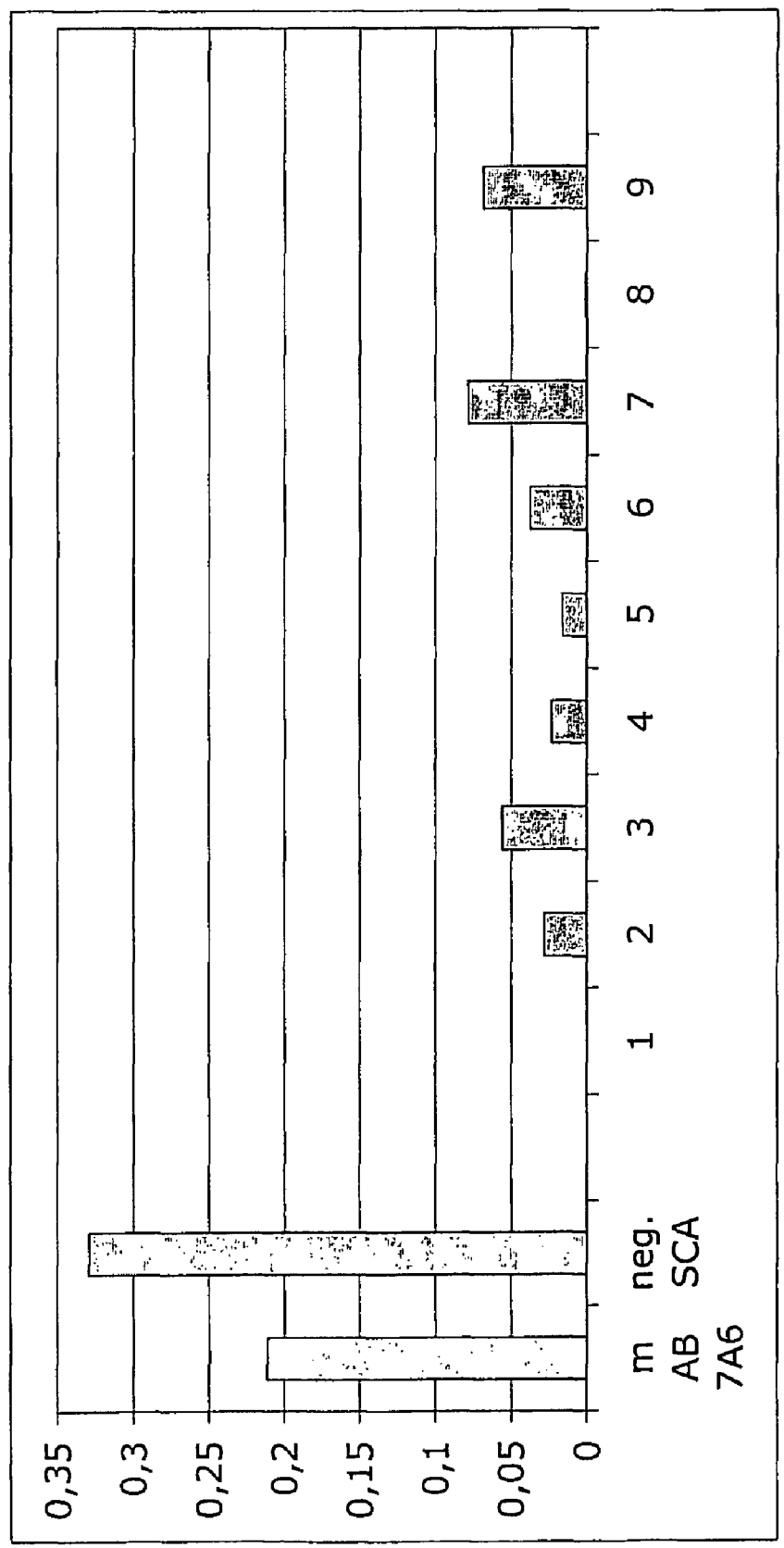

FIG. 2: Recombinant human GM-CSF-specific ELISA-analysis of periplasmic preparations of nine clones containing SCA fragments of the maternal anti-human GM-CSF antibody (i.e. the "corresponding antibody fragment" derived resulting from direct conversion of the "source immunoglobulin" into SCA format). Preparations of soluble SCA fragments were added to wells of an ELISA-plate which had been coated with a soluble recombinant human GM-CSF antigen (*E. coli* material). Detection of SCA-fragments bound to immobilized recombinant human GM-CSF antigen was carried out using a Penta-His antibody (Qiagen, 1 µg/mL PBS) detected with horseradish peroxidase-conjugated goat anti mouse IgG Fab2 specific polyclonal antibody (Jackson, 1 µg/L PBS). The signal was developed by adding ABTS (2,2'-Azino-di[3-ethylbenzthiazoline sulfonate (6)] diammonium salt) substrate solution and detected at a wavelength of 405 nm. The OD-values (y axis) were measured at 405 nm by an ELISA reader. Clone numbers are presented on the x axis, the murine anti human-GM-CSF antibody 7A6 and an irrelevant SCA-containing periplasmic preparation was used as a positive control.

Figure 3:
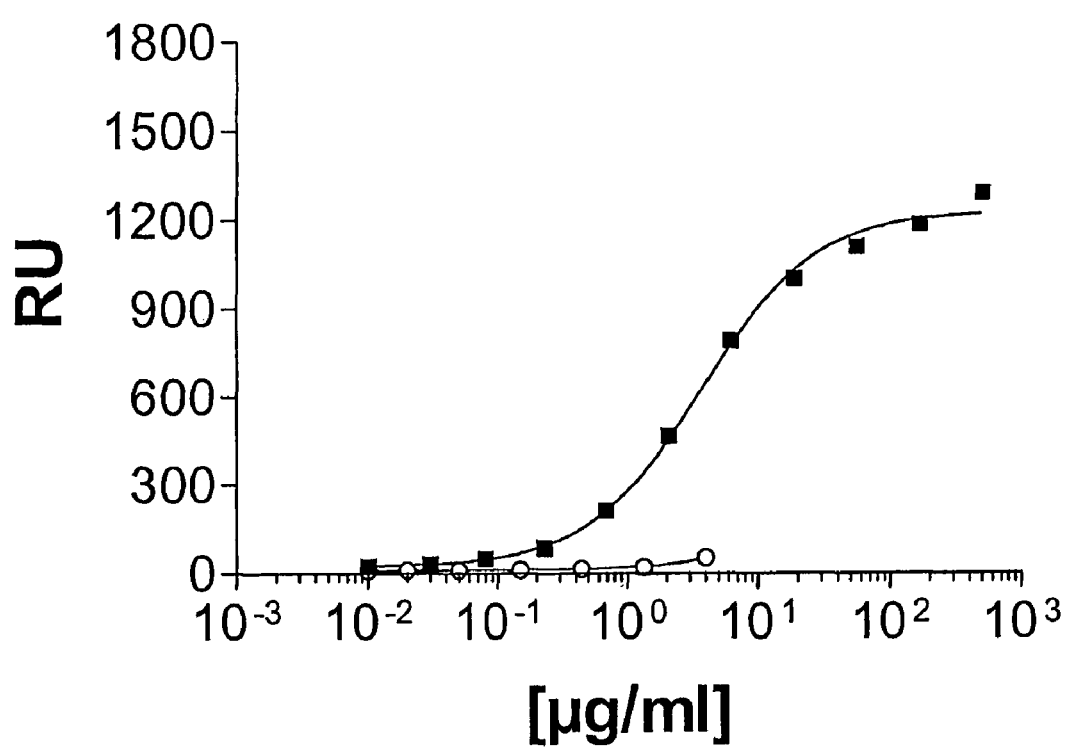

FIG. 3: Binding of maternal mAb and refolded maternal SCA to recombinant human GM-CSF (rhGM-CSF) immobilized on BIAcore sensor chip by surface plasmon resonance. Equilibrium binding of the maternal mAb (filled squares) and refolded maternal SCA (open circles) were measured injecting 10 µL of protein solution at concentrations ranging from 1 mg/mL to 6 ng/mL and monitoring the dissociation for 100 sec. Protein was buffered in HBS-EP. The relative response signal was determined at 100 sec of dissociation and plotted against the respective protein concentration. The data were fitted for half maximal binding at equilibrium (KD) using the Prism software program. The maternal mAb binds to the immobilized rhGM-CSF with an apparent equilibrium binding constant KD of 5 µg/mL (30 nM).

Figure 4:
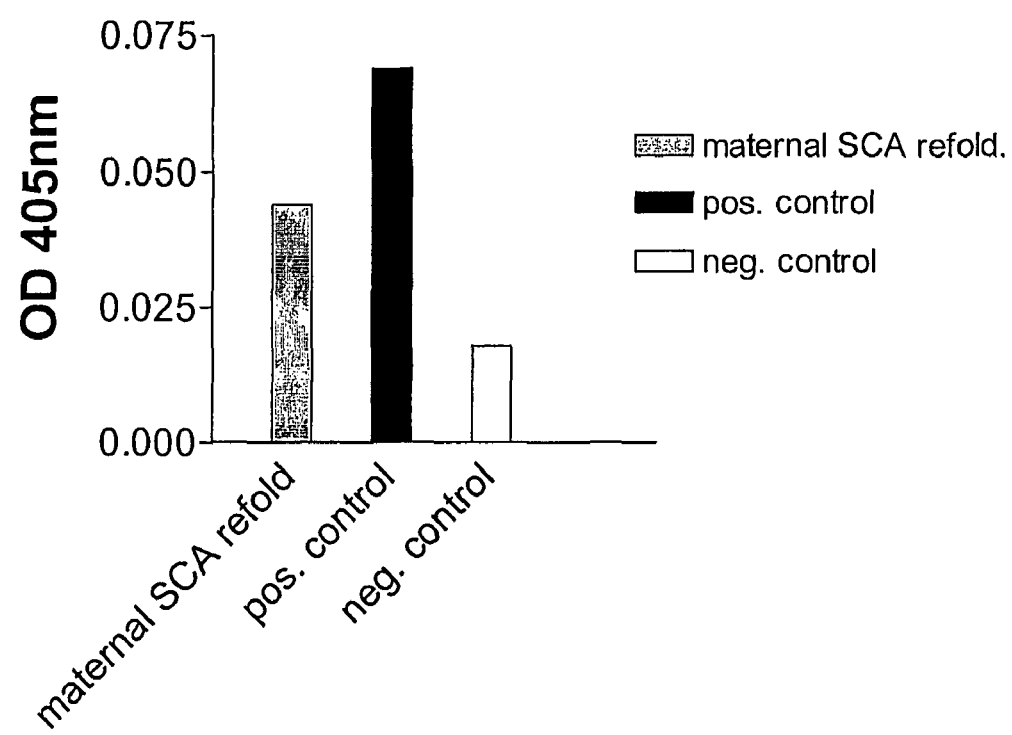

FIG. 4: Binding to rhGM-CSF of Maternal SCA Determined by ELISA.

ELISA experiments were carried out by coating the rhGM-CSF on wells of 96-well plastic plates (Nunc, maxisorb) typically at 4° C. overnight. The antigen was then removed, wells washed once with PBS/0.05% Tween 20 and subsequently blocked with PBS/3% BSA for at least one hour. After removal of the blocking solution, refolded maternal SCA and SCA controls were added to the wells and typically incubated for one hour at room temperature. The wells were then washed three times with PBS/0.05% Tween 20. Detection of SCA and control antibodies bound to immobilized antigen was carried out using a monoclonal murine anti-His6 antibody (Qiagen anti-PentaHis typically at a final concentration of 1 µg/ml PBS) detected with a peroxidase-labeled polyclonal goat anti-(mouse Fab-fragment) antibody (Dianova, 1 µg/ml PBS). The signal was developed by adding ABTS substrate solution and measured at a wavelength of 405 nm. Background reaction of an unrelated sample SCA with the coated antigen was determined (neg. control) as well as specific binding of an SCA known to interact with high specificity with the rhGM-CSF (pos. control). The refolded maternal SCA shows a clear binding signal to the antigen rhGM-CSF.

Figure 5:
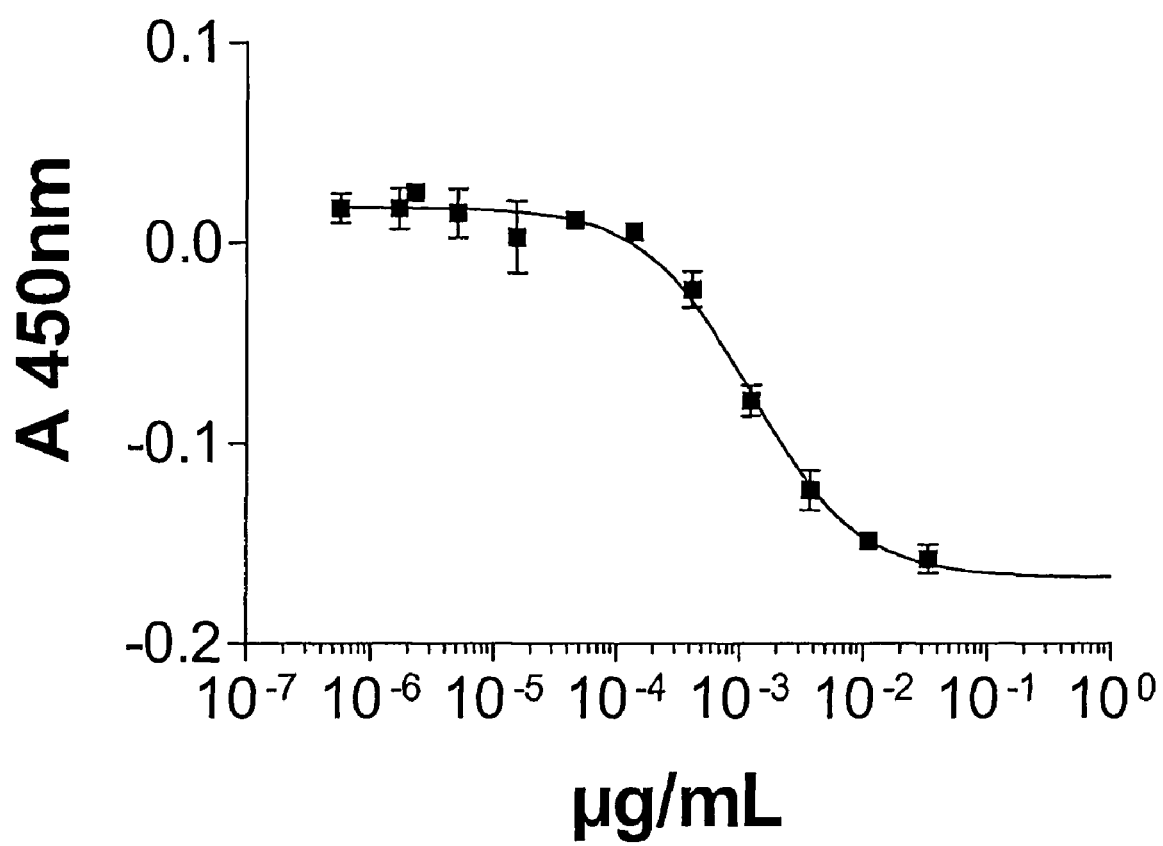

FIG. 5: Inhibition of rhGM-CSF dependent proliferation of TF-1 cells by maternal mAb. TF-1 cells were cultivated at a final concentration of 1×10exp5 cells/mL in RPMI 1640, 10% FCS and 90 µL cell suspension per well are used (0.9× 10exp4 cells/well). A final concentration of 0.3 ng/mL rhGM-CSF was used to stimulate the proliferation of the TF-1 cells. For neutralization of GM-CSF dependent proliferation maternal mAb in 1× PBS was added in a dilution series with final protein concentrations ranging from 30 ng/mL to 1 pg/mL. TF-1 cells were incubated at 37° C. at 5% $CO_2$ in the presence of GM-CSF and maternal mAb for 72 h. 10 µL WST-1 (Roche) was added and the absorption at 450 nm (A 450 nm) was determined and plotted against the protein concentration. The data were fitted for half maximal inhibition of proliferation (IC50) using the non-linear regression curve fit of the Prism software. The maternal mAb inhibits the rhGM-CSF induced proliferation of the TF-1 cells with an $IC_{50}$ of 1.2 ng/mL (80 pM).

Figure 6:
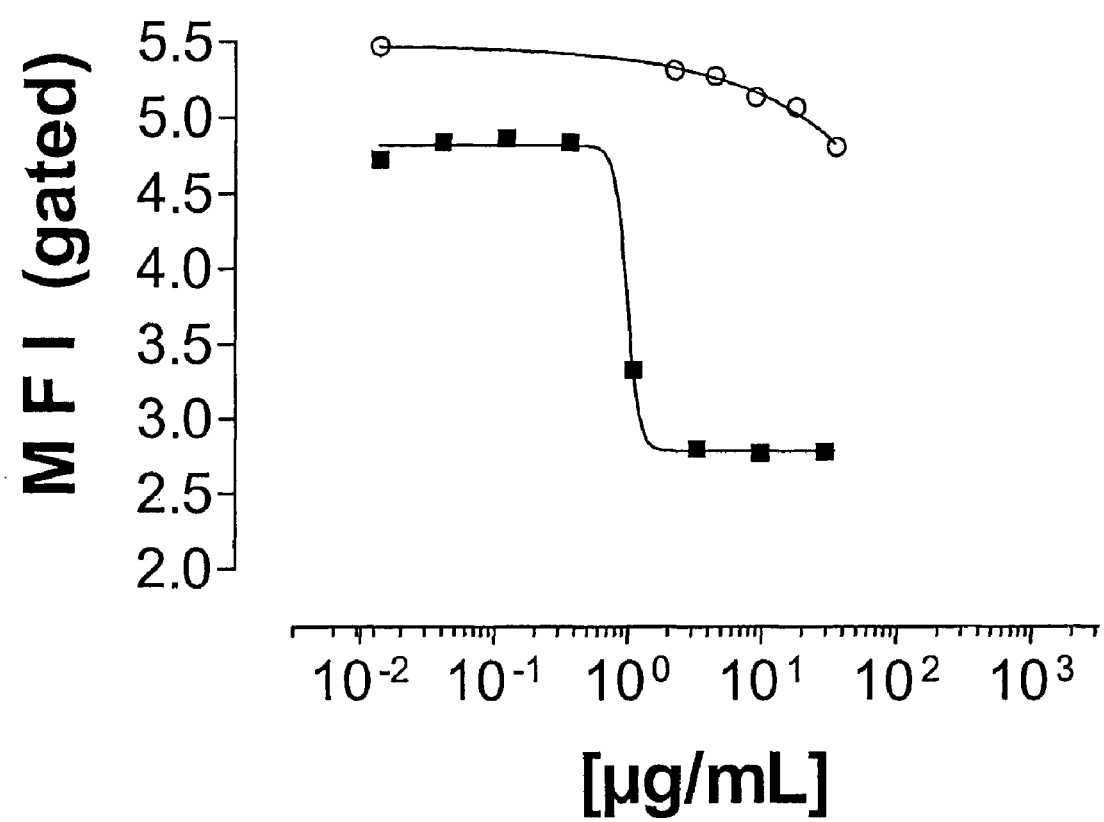

FIG. 6: Inhibition of Binding of hGM-CSF-FITC to TF-1 Cells by Maternal mAb and Maternal SCA.

For the flow cytometry based assay a final concentration of 0.4 µg/mL hGM-CSF-FITC conjugate in PBS were incubated with maternal mAb (filled squares) in concentrations ranging from 30 µg/mL to 0.014 µg/mL or the refolded maternal SCA (open circles). The protein samples were left to equilibrate at 25° C. for 1 h prior to addition of TF-1 cell suspension. The TF-1 were cultivated in RPMI 1640 medium GIBCO (L-glutamine, phenol-red free), 10% heat inactivated FCS in the absence of rhGM-CSF overnight. A final concentration of 2×10exp6 cells/mL and 150 µl of cell suspension was used per sample. The cells were harvested by centrifugation at 500 G at 4° C. for 3 min and washed twice with FACS buffer. The washed cells were resuspended in 100 µL of pre-equilibrated protein sample containing the hGM-CSF-FITC and maternal nab or maternal SCA respectively. The samples were incubated at 4° C. for 60 min. After two further washes the cells were resuspended in 150 µL ice cold FACS buffer and subsequently analysed by flow cytometry. The mean fluorescence intensity (MFI) was plotted against the concentration of the used maternal mAb and maternal SCA. A clear concentration dependent loss of fluorescence intensity of the TF-1 cells was observed with the maternal mAb. The refolded maternal SCA induced some residual concentration dependent decrease in fluorescence intensity of the hGM-CSF-FITC labelled TF-1 cells, indicating its activity.

Figure 7:
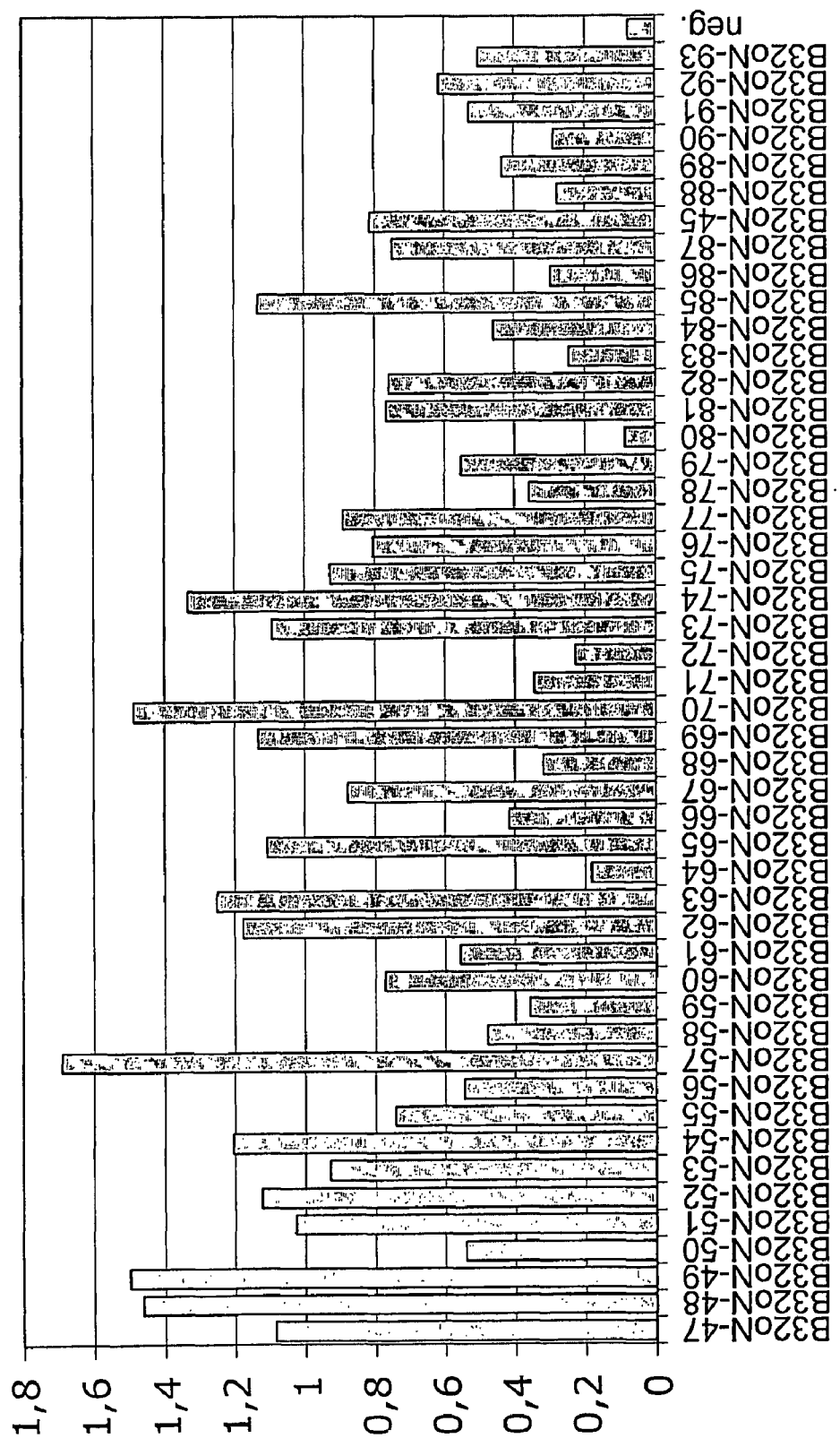

FIG. 7: Recombinant human GM-CSF-specific ELISA-analysis of periplasmic preparations containing SCA fragments derived from the method of the invention. Preparations of soluble SCA protein fragments were added to wells of an ELISA-plate which had been coated with a soluble recombinant human GM-CSF antigen (Leukine). Detection of SCA-fragments bound to immobilized recombinant human GM-CSF antigen (Leukine) was carried out using a biotinylated anti-flag M2 (1 µg/mL PBS/1% BSA) detected with horseradish peroxidase-conjugated goat anti mouse Fab2 specific polyclonal antibody (Dianova, 1 µg/mL PBS/1%BSA). The signal was developed by adding ABTS (2,2'-Azino-di[3-ethylbenzthiazoline sulfonate (6)] diammonium salt) substrate solution and detected at a wavelength of 405 nm. The OD-values (y axis) were measured at 405 nm by an ELISA reader. Clone numbers are presented on the x axis, where the first number of the clone number indicates the round of panning in which the respective clone was obtained (32=fifth round, 33=sixth round; B and C indicating the series of selection), while the second number indicates the respective clone of this round.

Figure 8:
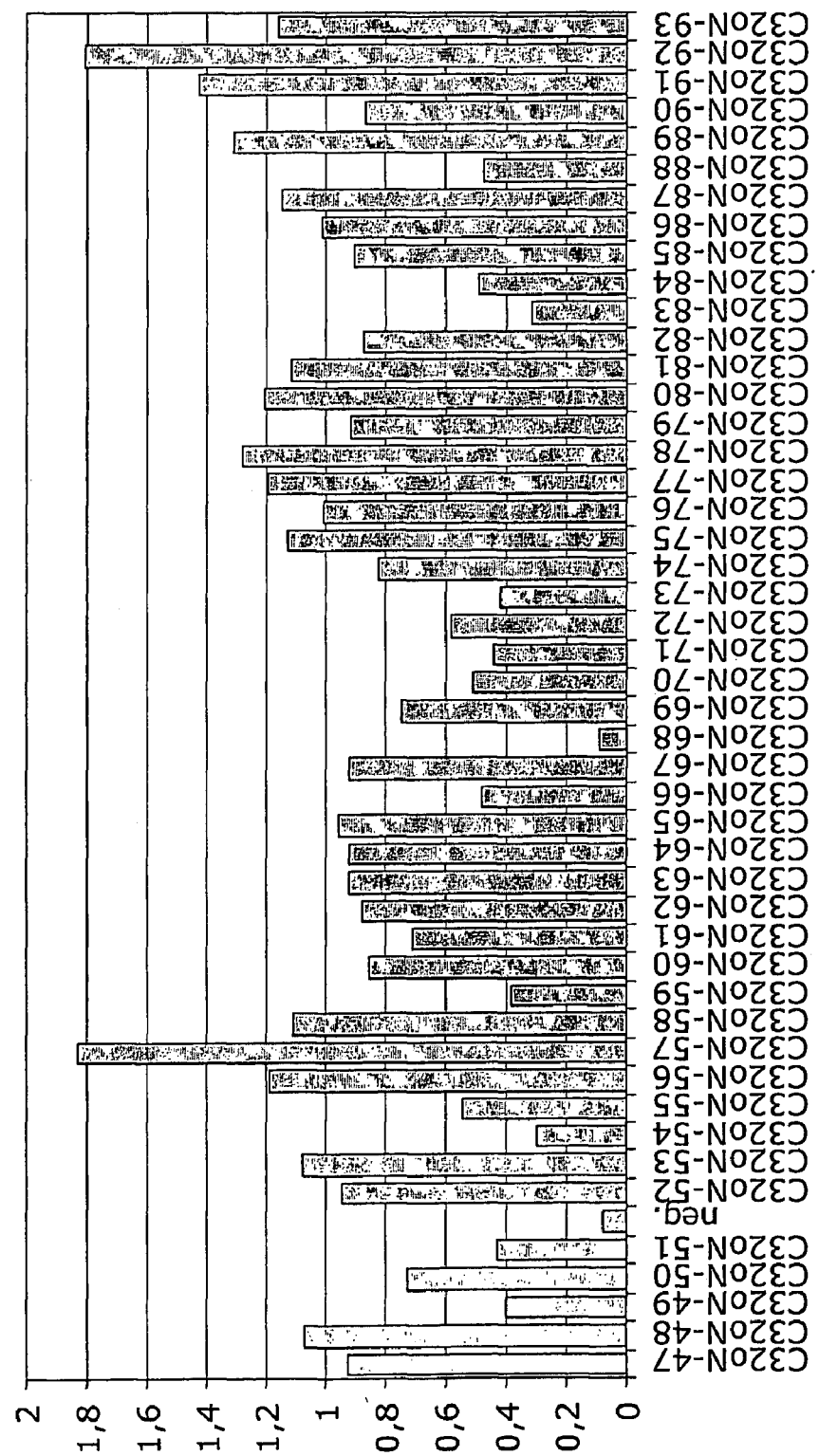

FIG. 8: Recombinant human GM-CSF-specific ELISA-analysis of periplasmic preparations containing SCA protein fragments derived from the method of the invention. Preparations of soluble SCA protein fragments were added to wells of an ELISA-plate, which had been coated with a soluble recombinant human GM-CSF antigen (Leukine). Detection of SCA-fragments bound to immobilized recombinant human GM-CSF antigen (Leukine) was carried out using a biotinylated anti-flag M2 (1 µg/mL PBS/1% BSA) detected with horseradish peroxidase-conjugated goat anti mouse Fab2 specific polyclonal antibody (Dianova, 1 µg/mL PBS/1% BSA). The signal was developed by adding ABTS (2,2'-Azino-di[3-ethylbenzthiazoline sulfonate (6)] diammonium salt) substrate solution and detected at a wavelength of 405 nm. The OD-values (y axis) were measured at 405 nm by an ELISA reader. Clone numbers are presented on the x axis, where the first number of the clone number indicates the round of panning in which the respective clone was obtained (32=fifth round, 33=sixth round; B and C indicating the series of selection), while the second number indicates the respective clone of this round.

Figure 9:
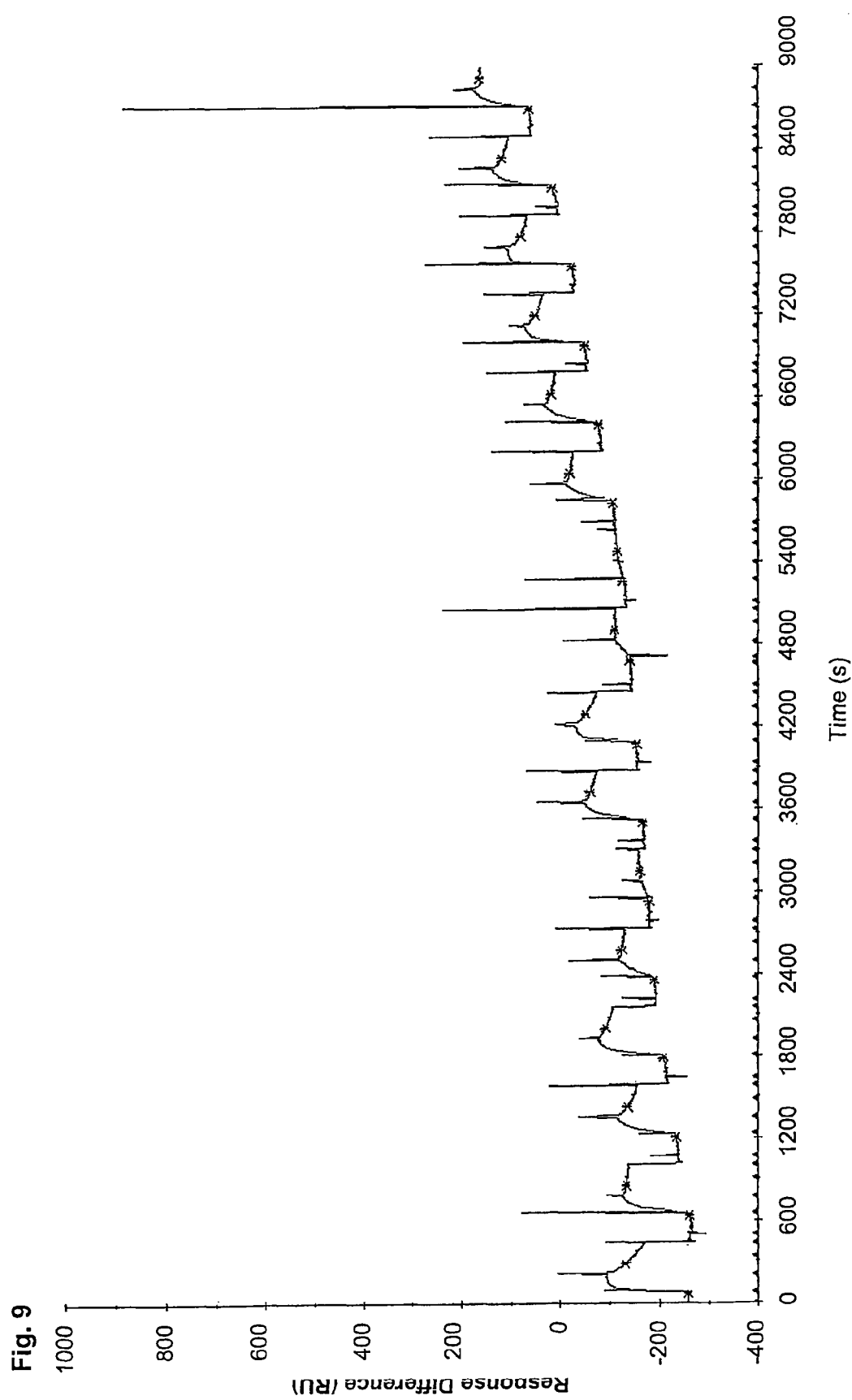

FIG. 9: Binding analysis (kinetic off rate) of SCA hits derived from the method of the invention, as determined by SPR. Binding kinetics of the SCA hits were measured injecting 10 µL of purified periplasmic preparation ("PPP") protein solution with a flow rate of 5 µL/min at 25° C. onto the sensor chip. The data were monitored in all four flow cells. Background association with the unmodified CM5 chip surface (FC1) was substracted from the binding to the immobilised rhGM-CSF (FC2) allowing analysis of the specific binding signal (FC2-FC1 response difference). The dissociation rate was monitored for 100 sec (FIG. 4). The amplitude of the binding peak (RUmax) directly correlates to the protein concentration in the injected sample. The kinetic association rate constant (ka) is concentration dependent and can—due to varying concentrations of the PPP protein solution—not be used for the qualitative ranking of the purified PPP SCA material. The kinetic dissociation rate constant (kd) is protein concentration independent and characteristic for the binding strength of the respective SCA hit. The SCA hits with the best apparent off rate were identified.

Figure 10:
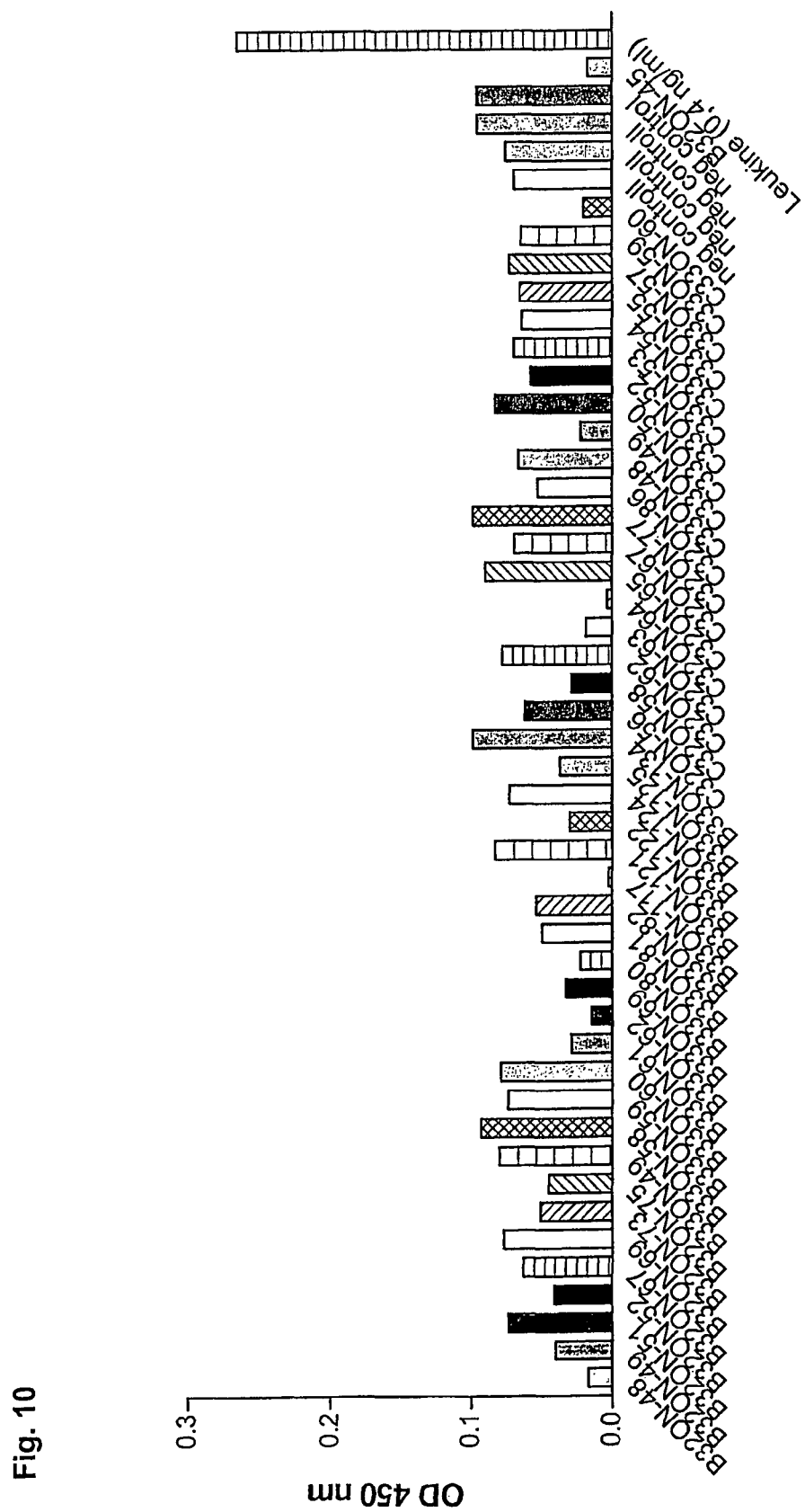

FIG. 10: Inhibition of rhGM-CSF-dependent proliferation of TF-1 cells by SCA hits.

Cells were resuspended at a final concentration of $1 \times 10exp^5$ cells/mL in RPMI 1640, 10% FCS and 90 µL cell suspension per well were used ($0.9 \times 10exp4$ cells/well). A final concentration of 0.3 ng/mL rhGM-CSF was used to stimulate the proliferation of the TF-1 cells. For neutralization of hGM-CSF dependent proliferation purified PPP of the SCA hits were dialyzed against 1×PBS at 25° C. for 2 h. 10 µL of dialyzed and sterile filtered protein solution (0.22 µm filter) were added to 100 µL TF-1 and rhGM-CSF solution. The samples were incubated at 37° C. at 5% $CO_2$ for 72 h. After 72 h the proliferative status of the TF-1 cells was determined adding WST-1 and monitoring the colorimetric change with an ELISA reader at 450 nm. The inhibition of the rhGM-CSF dependent proliferation of the TF-1 cells by the SCA constructs is of varying strength. Some SCA constructs do not inhibit the proliferation to a large degree—this can be due to a lack of stable complex formation of the SCA constructs and the rhGM-CSF over the period of 72 h at 37° C.

FIG. 11: Nucleotide and amino acid sequences of the nucleic acid molecule encoding half-human SCA B32oN-10 and of half-human SCA B32oN-10, respectively (SEQ ID NOS:2 and 3). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. Complementarity determining regions (CDRs) are indicated by boxes surrounding the relevant nt and aa positions (according to the Kabat definition for CDRs).

FIG. 12: Nucleotide and amino acid sequences of the nucleic acid molecule encoding half-human SCA B32oN-33 and of half-human SCA B32oN-33, respectively (SEQ ID NOS:4 and 5). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 13: Nucleotide and amino acid sequences of the nucleic acid molecule encoding half-human SCA B32oN-44 and of half-human SCA B32oN-44, respectively (SEQ ID NOS:6 and 7). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 14: Nucleotide and amino acid sequences of the nucleic acid molecule encoding half-human SCA B32oN-45 and of half-human SCA B32oN-45, respectively (SEQ ID NOS:8 and 9). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 15: Nucleotide and amino acid sequences of the nucleic acid molecule encoding half-human SCA B32oN-48 and of half-human SCA B32oN-48, respectively (SEQ ID NOS:10 and 11). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 16: Nucleotide and amino acid sequences of the nucleic acid molecule encoding half-human SCA B32oN-49 and of half-human SCA B32oN-49, respectively (SEQ ID NOS:12 and 13). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 17: Nucleotide and amino acid sequences of the nucleic acid molecule encoding half-human SCA B32oN-67 and of half-human SCA B32oN-67, respectively (SEQ ID NOS:14 and 15). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 18: Nucleotide and amino acid sequences of nucleic acid molecule encoding the half-human SCA B32oN-73 and of half-human SCA B32oN-73, respectively (SEQ ID NOS: 16 and 17). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 19: Nucleotide and amino acid sequences of the nucleic acid molecule encoding half-human SCA B33oN-21 and of half-human SCA B33oN-21, respectively (SEQ ID NOS:20 and 21). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 20: Nucleotide and amino acid sequences of the nucleic acid molecule encoding half-human SCA B33oN-22 and of half-human SCA B33oN-22, respectively (SEQ ID NOS:22 and 23). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 21: Nucleotide and amino acid sequences of the nucleic acid molecule encoding half-human SCA B33oN-115 and of half-human SCA B33oN-115, respectively (SEQ ID NOS:32 and 33). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 22: Nucleotide and amino acid sequences of the nucleic acid molecule encoding half-human SCA B33oN-35 and of half-human SCA B33oN-35, respectively (SEQ ID NOS:24 and 25). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 23: Nucleotide and amino acid sequences of the nucleic acid molecule encoding half-human SCA B33oN-66 and of half-human SCA B33oN-66, respectively (SEQ ID NOS:26 and 27). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 24: Nucleotide and amino acid sequences of the nucleic acid molecule encoding half-human SCA B33oN-67 and of half-human SCA B33oN-67, respectively (SEQ ID NOS:27 and 28). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 25: Nucleotide and amino acid sequences of the nucleic acid molecule encoding half-human SCA B33oN-69 and of half-human SCA B33oN-69, respectively (SEQ ID NOS:30 and 31). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 26: Nucleotide and amino acid sequences of the nucleic acid molecule encoding half-human SCA B33oN-8 and of half-human SCA B33oN-8, respectively (SEQ ID NOS:18 and 19). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 27: Nucleotide and amino acid sequences of the nucleic acid molecule encoding half-human SCA C32oN-10 and of half-human SCA C32oN-10, respectively (SEQ ID NOS:34 and 35). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 28: Nucleotide and amino acid sequences of the nucleic acid molecule encoding half-human SCA C32oN-21 and of half-human SCA C32oN-21, respectively (SEQ ID NOS:36 and 37). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 29: Nucleotide and amino acid sequences of the nucleic acid molecule encoding half-human SCA C32oN-34 and of half-human SCA C32oN-34, respectively (SEQ ID NOS:38 and 39). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 30: Nucleotide and amino acid sequences of the nucleic acid molecule encoding half-human SCA C32oN-46 and of half-human SCA C32oN-46, respectively (SEQ ID NOS:40 and 41). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 31: Nucleotide and amino acid sequences of the nucleic acid molecule encoding half-human SCA C32oN-89 and of half-human SCA C32oN-89, respectively (SEQ ID NOS:42 and 43). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 32: Nucleotide and amino acid sequences of the nucleic acid molecule encoding half-human SCA C32oN-92 and of half-human SCA C32oN-92, respectively (SEQ ID NOS:44 and 45). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 33: Nucleotide and amino acid sequences of the nucleic acid molecule encoding half-human SCA C33oN-32 and of half-human SCA C33oN-32, respectively (SEQ ID NOS:46 and 47). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 34: Nucleotide and amino acid sequences of the nucleic acid molecule encoding half-human SCA C33oN-33 and of half-human SCA C33oN-33, respectively (SEQ ID NOS:48 and 49). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

FIG. 35: Nucleotide and amino acid sequences of the nucleic acid molecule encoding half-human SCA C33oN-49 and of half-human SCA C33oN-49, respectively (SEQ ID NOS:50 and 51). Numbers indicate the nucleotide (nt) positions, amino acids (aa) are presented in single letter code. The region of the DNA coding for the V-region of the heavy chain starts at nt 1 and ends at nt 360 followed by a $(G_4S_1)_3$-linker. The region of the DNA coding for the V-region of the kappa (light) chain starts at nt 406 and ends at nt 726. CDRs are indicated by boxes surrounding the relevant nt and aa positions (according to the Kabat definition for CDRs).

Figure 36:
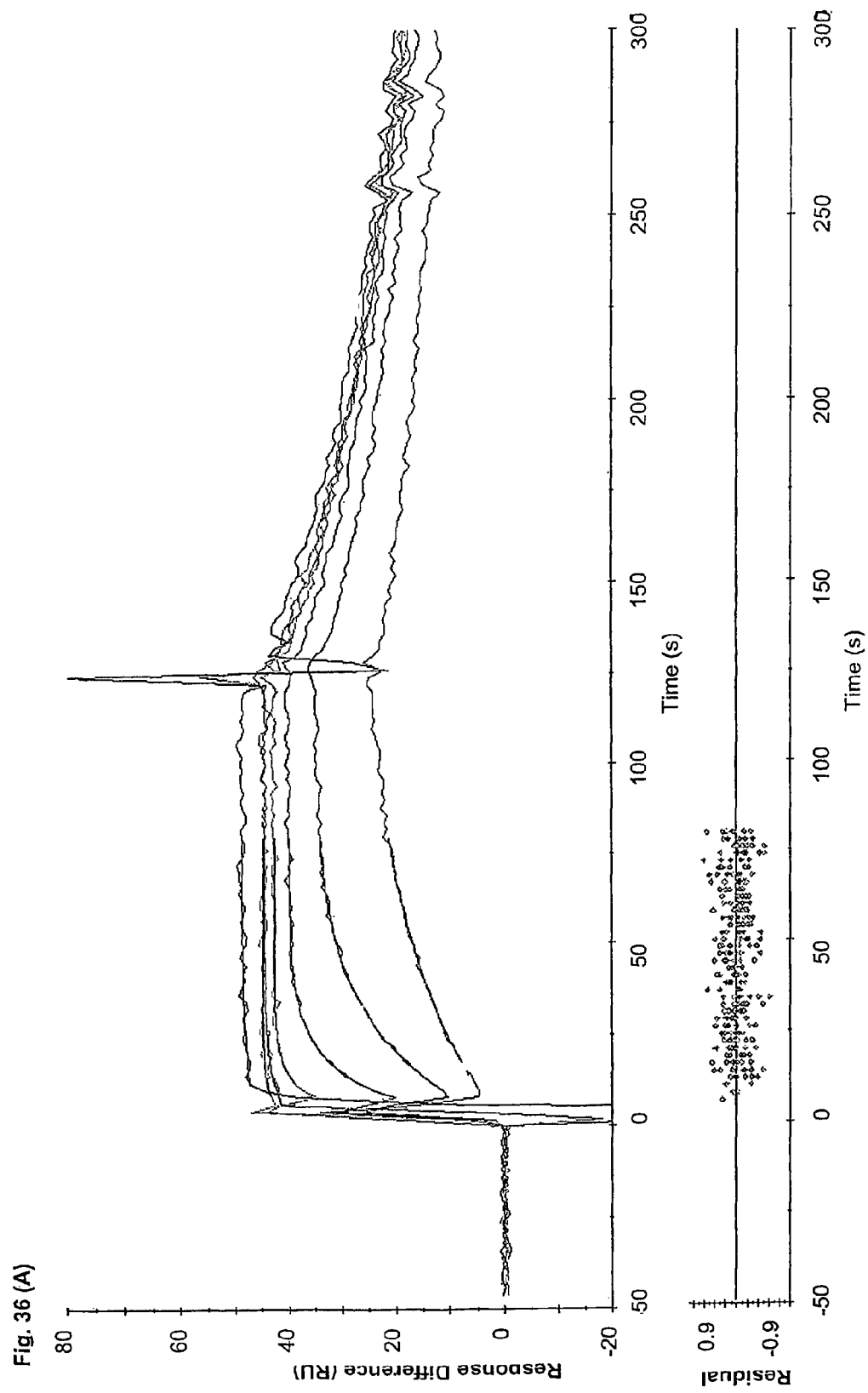
Figure 36:
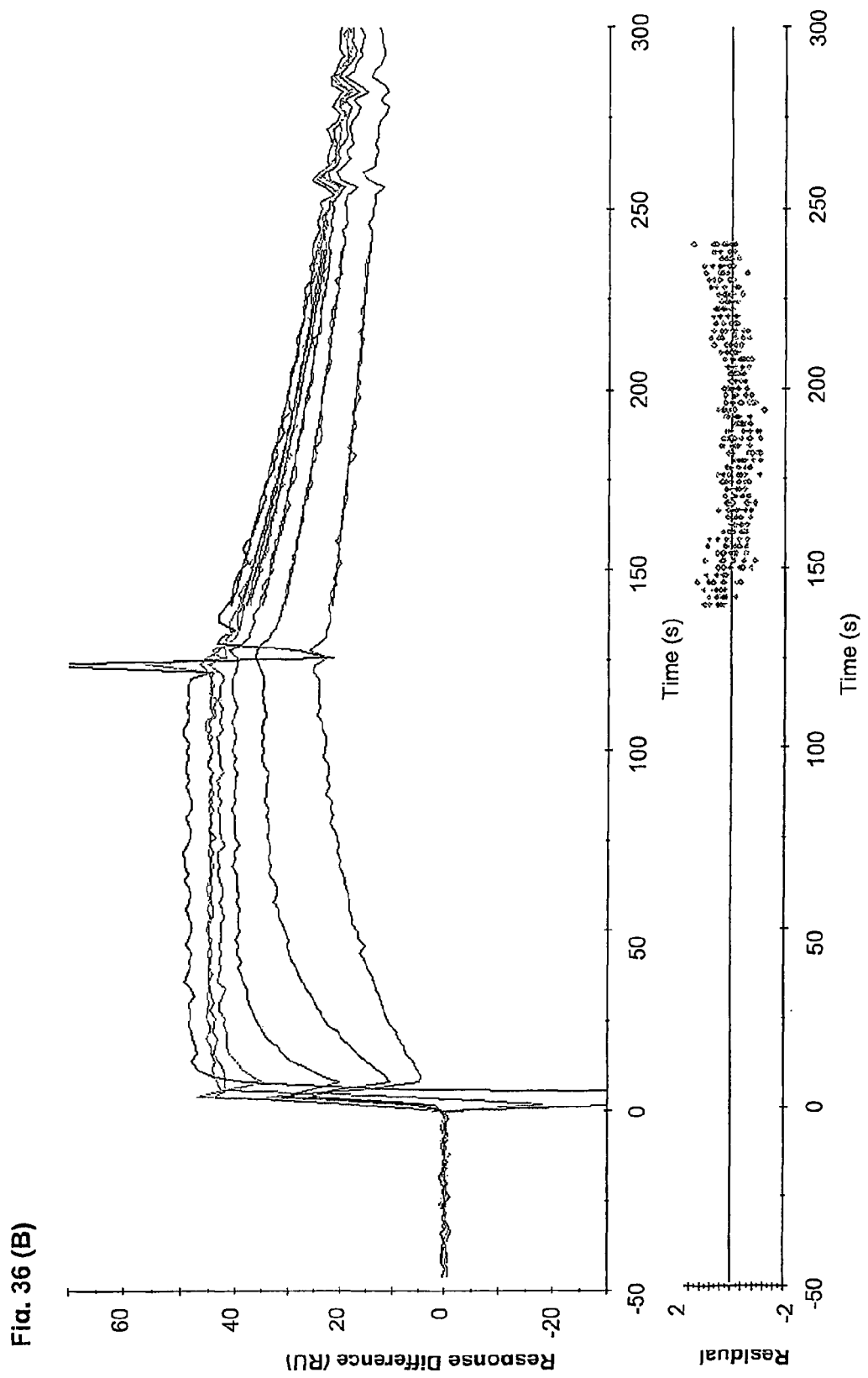

FIG. 36A, B: Kinetic binding analysis of SCA leads derived from the method of the invention, as determined by SPR. Binding kinetics (kd and ka) of the SCA leads were measured injecting 10 μL of purified protein in dilution series ranging from 10 μg/mL to 1 pg/mL purified SCA onto a rhGM-CSF coated sensor chip surface. The dissociation was monitored at 25° C. for 100 sec. Data were fitted using BIAevalution™ software determining the rate constant for dissociation (FIG. 36B) and association (FIG. 36A) kinetics. The results are summarized in Table 1. The residuals corresponding to the fitted data monitoring the deviation from the raw data indicated no systematic deviation for the fit.

Figure 37:
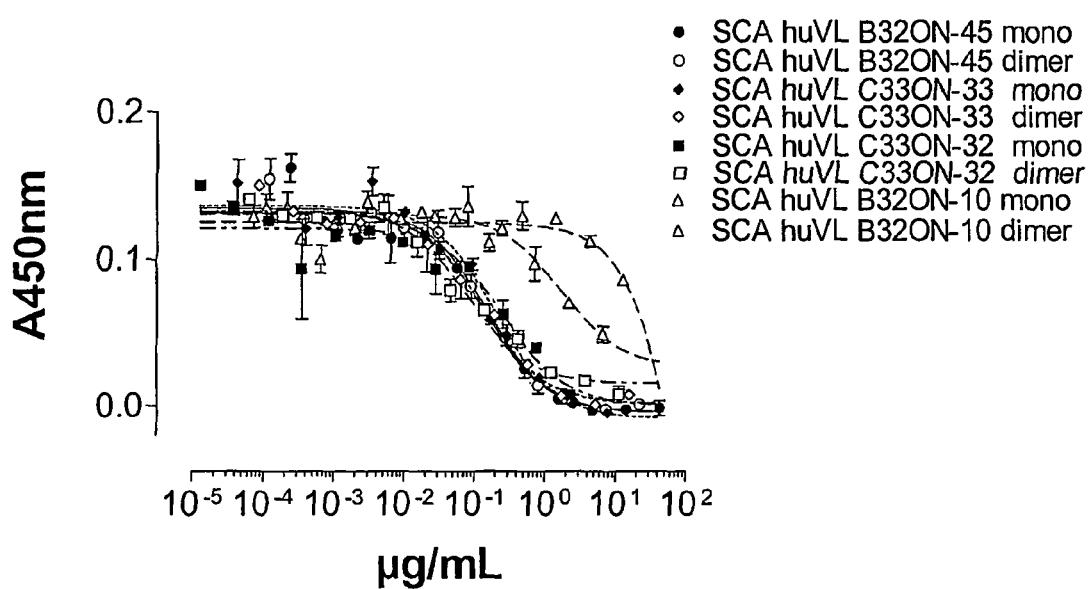

FIG. 37: Inhibition of rhGM-CSF dependent proliferation of TF-1 cells by SCA constructs. TF-1 cells were resuspended at a final concentration of 1×10exp5 cells/mL in RPMI 1640, 10% FCS and 90 μL cell suspension per well were used (0.9×10exp4 cells/well). A final concentration of 0.3 ng/mL rhGM-CSF was used to stimulate the proliferation of the TF-1 cells. For neutralization of hGM-CSF dependent proliferation purified SCA in 1× PBS was added in a dilution series with final protein concentrations ranging from 100 μg/mL to 10 pg/mL. 10 μL of dialyzed and sterile filtered protein solution (0.22 μm filter) was added to 100 μL TF-1 and rhGM-CSF solution. The samples were incubated at 37° C. at 5% $CO_2$ for 72 h. After 72 h the proliferative status of the TF-1 cells was determined adding WST-1 and monitoring the colorimetric change with an ELISA reader at 450 nm:

EXAMPLES

Example 1

Procurement of the Recombinant Human GM-CSF Antigen 1.1 Cloning, Expression and Purification of the Human GM-CSF Antigen:

The gene encoding for the human GM-CSF antigen was subcloned into the pET22b(+) (Novagene, USA) from the expression vector pORF-hGM-CSF (Novagen, USA) via the PCR-introduced restriction enzyme recognition sites NdeI and XhoI. The hGM-CSF encoding gene in pET22b(+) is fused to the pelB leader sequence and is suitable for expression in *E. coli* periplasm.

Protein production and purification was performed as described by the manufacturer. In brief, *E. coli* BL21DE3 were transformed with the expression plasmid and grown at 37° C. in selective medium to an optical density at 600 nm of 0.5-0.8. Protein production was induced by addition of IPTG to 1 mM and reduction of temperature to 25° C. A periplasmic preparation was done via osmotic shock using 20% sucrose solution to selectively destroy the cell wall maintaining an intact cell membrane. The native hGM-CSF contains two formed disulfide bridges and expression in the oxidative periplasm of *E. coli* allows for formation of these functionally important disulfide bridges.

Recombinant human GM-CSF ("hGM-CSF") was purified in a two step purification process via immobilized metal affinity chromatography (IMAC) and gel filtration. An Äkta® FPLC System (Pharmacia) and Unicorn® Software were used for chromatography. All chemicals were of research grade and purchased from Sigma (Deisenhofen) or Merck (Darmstadt).

IMAC was performed using a Qiagen Ni-NTA Superflow column according to the protocol provided by the manufacturer. The column was equilibrated with buffer A2 (20 mM sodium phosphate pH 7.2, 0.4 M NaCl) and the periplasmic preparation (PPP) (100 mL) was applied to the column (2 mL) at a flow rate of 2 mL/min. The column was washed with 5 column volumes 5% buffer B2 (20 mM sodium phosphate pH 7.2, 0.4 M NaCl, 0.5 M imidazol) to remove unbound sample. Bound protein was eluted using 100% buffer B2 in 5 column volumes. Eluted protein fractions were pooled for further purification.

Gel filtration chromatography was performed on a Superdex 200 Prep Grade column (Pharmacia) equilibrated with PBS (Gibco). Eluted protein samples (flow rate 1 mL/min) were subjected to standard SDS-PAGE and Western Blot for detection. Prior to purification, the column was calibrated for molecular weight determination (molecular weight marker kit, Sigma MW GF-200). Protein concentrations were determined measuring OD 280 nm and calculated using the sequence specific molecular extinction coefficient.

1.2 Biotinylation of the Recombinant Human GM-CSF Antigen

For phage library selection recombinant human GM-CSF antigen A) Leukine (Leukine Liquid, Immunex) and B) recombinant human GM-CSF produced in *E. coli* (see 1.1) were biotinylated. Biotinylation was accomplished in PBS containing 5% DMSO (Sigma) with a five-fold molar excess of EZ-Link Sulfo NHS-LC-LC-Biotin (Pierce) for 1 hour at room temperature in a sample mixer (Dynal). For the separation of free Biotin and biotinylated human GM-CSF antigen, anion exchange chromatography (Resource Q, Amersham Biosciences) was carried out according to standard protocols. The chromatography resulted in both approaches (A and B) in two elution peaks. In case A the primary eluted peak was fractionated again via a second anion exchange chromatography step (same conditions as above) into two elution peaks. Afterwards the obtained fractions were serially diluted (dilutions 1:2; start concentration 6 µg/µL determined from the peak height) coated to 96 wells ELISA plates and detected. The detection was carried out using A) an anti human GM-CSF antibody M500-A (Sigma, 2.5 µg/mL in PBS/1%BSA) detected with horseradish peroxidase-conjugated goat anti-mouse Fab2 specific polyclonal antibody (Dianova, 1 µg/mL PBS/1% BSA) and B) the maternal antibody (1 µg/mL PBS/1%BSA) detected with horseradish peroxidase-conjugated goat anti-rat polyclonal antibody (Dianova, 1 µg/mL PBS/1% BSA). The successful biotinylation was demonstrated by a similar ELISA experiment that was carried out using horseradish peroxide-conjugated streptavidin (Dako, 1 µg/mL PBS/1% BSA). The signal was developed by adding OPD substrate solution (Sigma) and detected at a wavelength of 492 nm (reference wavelength 620 µm). To estimate the degree of biotinylation the above mentioned ELISA was carried out using the anion exchange fractions directly or after an incubation step with $6.7 \times 10^{exp7}$ streptavidine magnetic beads (Dynabeads M-280-Streptavidine, Dynal) with gentle agitation for 30 minutes. The resulting supernatant was coated onto the wells of 96-well ELISA plates and detected as described above. The ELISA results showed that the second eluted peak contained the biotinylated human GM-CSF and that A) about 95% and B) about 50% of the eluted human GM-CSF was conjugated. Concentrations were estimated using the original material (A and B) as a standard and resulted in A) 100 µg/mL and B) 20 µg/mL.

The retained bioactivity of the biotin-labeled human GM-CSF was confirmed in TF-1 proliferation assays according to protocols described in the characterization of the single chain antibodies (SCAs).

1.3 Fluorescein Labeling of the Recombinant Human GM-CSF Antigen

For binding studies on TF-1 cells recombinant human GM-CSF antigen produced in *E. coli* (see 1.2.) was conjugated with fluorescein-5(6)-carboxamidocaproic acid N-succinimidyl ester (Fluka, fluorescein-NHS). The conjugation step was performed in borate buffer (0.05 M boric acid, 0.1 M NaCl, pH 8.5) containing 17.5% DMSO with a five fold molar excess of fluorescein-NHS for 1 hour at room temperature in a sample mixer. Afterwards a gel filtration (Sephadex G25 medium, Amersham Biosciences) was carried out to dissociate fluorescein-labeled human GM-CSF antigen from free fluorescein-NHS. The gel filtration resulted in two peaks measured at a wavelength of 485 nm (reference wavelength 535 nm), whereas the primary peak represents the FITC-labeled human GM-CSF. The degree of labeling was determined by defining the F/P ratio of the conjugate ([mg/mL]= $(A_{280}-0.35 \times A_{493}) \times 1.08$; F/P=$(A_{493}/73.000) \times (15.000/([mg/mL]))$. The determined concentration was 0.041 mg/mL with an F/P ratio of 1.2.

Example 2

Cloning, Expression and Characterization of the Maternal Anti-Human GM-CSF SCA 2.1. Cloning of the Maternal V-Regions from Hybridoma HB-9569

As used throughout the foregoing examples, a "maternal" V-region denotes that the V-region in question originates from a full immunoglobulin molecule. A "maternal" SCA refers to the SCA resulting from direct incorporation of the maternal V-regions into SCA format without performing the inventive method as described hereinabove. In the event that the "maternal SCA" exhibits insufficient soluble recombinant expression, such a "maternal SCA" therefore represents a "corresponding antibody fragment" of a "source immunoglobulin", as this term is used hereinbove.

As used throughout the foregoing examples, a "hit" denotes a molecule which is known to bind an antigen of interest, but which binding has not been quantitatively evaluated. A "hit" is a molecule in an early stage of characterization for which small-scale production might have already been performed. Such a molecule is in the validation stage of characterization.

As used throughout the foregoing examples, a "lead" molecule denotes a molecule the binding and neutralization potentials of which has been quantified. Production of a "lead" molecule has already taken place on a large scale.

The aim of this experiment is the isolation and sub-cloning of the genes encoding the VH and VL regions in the the maternal mAb produced by the hybridoma cell line HB-9569. The hybridoma HB-9569 was obtained from ATCC (USA). Hybridoma cells were cultivated in ATCC complete growth medium: RPMI 1640 medium with 2 mM L-glutamine adjusted to contain 1.5 g/L sodium bicarbonate, 4.5 g/L glucose, 10 mM BEPES, and 1.0 mM sodium pyruvate and supplemented with 0.05 mM 2-mercaptoethanol, fetal bovine serum 10% at 37° C. with 5% $CO_2$. For total RNA preparation, 1×10exp7 cells were used and RNA was prepared as described in the product manual of the Qiagen Omni-Skript Kit (Qiagen, Germany). cDNA was synthesized according to standard methods (Sambrook, Cold Spring Harbor Laboratory Press 1989, Second Edition).

For the isolation of light chain V-region DNA, RT-PCR was carried out using 5E1-kSalI-AS: TTT GCG GCC GCG TCG ACT AAC ACT CAT TCC TGT TG (SEQ ID NO:52) and MLALT3.RV: GCC GAA TTC CAC CAT GRA GTC ACA KAC YCA GGT CTT YRT A (SEQ ID NO:53) primer set. The following PCR-program was used for amplification: Denaturation at 94° C. for 15 seconds, primer annealing at 52° C. for 50 seconds and primer extension at 72° C. for 90 seconds were performed over 40 cycles, followed by final extension at 72° C. for 10 minutes. Light chain DNA V-fragments were then isolated according to standard protocols.

For the isolation of heavy chain V-region DNA, RT-PCR was carried out using MHALT1RV: GCC GAA TTC CAC CAT GGR ATG SAG CTG KGT MAT SCT CTT (SEQ ID NO:54) and Race GSP rIgG2aIb: CAC ACC GCT GGA CAG GGC TCC AGA GTT CC (SEQ ID NO:55) primer set. The following PCR-program was used for amplification: Denaturation at 94° C. for 15 seconds, primer annealing at 52° C. for 50 seconds and primer extension at 72° C. for 90 seconds were performed over 40 cycles, followed by final extension at 72° C. for 10 minutes. Heavy chain DNA V-fragments were then isolated according to standard protocols.

Light and heavy chain DNA V-fragments were cloned into the PCR script-CAM (Stratagene) as described by the manufacturer. The sequences were identified by sequencing.

For further subcloning the necessary restriction enzyme recognition sites had to be introduced via PCR. For the light chain V-region DNA the primer pair: maternal mAb vLSacI-S:TGG GAG CTC TGA CAT CGT GCT GAC TCA GTC (SEQ ID NO:56) and maternal mAb vL-Not-AS: ATT GCG GCC GCT TTC AGT TCC AGC TTG GTC C (SEQ ID NO:57) were used. The heavy chain V-region DNA was amplified by PCR introducing the required restriction enzyme recognition sites via the primer pair: maternal mAb vH Sal I: AAA GTC GAC AAA CTG CTG CAG TCT GGG (SEQ ID NO:58) and maternal mAb vH BspEI-AS: ATT TCC GGA TGA GGA GAC TGT GAC CAT G (SEQ ID NO:59).

2.2. Cloning of the Maternal SCA into the Phagemid Vector pComb3H5BHis and Protein Expression Cloning of the VH: For cloning of the maternal VH into the phagemid vector pComb3H5BHis a PCR amplification from the Vector PCR script-CAM containing the maternal VH (see Example 2.1.) was carried out. Amplification was performed according to standard procedures using the 5'-primer MVH8 (5'-GAG GTT CAG CTC GAG CAG TCT GGA GCT-3' (SEQ ID NO:60)) and the 3'-primer 3'-MuVHBstEII (5'-TGA GGA GAC GGT GAC CGT GGT CCC TTG GCC CCA G-3' (SEQ ID NO:61)). The approx 350 bp fragment was identified by agarose gel electrophoresis, purified from the gel and cut with the restriction enzymes BstEII and XhoI. The phagemid pComb3H5BHis (vector described in thesis dissertation of Dr. Ralf Lutterbüee se) was digested with the restriction enzymes SalI and BstEII and the large fragment was ligated with the above mentioned VH fragment via compatible SalI and XhoI nucleotide-overhangs. After transformation into *E. coli* XL1 blue, a single clone was cultivated in 5 mL LB medium (containing 50 µg/mL Carbenicilline) and the plasmid prepared according to standard protocols (designated as: pComb3H5BHis/maternal VH w/o N2). The successful cloning was confirmed by sequencing the insert (Sequiserve, Munich).

Cloning of the VL: For cloning of the maternal VL into the phagemid vector pComb3H5BHis PCR amplification was performed from the Vector PCR script-CAM containing the maternal VL (see Example 2.1). Amplification was performed according to standard procedures using the 5'-primer MuVK3 (5'-CCA GTT CCG AGC TCG TGC TCA CCC AGT CTC CA-3' (SEQ ID NO:62) and the 3'-primer 3'-MuVHK-HindIII-BsiWI (5'-TGG TGC ACT AGT CGT ACG TTT GAT CTC AAG CTT GGT CCC-3' (SEQ ID NO:63)). The approx 350 bp fragment was identified by agarose gel electrophoresis, purified from the gel and cut with the restriction enzymes Sad and SpeI. The phagemid pComb3H5BHis (vector described in thesis dissertation of Dr. Ralf Lutterbüse) was digested with the restriction enzymes SacI and NheI and the large fragment ligated with the above mentioned VL fragment via compatible SpeI and NheI nucleotide-overhangs. After transformation into *E. coli* XL1 blue, a single clone was cultivated in 5 mL LB medium (containing 50 µg/mL Carbenicilline) and the plasmid prepared according to standard protocols (designated as: pComb3H5BHis/maternal VL w/o gene III). The successful cloning was confirmed by sequencing the insert (Sequiserve, Munich).

Cloning of the SCA: For cloning of the maternal VL into the phagemid vector pComb3H5BHis/maternal VH w/o N2 (as mentioned above), both plasmids (pComb3H5BHis/maternal VH w/o N2 and pComb3H5BHis/maternal VL w/o gene III) were cut with the restriction enzymes SacI and NotI.

The large VH-containing vector band from the VH-plasmid and the small VL-containing fragment band from the VL plasmid were isolated and ligated.

After ligation the plasmid DNA was transformed into 100 µL heat shock competent *E. coli* XL1 Blue and plated on Carbenicillin LB-Agar. Single colonies were grown in 5 mL LB-Carbenicillin-cultures/20 mM $MgCl_2$ and expression of SCA was induced after six hours by adding Isopropyl-β-D-thiogalactoside (IPTG) to a final concentration of 1 mM followed by incubation at 30° C.

These cells were harvested after 20 hours by centrifugation and typically resuspended in 500 µL PBS. Through four rounds of freezing at −70° C. and thawing at 37° C. the outer membrane of the bacteria was destroyed by temperature shock so that the soluble periplasmic proteins including the SCA fusion-proteins were released into the liquid. After elimination of intact cells and cell-debris by centrifugation, the supernatant was evaluated by ELISA.

In a first ELISA assay the periplasmic extracts were tested for binding to immobilized recombinant human GM-CSF (Leukomax, Novartis, *E. coli* material).

50 µL of a 1 µg recombinant human GM-CSF/mL PBS solution was coated onto the wells of a 96-well ELISA plate. Coating was typically performed over night at 4° C. After washing the wells once with PBS/0.05% Tween, the wells were blocked with 200 µL PBS/3% BSA per well for 1 h at room temperature. Then, 50 µL of the respective periplasmic preparations or of the murine anti-human GM-CSF antibody 7A6 (0.5 µg/mL PBS) as a positive control were added to the wells and incubated for another hour at room temperature.

Detection of SCA-fragments bound to immobilized recombinant human GM-CSF antigen was carried out using a Penta-His antibody (Qiagen, 1 µg/mL PBS) detected with horseradish peroxidase-conjugated goat anti-mouse IgG Fab2 (Jackson, 1 µg/mL PBS). The signal was developed by adding ABTS substrate solution and detected at a wavelength of 405 nm.

In contrast to the strong signal of the positive control murine mAB 7A6, none of the periplasmic preparations potentially containing the maternal SCA showed a binding signal (FIG. 1). The detected signals were only in the range of PBS and an irrelevant SCA as negative controls.

To determine whether there was any SCA protein at all in the periplasmic extracts, 50 µL of the crude periplasmic extracts were coated directly onto the wells of a 96-well ELISA plate at 4° C. overnight. As described above, the wells were washed, blocked and positive binding detected.

In contrast to the positive control murine mAb 7A6 and the periplasmic preparation containing an irrelevant SCA ("neg. SCA"), some of the periplasmic preparations containing the maternal SCA showed some positively, indicating the presence of the His-tagged SCA (as depicted in FIG. 2). All values were normalized against a PBS control. Although there is an indication of periplasmically produced maternal SCA, the detected signals could also be due to a contamination with cracked cytoplasmic contents including misfolded SCA in inclusion bodies.

To rule out the possibility that the missing binding activity of the maternal SCAs expressed in *E. coli* periplasm is due to a non-functional nucleic acid molecule derived from a cloning artefact, the clone 8 was used for plasmid preparation. Clone 8 was chosen because of its poor ELISA signal and, therefore, its assumed potential of not having a correct SCA sequence. The respective DNA sequence of the maternal SCA clone was confirmed by sequencing and did not show any indication of incorrect cloning or nonfunctional expression due to DNA aberrations.

2.3. Cloning of the Maternal SCA Into the Vector pBAD-HisA for Cytoplasmic Expression and Inclusion Body Production For the expression of the maternal SCA in the insoluble inclusion body fraction of *E. coli*, the gene coding for the maternal SCA was subcloned into the pBAD expression plasmid. The maternal SCA gene was cut using the restriction enzymes NcoI and NotI and was cloned into the vector pBAD-HisA which had been precut using NcoI and NotI, thereby resulting in the expression plasmid pBAD-maternal SCA-HisA.

2.4. Refolding of Maternal SCA from Inclusion Bodies

The aim of this experiment is the production of insoluble protein in inclusion bodies in *E. coli* and the refolding of said insoluble protein from inclusion bodies.

For the production of inclusion bodies of the maternal SCA, BL21 DE3 (Novagen, USA) were transformed with the expression plasmid pBAD-maternal SCA-HisA. Single colonies were used for inoculation of 60 mL of selective medium overnight. For the production culture, 500 mL of selective medium were inoculated with a 1:50 dilution of the cell culture grown overnight. Cells were grown shaking at 37° C. to reach an optical density at 600 nm of 0.75. Induction of protein production was initiated by addition of 0.2% L-arabinose to the cell culture. After four hours of induction of protein production at 37° C. the cells were harvested by centrifugation and the cell pellet was used for the inclusion body purification.

For the purification of the inclusion bodies the cell pellet was resuspended in 10 mL of lysis buffer containing 50 mM Tris-HCl, pH 8.0, 2 mM EDTA and 100 µg/mL lysozyine. The resuspended cells were exposed to three freeze (−80° C.)-thaw (37° C.) cycles. After the third thaw, DNAse and $MgSO_4$ were added to final concentrations of 20 µg/mL, and the culture was subsequently incubated at 37° C. for 30 min. The samples were spun at approximately 20000 g for 30 min to separate inclusion body material from the soluble cellular proteins. The protein was then solubilized in 5 mL solubilization buffer (6 M GuHCl, 200 mM NaCl, 100 mM Tris-HCl and 1 mM EDTA, pH 8.3). Ten mM beta-mercaptoethanol was added to the solubilized inclusion bodies and the solution was incubated overnight at 4° C. The sample was spun at approximately 25000 g for 30 min to remove any insoluble material.

The refolding of the inclusion bodies was performed as previously described (Sinacola, J. R.; Robinson, A. S., Protein Expression and Purification 26 (2002) 301-8) using the controlled dilution/filtration (CDF) method. Five mL of solubilized and reduced SCA was transferred to a standard 200 mL ultrafiltration stirred cell (Amicon) containing a water-washed polyethersulfone membrane with a nominal molecular weight limit of 10 kDa (Millipore). Cycles of solubilization buffer addition (equal to sample volume) followed by filtration at 25-30 psig to the original sample volume (5 mL) were repeated at room temperature until the reducing agent concentration was reduced 1000-fold, requiring approximately 45 min. The stirred cell was transferred to a 4° C. room and connected to a HPLC pump. Cold buffer containing 200 mM NaCl, 100 mM Tris-HCl and 1 mM EDTA at pH 8.3 (salt buffer) was slowly pumped into the stirred cell to reduce the denaturant concentration by dilution in a controlled manner. The guanidine hydrochloride concentration was reduced to 2 M by a constant rate of salt buffer addition over 100 min. Addition of buffer containing 800 mM L-arginine, 200 mM NaCl, 100 mM Tris-HCl, 1 mM EDTA and 750 µM GSSG at pH 8.3 at a constant rate over 1 h was used to transition the sample from 2 to 1 M guanidine hydrochloride. The guanidine hydrochloride concentration was then reduced to 0.25 M over a 90 min period by a constant rate of addition of the original buffer lacking the folding additives. The sample was then concentrated via ultrafiltration to its original volume in an ice water bath. Cycles of salt buffer addition (equal to sample volume) followed by filtration to the original volume were repeated approximately every 5 min to reduce the guanidine hydrochloride concentration to less than 1 mM. After the final filtration step, the sample was allowed to stir in the ice water for several minutes before removal from the stirred cell. The sample was briefly stored at 4° C., prior to analysis.

2.5. Characterization of Functionality of Maternal mAb and Maternal SCA 2.5.1 Binding to Recombinant Human GM-CSF (rhGM-CSF) as Determined by Surface Plasmon Resonance (SPR)

The aim of this experiment is the functional characterization of the maternal mAb and the derived maternal SCA with respect to their binding properties to the native antigen hGM-CSF. Equilibrium and kinetic binding experiments were performed using surface plasmon resonance on the BIAcore™ 2000, Biacore AB (Uppsala, Sweden) with a flow rate of 5 µL/min and HBS-EP (0.01 M HEPES, pH 7.4, 0.15 M NaCl, 3 mM EDTA, 0.005% surfactant P20) as running buffer at 25° C. rhGM-CSF produced in *E. coli* was immobilized onto flow cells 2-4 on a CM5 sensor chip. The chip surface was activated injecting 80 µL of 0.1 M sodium-hydroxysuccinimid, 0.4 M N-ethyl-N'(3-dimethylaminepropyl)-carbodiimid (NHS/EDC). The antigen was coupled by manual injection of 10 µg/mL rhGM-CSF in 0.01 M sodium-acetate, pH 4.7. Different densities of antigen were immobilized on flow cells 2-4 adjusting the amount of manual injection times. Flow cell 1 was left unmodified while flow cell 2 was coated with the highest density of rhGM-CSF (800 RU). Flow cell 3 was coated with 50% of the amount of antigen immobilized on flow cell 2 and flow cell 4 was coated with lowest density of rhGM-CSF (typically 10%). The activated surface of the sensor chip was blocked injecting 85 µL of 1 M ethanolamine and the chip was left to equilibrate overnight with a constant flow of 5 µL/min of HBS-EP.

Equilibrium binding of the maternal mAb and refolded maternal SCA protein was measured by injecting 10 µL of protein solution at concentrations ranging from 1 mg/mL to 6 ng/mL and monitoring the dissociation at 25° C. for 100 sec. Protein was buffered in HBS-EP. The non-specific background adsorption of protein to the unmodified sensor chip surface (FC1) was subtracted from the response signal in the rhGM-CSF immobilized flow cells (FC2, FC3, FC4). The relative response signal (FC2-1, FC3-1, FC4-1) was determined after 100 sec of dissociation and plotted against the respective protein concentration. The data were fitted for half maximal binding at equilibrium (KD) using the Prism software (FIG. 3).

The maternal mAb binds to the immobilized rhGM-CSF with an apparent equilibrium binding constant KD of 5 µg/mL (30 nM). The binding of the mab derived maternal SCA could not be determined with sufficient accuracy. The quality of the available soluble material expressed in the periplasm as well as refolded from inclusion bodies of *E. coli* did not suffice for reliable equilibrium. Nor could kinetic affinity measurements by SPR be made.

2.5.2 Binding to rhGM-CSF by Maternal, Refolded SCA Determined by ELISA

The aim of this experiment was to show with the very limited amount of protein that was available from refolding experiments that the maternal SCA exhibits some residual binding properties of the parent maternal mAb. The sensitivity of the binding experiment via ELISA is higher as compared to the SPR measurements due to the signal amplification that is intrinsic to the ELISA setup.

ELISA experiments were carried out by coating the rhGM-CSF onto wells of 96-well plastic plates (Nunc, maxisorb) typically at 4° C. overnight. The antigen was then removed, wells washed once with PBS/0.05% Twee 20 and subsequently blocked with PBS/3% BSA for at least one hour. After removal of the blocking solution, refolded maternal SCA and SCA controls were added to the wells and incubated for typically one hour at room temperature. The wells were then washed three times with PBS/0.05% Tween 20. Detection of SCA and control antibodies bound to immobilized antigen was carried out using a monoclonal murine anti-His6 antibody (Qiagen anti-PentaHis typically at a final concentration of 1 µg/mL PBS) detected with a peroxidase-labeled polyclonal goat anti-(mouse Fab-fragment) antibody (Dianova, 1 µg/mL PBS). The signal was developed by adding ABTS substrate solution and measured at a wavelength of 405 nm.

Background reaction of an unrelated sample SCA with the coated antigen was determined (neg. control) as well as specific binding of an SCA known to interact with high specificity with the rhGM-CSF (pos. control) (FIG. 4). The refolded maternal SCA shows a clear binding signal to the antigen rhGM-CSF.

2.5.3 Inhibition of rhGM-CSF Dependent Proliferation of TF-1 Cells by Maternal mAb and Maternal SCA The aim of this experiment is the characterization of the maternal mAb and maternal SCA neutralization activity with the hGM-CSF dependant cell line TF-1 (DSMZ ACC 334). TF-1 cells were cultivated in RPMI 1640 medium GIBCO (L-glutamine, phenol-red free), 10% heat inactivated FCS in the presence of 2.5 ng/mL rhGM-CSF as described by the distributor (Deutsche Sammlung von Mikroorganismen und Zellkulturen GmbH, Braunschweig, Germany). Cells were grown to a cell density of 0.5×10exp6 cells/mL. For the proliferation assay TF-1 cells were harvested by centrifugation at 180×g for 4 min. and washed with 1× PBS (Dulbecco's, GIBCO). Cells were resuspended at a final concentration of 1×10exp5 cells/mL in RPMI 1640, 10% FCS and 90 µL cell suspension per Microtest flat bottom cell culture plate well were used (0.9×10exp4 cells/well). A final concentration of 0.3 ng/mL rhGM-CSF was used to stimulate the proliferation of the TF-1 cells. For neutralization of GM-CSF dependent proliferation maternal mAb in 1× PBS was added in a dilution series with final protein concentrations ranging from 30 ng/mL to 1 pg/mL. TF-1 cells were incubated at 37° C. at 5% $CO_2$ for 72 h. After 72 h the proliferative status of the TF-1 cells was determined with a colorimetric assay based on the cleavage of tetrazolium salts (WST-1, Roche) by mitochondrial dehydrogenase in viable cells. The formazan dye formed by metabolically active cells was quantitated by measuring its absorbance with an ELISA reader at 450 nm. The absorption (A) at 450 nm was plotted against the determined protein concentration. The data were fitted for half maximal inhibition of proliferation ($IC_{50}$) using the non-linear regression curve fit of the Prism software (FIG. 5).

The maternal mAb inhibits the rhGM-CSF induced proliferation of the TF-1 cells with an $IC_{50}$ of 1.2 ng/mL (80 pM). The neutralization of the mAb-derived maternal SCA could not be determined with sufficient accuracy. The quality of the available soluble material expressed in the periplasm as well as refolded from inclusion bodies of *E. coli* did not suffice for reliable data on inhibition of GM-CSF dependent TF-1 proliferation. The lack of inhibition of the maternal SCA derived from refolding experiments might be due to an intrinsic instability of the protein that is more exposed to unfolding conditions in the 72 h lasting TF-1 proliferation inhibition experiment at 37° C. that in the ELISA binding experiment where the sample is incubated for less than two hours at 25° C.

2.5.4 Inhibition of Binding of hGM-CSF-FITC to TF-1 Cells by Maternal, Refolded mAb and Maternal SCA The aim of this experiment is to show that the maternal mAb and the derived maternal SCA are capable of inhibiting biding of hGM-CSF to TF-1 cell surface displayed GM-CSF receptor complex. The neutralizing antibody constructs compete for the receptor-binding epitope on the hGM-CSF molecule. The hGM-CSF is no longer able to bind to the TF-1 cell surface displayed hGM-CSF receptor complex. This competitive binding for the same epitope on the antigen is shown by a loss in fluorescence staining of TF-1 cells by fluorescein labelled hGM-CSF (hGM-CSF-FITC) in a flow cytometry-based assay.

For the flow cytometry based assay a final concentration of 0.4 µg/mL hGM-CSF-FITC conjugate in PBS was incubated with maternal mAb in concentrations ranging from 30 µg/mL to 0.014 µg/mL or the refolded maternal SCA. The protein samples were left to equilibrate at 25° C. for 1 h prior to addition of TF-1 cell suspension. The TF-1 were cultivated in RPMI 1640 medium GIBCO (L-glutamine, phenol-red free), 10% heat inactivated FCS in the absence of rhGM-CSF overnight. A final concentration of 2×10exp6 cells/mL and 150 µL of cell suspension was used per sample. The cells were harvested by centrifugation at 500 G at 4° C. for 3 min and washed twice with FACS buffer. The washed cells were resuspended in 100 µL of pre-equilibrated protein sample containing the hGM-CSF-FITC and maternal mAb or maternal SCA respectively. The samples were incubated at 4° C. for 60 min. After two further washes the cells were resuspended in 150 µL ice cold FACS buffer and subsequently analysed by flow cytometry (FIG. 6).

The mean fluorescence intensity (MFI) was plotted against the concentration of the used maternal mAb and maternal SCA. A clear concentration-dependent loss of fluorescence intensity of the TF-1 cells was observed with the maternal mAb. The refolded maternal SCA induced some residual concentration dependent decrease in fluorescence intensity of the hGM-CSF-FITC labelled TF-1 cells, indicating its activity.

The above experiments show that the maternal SCA did in fact have the intended amino acid sequence, since otherwise, no binding signal by ELISA and no competition binding as seen in the TF-1 assay would have been observed for the maternal SCA following refolding. However, the fact that refolding of the maternal SCA from inclusion bodies was necessary before any such behavior could be observed indicates that the maternal SCA as originally expressed in *E. coli* was not recombinantly expressible in soluble form. As such, the maternal mAb represents a "source immunoglobulin" and the maternal SCA represents a "corresponding SCA" in the sense of these terms as used and defined hereinabove.

Example 3

Construction of the Antibody Libraries and Phage Display Selections 3.1 Isolation of RNA from Selected IgD-Positive B-Cells 100 mL blood were taken from five healthy human donors. Peripheral blood mononuclear cells (PBMCs) were isolated by a ficoll-gradient according to standard methods. To select IgD-positive cells, 1 mL anti-mouse IgG-beads (CELLection™ Pan Mouse IgG Kit; DYNAL) were coated with 20 µg mouse anti-human IgD-antibody (PbarMingen). Approximately 2.5×10exp7 PBMCs were added to the beads and incubated at 4° C. for 15 minutes. After washing four times with 1 mL RPMI-medium (BioChrom) IgD-positive cells were released from the beads by adding 8 µL release buffer (DNase) and transferred to a fresh tube. By this method 0.9×10exp5 to 3.7×10exp6 IgD-positive cells could be obtained. Total RNA was isolated from IgD-positive cells using the RNeasy® Midi Kit (QIAGEN) following the manufacturer's instructions. cDNA was synthesized according to standard methods (Sambrook, Cold Spring Harbor Laboratory Press 1989, Second Edition).

3.2 PCR-Amplification of Variable Light Chain Regions (VL-Regions)

For the isolation of light chain V-region DNA, RT-PCR was carried out using V-kappa- (5'-huVK1-SacI-2001 (5'-GAGC-CGCACG AGCCCGAGCT CCAGATGACC CAGTCTCC-3' (SEQ ID NO:64)), 5'-huVK2/4-SacI-2001 (5'-GAGCCG-CACG AGCCCGAGCT CGTGATGACY CAGTCTCC-3' (SEQ ID NO:65)), 5'-huVK3-SacI-2001 (5'-GAGCCG-CACG AGCCCGAGCT CGTGWTGACR CAGTCTCC-3' (SEQ ID NO:66)), 5'-huVK5-SacI-2001 (5'-GAGCCG-CACG AGCCCGAGCT CACACTCACG CAGTCTCC-3' (SEQ ID NO:67)), 5'-huVK6-SacI-2001 (5'-GAGCCG-CACG AGCCCGAGCT CGTGCTGACT CAGTCTCC-3' (SEQ ID NO:68)), 3'-hu-Vk-J1-SpeI-BsiWI (5'-GACGA-CACTA GTTGCAGCCA CCGTACGTTT GATTTCCACC TTGGTCC-3' (SEQ ID NO:69)), 3'-hu-Vk-J2/4-SpeI-BsiWI (5'-GACGACACTA GTTGCAGCCA CCGTACGTTT GATCTCCASC TTGGTCC-3' (SEQ ID NO:70)), 3'-hu-Vk-J3-SpeI-BsiWI (5'-GACGACACTA GTTGCAGCCA CCG-TACGTTT GATATCCACT TTGGTCC-3' (SEQ ID NO:71)), 3'-hu-Vk-J5-SpeI-BsiWI (5'-GACGACACTA GTTGCAGCCA CCGTACGTTT AATCTCCAGT CGT-GTCC-3' (SEQ ID NO:72)) primer sets. RNA from IgD-positive B-cells was transcribed into cDNA (as described above) and used as template DNA in PCR reactions. Per PCR reaction, one 5'-primer was combined with one 3'-primer. The number of different PCR reactions was determined by the number of possible combinations of 5'- and 3'-primers.

The following PCR-program was used for amplification: Denaturation at 94° C. for 15 seconds, primer annealing at 52° C. for 50 seconds and primer extension at 72° C. for 90 seconds were performed over 40 cycles, followed by final extension at 72° C. for 10 minutes. Light chain DNA V-fragments were then isolated according to standard protocols.

3.3 Library Construction—Cloning of the Human VL Pool

A phage display library was generally constructed based on standard procedures, as for example disclosed in "Phage Display: A Laboratory Manual"; Ed. Barbas, Burton, Scott & Silverman; Cold Spring Harbor Laboratory Press, 2001. The primers chosen for PCR amplification gave rise to 5'-SacI and 3'-SpeI recognition sites for the light chain V-fragments. Two ligation reactions were set up, each consisting of 400 ng of the kappa light chain fragments (SacI-SpeI digested) and 1400 ng of the plasmid pBluescript.KS+ (SacI-SpeI digested; large fragment). The two resulting antibody V-light chain pools were then each transformed into 300 µL of electrocompetent *Escherichia coli* XL1 Blue by electroporation (2.5 kV, 0.2 cm gap cuvette, 25 Microfaraday, 200 Ohm, Biorad gene-pulser) resulting in a library size of 5.8×10exp8 independent clones in total.

Kappa (light chain) DNA-fragments from the different PCR amplifications were weighted for each ligation as follows: Each 5'-primer defines a specific group. Within these groups the 3'-primers define the subgroups. The subgroups were weighted 1:2:1:1 corresponding to the primers 3'-hu-Vk-J1-SpeI-BsiWI:3'-hu-Vk-J2/4-SpeI-BsiWI:3'-hu-Vk-J3-SpeI-BsiWI:3'-hu-Vk-J5-SpeI-BsiWI. The groups were weighted according to their germline distribution 1:1:1:0.2:0.2 corresponding to the primers 5'-huVK1-Sac-2001:5'-huVK3-Sac-2001:5'-huVK2/4-Sac-2001:5'-huVK5-Sac-2001:5'-huVK6-Sac-2001.

After electroporation the assay was incubated in SOC broth (Fluka) for phenotype expression. The cultures were then incubated each in 500 mL of SB selection medium containing 50 µg/mL Carbenicillin and 2% w/v Glucose overnight. The next day, cells of the cultures were harvested by centrifugation and plasmid preparation carried out using a commercially available plasmid preparation kit (Qiagen).

3.4 Construction of the Antibody Library—Human VL—Maternal VH

A PCR was carried out to amplify the maternal VH from the vector containing the maternal VH for SCA expression described above in example 2. For amplification a PCR protocol was carried out according to standard procedures using the 5'-primer MVH8 (5'-GAG GTT CAG CTC GAG CAG TCT GGA GCT-3' (SEQ ID NO:73)) and the 3'-primer 3'-MuVHBstEII (5'-TGA GGA GAC GGT GAC CGT GGT CCC TTG GCC CCA G-3' (SEQ ID NO:74)).

After purification of the approximately 350 bp amplification product from an analytical agarose gel, the DNA fragment was cut with the restriction enzymes BstEII and XhoI. The phagemid pComb3H5BHis (vector described in thesis dissertation of Dr. Ralf Lutterbüse) was digested accordingly and the large fragment ligated with the above mentioned fragment. After transformation into *E. coli* XL1 blue, a single clone was cultivated in 100 mL SB medium (containing 50 µm Carbenicilline) and the plasmid was prepared according to standard protocols. The successful cloning was confirmed by sequencing the insert (Sequiserve, Munich).

This vector pComb3H5BHis/maternalVH was restricted with the restriction enzymes SacI and SpeI. The large vector fragment was isolated. Plasmid-DNA containing the VK-library from example 3.3 was restricted with the restriction enzymes SacI and SpeI. The small VK fragment band (approx 350 bp) was isolated.

1200 ng of the vector fragment were ligated with 400 ng of the VK fragments and transformed into 300 µL of electrocompetent *E. coli* XL1 Blue by electroporation (2.5 kV, 0.2 cm gap cuvette, 25 MICROFD, 200 Ohm) resulting in a total SCA library size of 2.8×10exp8 independent clones.

After phenotype expression and slow adaptation to Carbenicillin, the antibody library was transferred into SB-Carbenicillin (50 µg/mL) selection medium. The antibody library was then infected with an infectious dose of 1×10exp12 particles of helper phage VCSM13 resulting in the production and secretion of filamentous M13 phage, wherein each phage particle contained single stranded pComb3H5BHis-DNA encoding a half human SCA-fragment and displayed the corresponding SCA-protein as a translational fusion to phage coat protein III.

3.5 Phage Display Selection of a Human VL

The phage library carrying the cloned SCA-repertoire was harvested from the culture supernatant by PEG8000/NaCl precipitation and centrifugation. Then approximately 1×10exp11 to 1×10exp12 SCA phage particles were resuspended in 0.4 mL of PBS/0.1% BSA and incubated with recombinant biotinylated soluble human GM-CSF (produced in *E. coli* as described above in example 1) for 2 h with gentle agitation in a total volume of 0.5 mL (Concentrations. Then 6.7×10exp7 streptavidine magnetic beads (Dynabeads M-280-Streptavidine, Dynal) were added and further incubated under gentle agitation for 30 minutes.

SCA phage that did not specifically bind to the target antigen were eliminated by washing steps with PBS/0.1% BSA. For that purpose the biotinylated antigen-streptavidin bead complexes (with the potential SCA binders) were collected with a magnet and resuspended in 1 mL of the washing solution (one washing step). This washing procedure was repeated up to four times in further rounds.

After washing, binding entities were eluted by using HCl-Glycine pH 2.2. Following neutralization with 2 M Tris pH 12, the eluate was used for infection of a fresh uninfected *E. coli* XL1 Blue culture. To elute remaining high binding entities this step was repeated using HCl-Glycine pH 1.0. This second eluate was again neutralized and used for infection of a fresh uninfected *E. coli* XL1 Blue culture. Both infected *E. coli* cultures were then mixed and cells that were successfully transduced with a phagemid copy, encoding a human SCA-fragment, were again selected for Carbenicillin resistance and subsequently infected with VCMS13 helper phage to start the second round of antibody display and in vitro selection.

After three rounds of production and selection for antigen-binding SCA-displaying phage the culture supernatant were harvested. Later, 5 mL of a fresh *E. coli* XL1 blue culture (OD>1) was infected with the SCA phages from 2 mL of the above mentioned SCA phage containing culture supernatants (after the third round of phage display selection).

After phenotype expression and slow adaptation to Carbenicillin the reinfected antibody library was transferred into SB-Carbenicillin (50 µg/mL) selection medium. The antibody library was then infected with an infectious dose of 1×10exp12 particles of helper phage VCSM13 resulting in the production and secretion of filamentous M13 phage, wherein each phage particle contained single stranded pComb3H5BHis-DNA encoding a half human SCA-fragment and displayed the corresponding SCA-protein as a translational fusion to phage coat protein III. The phage library carrying the cloned SCA-repertoire was harvested from the culture supernatant by PEG8000/NaCl precipitation and centrifugation.

Then approximately 1×10exp11 to 1×10exp12 SCA phages were resuspended in 1.5 mL of PBS/0.1% BSA and split into three equal aliquots (A, B and C).

Fourth round (=first round on Leukine material): A and B were incubated with 10 nM recombinant biotinylated soluble human GM-CSF (Leukine, as described in example 1) for 1 h under gentle agitation in a total volume of 0.5 mL. Then 6.7×10exp7 streptavidine magnetic beads (Dynabeads M-280-Streptavidine, Dynal) were added and further incubated under gentle agitation for 30 minutes. C was incubated with 1 nM recombinant biotinylated soluble human GM-CSF (Leukine, as described in example 1) for 1 h under gentle agitation in a total volume of 0.5 mL. Then 6.7×10exp7 streptavidine magnetic beads (Dynabeads M-280-Streptavidine, Dynal) were added and further incubated under gentle agitation for 30 minutes.

For A, B and C, SCA phage that did not specifically bind to the target antigen were eliminated by washing steps with PBS/0.1% BSA. For that purpose the biotinylated antigen-streptavidine bead complexes (with the potential SCA binders) were collected using a magnet and resuspended in 1 mL of the washing solution (one washing step). This washing procedure was repeated four to ten times.

After washing, binding entities were eluted a) by using HCl-Glycine pH 2.2 and after neutralization with 2 M Tris pH 12, the eluate was used for infection of a fresh uninfected *E. coli* XL1 Blue culture and, subsequently, b) by adding 200 µL of a fresh *E. coli* XL1 Blue directly to the antigen bead complexes for 10 minutes. Both cultures a) and b) were then mixed and cells that successfully transduced with a phagemid copy, encoding a human SCA-fragment, were again selected for Carbenicillin resistance and subsequently infected with VCMS13 helper phage to start the second round of antibody display and in vitro selection.

Two further rounds of selections were carried out for the three antibody libraries A, B and C. Antigen concentrations were decreased during selection to the final concentrations as follows:

Library A: fifth round (=second round on Leukine material) 10 nM, sixth round (=third round on Leukine material) 1 nM.

Library B: fifth round (=second round on Leukine material) 1 nM, sixth round (=third round on Leukine material) 0.1 nM.

Library C: fifth round (=second round on Leukine material) 0.1 nM, sixth round (=third round on Leukine material) 0.1 nM.

Plasmid DNA corresponding to 4, 5 and 6 rounds of panning was isolated from *E. coli* cultures. For the production of soluble SCA-protein, VL-DNA fragments were excised from the plasmids (SacI-SpeI), and cloned via the same restriction sites in the plasmid pComb3H5BFlag/His with the maternal VH differing from the initial pComb3H5BHis/maternal VH in that it adds to the expression construct (e.g. SCA) a Flag-tag (TGDYKDDDDK (SEQ ID NO:75)) between the SCA and the His6-tag and having the phage gene III and the N2 domain deleted.

After ligation each pool (different rounds of panning) of plasmid DNA was transformed into 100 μL heat shock competent E. coli TG1 and plated on Carbenicillin LB-Agar. Single colonies were picked into 120 μL of LB carb (50 μg/mL) 1% glucose in 96-well plates (Greiner). The wells were sealed with a semipermeable membrane (Greiner) and the plates were incubated in a shaking incubator overnight at 37° C. (master plate).

Then, 10 μL of the master plate cultures were transferred into a second 96-well plate (working plate) containing 90 μL LB carb (50 μg/mL) 0.1% glucose per well. After incubation for 4 h in a 37° C. shaking incubator, SCA production was induced by adding 20 μL LB carb 6 mM IPTG to each well. After another incubation step overnight at 30° C. under shaking, cell were lysed in a 1 h room temperature incubation with 40 μL lysis buffer (400 mM boric acid, 320 mM NaCl, 4 mM EDTA pH 8, 2.5 mg/mL lysozyme). Residual cells and cell debris were separated by centrifugation for 12 minutes at 2500 rpm (Hettich). The SCA-containing supernatants were then tested for binding in ELISA assays.

Detection of SCA-fragments bound to immobilized recombinant human GM-CSF antigen (Leukine) was carried out using a biotinylated anti-flag M2 (1 μg/mL PBS/1% BSA) detected with horseradish peroxidase-conjugated goat anti mouse Fab2 specific polyclonal antibody (Dianova, 1 μg/mL PBS/1% BSA). The signal was developed by adding ABTS substrate solution and detected at a wavelength of 405 nm.

From approximately 500 clones tested, most lysates showed strong ELISA signals in contrast to PBS as negative control on the recombinant antigen. The first 96 lysates were tested in a parallel experiment for unspecific binding to the blocking agent and no GM-CSF antigen. No significant detectable signal could be observed, indicating the specificity of the binding to the recombinant human GM-CSF. FIGS. 7 & 8 are illustrative of typical ELISA results.

The fact that SCAs were obtained that specifically bind to the human GM-CSF antigen clearly demonstrates that such SCAs produced using the method of the present invention were recombinantly solubly expressible. This is in stark contrast to the maternal SCA (i.e. the "corresponding antibody fragment" as defined hereinabove) which, after direct conversion from the source immunoglobulin but prior to performing the method of the invention, was not recombinantly solubly expressible. As such, the present results show that a "corresponding antibody fragment" which was originally not recombinantly solubly expressible was rendered so by employing the method of the invention.

3.6 Isolation of RNA from Pheripheric Blood Mononuclear Cells (PBMCs)

100 mL blood were taken from five healthy human donors. Peripheral blood mononuclear cells (PBMCs) were isolated by a ficoll-gradient according to standard methods. Total RNA was isolated from PBMCs using the RNeasy® Midi Kit (QIAGEN) following the manufacturer's instructions. cDNA was synthesized according to standard methods (Sambrook, Cold Spring Harbor Laboratory Press 1989, Second Edition).

3.7 PCR-Amplification of Variable Heavy Chain Regions (VH-Regions)

3.7.1 Amplification of Human VH Fragments

For the isolation of human VH-regions, RT-PCR was carried out using a 5'-VH-specific primer set (5'-huVH1,3,5-XhoI-2001 (5'-AGG TGC AGC TGC TCG AGT CTG G-3' (SEQ ID NO:76)), 5'-huVH2-XhoI-2001 (5'-CAG RTC ACC TTG CTC GAG TCT GG-3' (SEQ ID NO:77)), 5'-huVH4-XhoI-2001 (5'-CAG GTG CAG CTG CTC GAG TCG GG-3' (SEQ ID NO:78)), 5'-huVH4B-XhoI-2001 (5'-CAG GTG CAG CTA CTC GAG TGG GG-3' (SEQ ID NO:79)), 5'-huVH6-XhoI-2001 (5'-CAG GTA CAG CTG CTC GAG TCA GG-3' (SEQ ID NO:80)) and a set of two 3'-VH-specific primers (3'-hu-VH-BstEII-2001 (5'-CTG AGG AGA CGG TGA CC-3' (SEQ ID NO:81)), 3'-hu-VH-J3-BstEII-2001 (5'-CTG AAG AGA CGG TGA CC-3' (SEQ ID NO:82)). Per PCR reaction, one 5'-primer was combined with one 3'-primer; the number of different PCR reactions was determined by the number of possible combinations of 5'- and 3'-primers. The following PCR-program was used for amplification: Denaturation at 94° C. for 15 seconds, primer annealing at 52° C. for 50 seconds and primer extension at 72° C. for 60 seconds was performed over 40 cycles, followed by final extension at 72° C. for 10 minutes.

3.7.2 Amplification of Human Lib 134-VH Fragments

The second VH library was constructed and named Lib 134-VH. This VH-library consists of the human repertoire of FR1-CDR2-FR2-CDR2-FR3 from the PCR amplified VH-regions of the above described PBMC pool, linked operatively to the VH CDR3 of the maternal antibody followed by a human FR4 germline sequence.

For the isolation of human template VH-regions, RT-PCR was carried out using a 5'-VH-specific primer set (5'-huVH1,3,5-XhoI-2001 (5'-AGG TGC AGC TGC TCG AGT CTG G-3' (SEQ ID NO:76)), 5'-huVH4-XhoI-2001 (5'-CAG GTG CAG CTG CTC GAG TCG GG-3' (SEQ ID NO:78)), 5'-huVH4B-XhoI-2001 (5'-CAG GTG CAG CTA CTC GAG TGG GG-3' (SEQ ID NO:79)) and a set of two 3'-VH-specific primers (3'-hu-VH-BstEII-2001 (5'-CTG AGG AGA CGG TGA CC-3' (SEQ ID NO:81)), 3'-hu-VH-J3-BstEII-2001 (5'-CTG AAG AGA CGG TGA CC-3' (SEQ ID NO:82)). Per PCR reaction, one 5'-primer was combined with one 3'-primer; the number of different PCR reactions was determined by the number of possible combinations of 5'- and 3'-primers. The PBMC cDNA (as described above of four donors only was used as a source of VH-genes). The following PCR-program was used for amplification: Denaturation at 94° C. for 15 seconds, primer annealing at 52° C. for 50 seconds and primer extension at 72° C. for 60 seconds was performed over 40 cycles, followed by final extension at 72° C. for 10 minutes. The amplificates with a size of approximately 350 bp were isolated according to standard methods.

For the isolation of Lib 134-VH-regions, RT-PCR was carried out in two steps. First, the human heavy chain VH-segments (FR1-CDR2-FR2-CDR2-FR3) were PCR-amplified from the isolated template VH fragments using the same 5'-VH-specific primer set as described above(5'-huVH1,3,5-XhoI-2001, 5'-huVH4-XhoI-2001, 5'-huVH4B-XhoI-2001) and a 3'-specific primer set (3'-Lib 134-VH-1A-MH3 (5'-GTA ATC AAA GTA GAC TGC TAT CAG ACC CGA TCT YGC ACA GTA ATA CAC GGC-3' (SEQ ID NO:83)), 3'-Lib 134-VH-1B-MH3 (5'-GTA ATC AAA GTA GAC TGC TAT CAG ACC CGA TCT YGC ACA GTA ATA CAY RGC-3' (SEQ ID NO:84)), 3'-Lib 134-VH-3A-MH3 (5'-GTA ATC AAA GTA GAC TGC TAT CAG ACC CGA TCT NGY ACA GTA ATA CAC RGC-3' (SEQ ID NO:85)), 3'-Lib 134-VH-3B-MH3 (5'-GTA ATC AAA GTA GAC TGC TAT CAG ACC CGA TCT NGC ACA GTA ATA CAA RGC-3' (SEQ ID NO:86)), 3'-Lib 134-VH-4-MH3 (5'-GTA ATC AAA GTA GAC TGC TAT CAG ACC CGA TCT SGC ACA GTA ATA CAC RGC-3' (SEQ ID NO:87)) for the human VH subfamilies 1, 3 and 4 matching in the very terminal region of FR3.

The following primer combinations were used:
a) 5'-huVH1,3,5-XhoI-2001×3'-Lib 134-VH-1A-MH3
b) 5'-huVH1,3,5-XhoI-2001×3'-Lib 134-VH-1B-MH3
c) 5'-huVH1,3,5-XhoI-2001×3'-Lib 134-VH-3A-MH3
d) 5'-huVH1,3,5-XhoI-2001×3'-Lib 134-VH-3B-MH3
e) 5'-huVH4-XhoI-2001×3'-Lib 134-VH-4-MH3
f) 5'-huVH4B-XhoI-2001×3'-Lib 134-VH-4-MH3

Per PCR reaction, one 5'-primer was combined with the 3'-primer; the number of different PCR reactions was determined by the number of possible combinations of 5'- and the 3'-primer. The following PCR-program was used for amplification: Denaturation at 94° C. for 15 seconds, primer annealing at 52° C. for 50 seconds and primer extension at 72° C. for 90 seconds was performed over 40 cycles, followed by final extension at 72° C. for 10 minutes. Through this PCR step and the respective 3'-primer sequence, the human VH segments are prolonged for a part of the maternal VH CDR3, which then in turn is the priming site for the second step PCR 3'-primer.

These VH-(FR1-CDR2-FR2-CDR2-FR3) DNA-fragments were then used as templates in this second PCR reaction using again the respective 5'VH-specific primer and an universal 3' primer matching to the universal 3'-terminus of the amplified DNA-fragments (3'-Lib 134-JH3-BstE2, 5'-AGA GAC GGT GAC CAT TGT CCC TTG GCC CCA GTA ATC AAA GTA GAC TGC-3' (SEQ ID NO:88)).

The following PCR-program was used for amplification: Denaturation at 94° C. for 15 seconds, primer annealing at 52° C. for 50 seconds and primer extension at 72° C. for 60 seconds were performed over 40 cycles, followed by final extension at 72° C. for 10 minutes. The DNA V-fragments were isolated according to standard protocols.

3.8 Library Construction—Cloning of the Human VH Pool

In a second round of the foregoing method, one VL identified in the first, previous round was chosen, and subsequently combined with a library of human VH fragments with the aim of generating a "second antibody fragment". A phage display library was generally constructed based on standard procedures, as for example disclosed in "Phage Display: A Laboratory Manual"; Ed. Barbas, Burton, Scott & Silverman; Cold Spring Harbor laboratory Press, 2001.

3.8.1 Cloning of Human VH Fragments

Heavy chain DNA fragments were first subcloned into pBluescript KS vector (Stratagene). To this end, 400 ng of VH fragments (XhoI-BstEII digested) were each ligated with 1200 ng pBluescript KS (XhoI-BstEII digested) and transformed into electrocompetent E. coli XL1 Blue by electroporation (as described for the light chains) resulting in a library of 3.4×10exp8 independent clones in total.

Heavy chain DNA-fragments from the different PCR amplifications were weighted for each ligation as follows: Each 5'-primer defines a specific group. Within these groups the 3'-primers define the subgroups. The subgroups were weighted 3:1 corresponding to the primers 3'-hu-VH-BstEII-2001:3'-hu-VH-J3-BstEII. The groups were weighted according to their germline distribution 7:1:1:1:0.3 corresponding to the primers 5'-huVH1,3,5-XhoI-2001:5'-huVH2-XhoI-2001:5'-huVH4-XhoI-2001:5'-huVH4B-XhoI-2001:5'-huVH6-XhoI-2001.

One ligation reaction was set up, consisting of 400 ng of human VH fragment pool (from the pBluescrip/VH as mentioned above, XhoI-BstEII digested) and 1200 ng of the plasmid pComb3H5BHis/B32oN-45VL ((the B32oN-45VL nucleic acid molecule was cloned via the restriction sites SacI and SpeI into pComb3H5BHis according to standard procedures) XhoI-BstE2 digested; large fragment). The resulting antibody human VH pool was then transformed into 300 µL of electrocompetent Escherichia coli XL1 Blue by electroporation (2.5 kV, 0.2 cm gap cuvette, 25 microFD, 200 Ohm, Biorad gene-pulser) resulting in a library size of 1.1×10exp9 independent clones in total.

After electroporation the assay was incubated in SOC for phenotype expression. The cultures were then incubated each in 500 mL of SB selection medium containing 50 µg/mL Carbenicillin and 2% v/v Glucose overnight. The next day, cells of the cultures were harvested by centrifugation and plasmid preparation carried out using a commercially available plasmid preparation kit (Qiagen) to preserve the DNA library.

1.5 µg of this plasmid pool encoding the respective SCA pool were then electroporated into E. coli XL1blue (2.5 kV, 0.2 cm gap cuvette, 25 microFD, 200 Ohm, Biorad gene-pulser) resulting in a library size of 2.0×10exp9 independent clones in total.

After phenotype expression and slow adaption to Carbenicillin the antibody library was transferred into SB-Carbenicillin (50 µg/mL) selection medium. The antibody library was then infected with an infectious dose of 1×10exp12 particles of helper phage VCSM13 resulting in the production and secretion of filamentous M13 phage, wherein each phage particle contained single stranded pComb3H5BHis-DNA encoding a human SCA-fragment and displayed the corresponding SCA-protein as a translational fusion to phage coat protein III.

3.8.2 Cloning of Human Lib134-VH Fragments

Heavy chain DNA-fragments from the different PCR amplifications were weighted for each ligation as follows:
a:b:c:d:e:f=3:1:3:1:1:1, wherein a-f have the following meanings:
a) 5'-huVH1,3,5-XhoI-2001×3'-Lib 134-VH-1A-MH3×3'-Lib 134-JH3-BstE2
b) 5'-huVH1,3,5-XhoI-2001×3'-Lib 134-VH-1B-MH3×3'-Lib 134-JH3-BstE2
c) 5'-huVH1,3,5-XhoI-2001×3'-Lib 134-VH-3A-MH3×3'-Lib 134-JH3-BstE2
d) 5'-huVH1,3,5-XhoI-2001×3'-Lib 134-VH-3B-MH3×3'-Lib 134-JH3-BstE2
e) 5'-huVH4-XhoI-2001×3'-Lib 134-VH-4-MH3×3'-Lib 134-JH3-BstE2
f) 5'-huVH4B-XhoI-2001×3'-Lib 134-VH-4-MH3×3'-Lib 134-JH3-BstE2

One ligation reaction was set up consisting of 400 ng of human Lib 134-VH fragment pool (XhoI-BstE2I digested) and 1200 ng of the plasmid pComb3H5BHis/B32oN-45VL ((the B32oN-45VL nucleic acid molecule was cloned via the restriction sites SacI and SpeI into pComb3H5BHis according to standard procedures) XhoI-BstE2 digested; large fragment). The resulting antibody human VH pool was then transformed into 300 µL of electrocompetent Escherichia coli XL1 Blue by electroporation (2.5 kV, 0.2 cm gap cuvette, 25 Microfaraday, 200 Ohm, Biorad gene-pulser) resulting in a library size of 1.6×10exp8 Lib independent clones in total.

After electroporation the assay was incubated in SOC broth (Fluka) for phenotype expression. The cultures were then incubated each in 500 mL of SB selection medium containing 50 µg/mL Carbenicillin and 2% v/v Glucose overnight. The next day, cells of the cultures were harvested by centrifugation and plasmid preparation carried, out using a commercially available plasmid preparation kit (Qiagen) to preserve the DNA library.

1.5 µg of this plasmid pool encoding the respective SCA pool were then electroporated into E. coli XL1blue (2.5 kV, 0.2 cm gap cuvette, 25 microFD, 200 Ohm, Biorad gene-pulser) resulting in a library size of 2.4×10exp9 independent clones in total. After phenotype expression and slow adaption to Carbenicillin the antibody library was transferred into SB-Carbenicillin (50 µg/mL) selection medium. The antibody library was then infected with an infectious dose of 1×10exp12 particles of helper phage VCSM13 resulting in the production and secretion of filamentous M13 phage, wherein each phage particle contained single stranded pComb3H5BHis-DNA encoding a (mostly) human SCA-fragment and displayed the corresponding SCA-protein as a translational fusion to phage coat protein III.

3.9 Phage Display Selection for a Human VH

The phage libraries from 3.8.1 and 3.8.2 carrying the cloned SCA-repertoire was harvested from the culture supernatant by PEG8000/NaCl precipitation and centrifugation.

The same protocol was carried out for both libraries:

Approximately 1×10exp11 to 1×10exp12 SCA phages were resuspended in 0.4 mL of PBS/0.1% BSA and incubated with a) recombinant biotinylated soluble human GM-CSF (*E. coli* material, as described in example 1) and b) recombinant biotinylated soluble human GM-CSF (Leukine, as described in example 1) for 1 h under gentle agitation in a total volume of 0.5 mL. Then 6.7×10exp7 streptavidine magnetic beads (Dynabeads M-280-Streptavidine, Dynal) were added and further incubated under gentle agitation for 30 minutes.

SCA phage that did not specifically bind to the target antigen were eliminated by washing steps with PBS/0.1% BSA. For that purpose the biotinylated antigen-streptavidine bead complexes (with the potential SCA binders) were collected via a magnet and resuspended in 1 mL of the washing solution (one washing step). This washing procedure was repeated up to four times. After washing, binding entities were eluted by using HCl-Glycine pH 2.2 and after neutralization with 2 M Tris pH 12, the eluate was used for infection of a fresh uninfected *E. coli* XL1 Blue culture.

To elute remaining high binding entities the beads were resuspended directly in 200 µL of a fresh *E. coli* XL1 blue culture (OD600≧0.5) and incubated for 10 minutes under gentle agitation. Both cultures were then mixed and cells successfully transduced with a phagemid copy, encoding a human SCA-fragment, were again selected for Carbenicillin resistance and subsequently infected with VCMS13 helper phage to start the second round of antibody display and in vitro selection.

A total of 4 rounds of selections were carried out for the two antibodies. Antigen concentrations were decreased during selection to the final concentrations as follows:

| | |
|---|---|
| 1. round | 100 nM |
| 2. round | 10 nM |
| 3. round | 10 nM |
| 4. round | 10 nM |

Plasmid DNA from *E. coli* cultures was isolated corresponding to 3 and 4 rounds of panning.

For the production of soluble SCA-protein the VH-VL-DNA fragments were excised from the plasmids (Xho-SpeI), and cloned via the same restriction sites in the plasmid pComb3H5BFlag/His (w/o N2 domain). After ligation each pool (different rounds of panning) of plasmid DNA was transformed into 100 µL heat shock competent *E. coli* TG1 and plated on Carbenicillin LB-Agar. Single colonies were picked and inoculated into 120 µL of LB carb (50 µg/mL) 1% glucose in 96-well plates (Greiner). The wells were sealed with a semipermeable membrane (Greiner) and the plates incubated overnight at 37° C. in a shaking incubator (master plate).

Then, 10 µL of the master plate cultures were transferred into a second 96 well plate (working plate) containing 90 µL LB carb (50 µg/mL) 0.1% glucose per well. After incubation for 4 h in a 37° C. shaking incubator, SCA production was induced by adding 20 µL LB carb 6 mM IPTG to each well. After another incubation step overnight at 30° C. with shaking, cell were lysed in a 1 h room temperature incubation with 40 µL lysis buffer (400 mM boric acid, 320 mM NaCl, 4 mM EDTA pH 8, 2.5 mg/mL lysozyme). Residual cells and cell debris were separated by centrifugation for 12 minutes at 2500 rpm (Hettich).

The SCA containing supernatants were then tested for binding in ELISA assays.

Detection of SCA-fragments bound to immobilized recombinant human GM-CSF antigen (Leukine) was carried out using a biotinylated anti-flag M2 (1 µg/mL PBS/1% BSA) detected with horseradish peroxidase-conjugated goat anti mouse Fab2 specific polyclonal antibody (Dianova, 1 µg/mL PBS/1% BSA). The signal was developed by adding ABTS substrate solution and detected at a wavelength of 405 nm.

From approximately 200 clones tested, at least ⅓ of the lysates showed strong ELISA signals as compared to PBS as a negative control on the recombinant antigen. The lysates were tested in a parallel experiment for unspecific binding to the blocking agent and no GM-CSF antigen. No significant detectable signal could be observed, indicating the specificity of the binding to the recombinant human GM-CSP.

The DNA sequences of more than 20 ELISA-positive SCA clones were determined and most of the clones corresponded to a human VH FR1-CDR1-FR2-CDR2-FR3 polypeptide combined with the maternal VH CDR3 indicating their origin from the Lib 134. Some ELISA-positive clones corresponded to a human polypeptide over the whole VH molecule indicating their origin from the human VH library.

Example 4

Characterization of SCA Hit and Lead Constructs 4.1 Characterisation of SCA Hit Constructs Derived from the Method of Section 3 as Applied to Maternal huVL 4.1.1 Small-scale expression and purification of SCA hits (derived as described above) in *E. coli*

As previously mentioned, *E. coli* TG1 transformed with pComb3H5BFlag/His containing a VL- and VH-segment can produce soluble SCA in sufficient amounts after induction with 1 mM IPTG. The SCA-chain is exported into the periplasm where it folds into a functional conformation. The SCA hits derived as described above were screened for their newly acquired propensity to yield sufficient amounts of soluble, folded, functional, active SCA protein.

For periplasmic preparations the cells were grown in SB-medium supplemented with 20 mM MgCl$_2$ and carbenicillin 50 µg/mL and redissolved in 1 mL PBS after harvesting. By four rounds of freezing at −70° C. and thawing at 37° C., the outer membrane of the bacteria was destroyed by temperature shock and the soluble periplasmic proteins including the SCAs were released into the supernatant. After elimination of intact cells and cell-debris by centrifugation, the supernatant containing the SCAs was collected and used for further examination. These crude supernatants containing SCA will be further termed PPP.

For further purification, 25 µL 20 mM NaH$_2$PO$_4$, 400 mM NaCl, 250 mM Imidazol, pH 7.0 was added to the PPP. The PPP were purified via Ni-NTA Spin Columns (Qiagen) as recommended in the manual. In brief, the PPP solution was added to the pre-equilibrated column to bind to the resin. The Spin Columns were washed twice with 20 mM $NaH_2PO_4$, 400 mM NaCl, 20 mM Imidazol, pH 7.0. The bound protein was eluted twice in 200 μL 20 mM $NaH_2PO_4$, 400 mM NaCl, 250 mM Imidazol, pH 7.0. The purified SCA proteins were further analysed for binding strength (kinetic off rate) and neutralization capabilities (inhibition of GM-CSF dependent TF-1 proliferation). Though not separating and distinguishing between the different possible conformations of the SCA, this crude purification of PPP yields 80% pure SCA protein as judged by Western-blot analysis (data not shown).

4.1.2 Kinetic Binding Analysis of SCA Hits Derived from the Above Method as Determined by SPR The aim of this experiment is to establish a qualitative ranking of the ELISA-positive and expressible SCA hits derived from the method as described above in section 3. The SPR experiment was performed as described in detail in section 2.5.1. Prior to the experiment eluted protein solutions of the PPP were dialyzed against PBS at 25° C. for 2 h and diluted 1:1 in HBS-EP. Binding kinetics of the SCA hits were measured injecting 10 μL of purified PPP protein solution as described in section 4.1.1 at 25° C. over the sensor chip. The non-specific background adsorption of protein to the unmodified sensor chip surface (FC1) was subtracted from the response signal in the rhGM-CSF immobilized flow cells (FC2, FC3, FC4). The relative response signal (FC2-1, FC3-1, FC4-1) was determined and the specific dissociation rate was monitored for 100 sec (FIG. 9).

The amplitude of the binding peak (RUmax) directly correlates to the protein concentration in the injected sample. The kinetic on rate (ka) is concentration dependent and cannot be used for the qualitative ranking of the purified PPP SCA material due to varying concentrations of the PPP protein. The kinetic off rate (kd) is protein concentration independent and characteristic for the binding strength of a respective SCA hit. Almost all expressed and identified SCA hits derived from the method as described above in section 3 show some degree of specific binding to the immobilized rhGM-CSF. The SCA hits with the best apparent off rate were identified and, after further correlation of the SPR data with the inhibition data as described in 4.1.3, submitted for sequencing.

4.1.3 Inhibition of rhGM-CSF-Dependent Proliferation of TF-1 Cells by SCA Hits

The aim of this experiment is to establish a qualitative ranking of the ELISA-positive, expressible and off rate-characterized SCA hits derived from the method in section 3 above for their proliferation-inhibition activity. TF-1 proliferation-inhibition experiments were performed as described in detail in section 2.5.2. Cells were resuspended at a final concentration of 1×10exp5 cells/mL in RPMI 1640, 10% FCS and 90 μL cell suspension per well were used (0.9×10exp4 cells/well). A final concentration of 0.3 ng/mL rhGM-CSF was used to stimulate the proliferation of the TF-1 cells. For neutralization of hGM-CSF-dependent proliferation, purified PPP of the SCA hits were dialyzed against 1× PBS at 25° C. for 2 h. 10 μL of dialyzed and sterile filtered protein solution (0.22 μm filter) was added to 100 μL TF-1 and rhGM-CSF solution. The samples were incubated at 37° C. at 5% $CO_2$ for 72 h. After 72 h the proliferative status of the TF-1 cells was determined adding WST-1 and monitoring the colorimetric change with an ELISA reader at 450 nm (FIG. 10).

The inhibition of the rhGM-CSF dependent proliferation of the TF-1 cells by the SCA constructs is of varying strength. Some SCA constructs do not inhibit the proliferation to a large degree—this can be due to a lack of stable complex formation of the SCA constructs and the rhGM-CSF over the period of 72 h at 37° C. The SCA hits displaying the strongest inhibition of TF-1 proliferation were identified and after correlation of with the SPR data (see section 4.1.2, above) submitted for sequencing.

4.1.4 Sequencing of Identified Neutralizing SCA Hits

Sequencing was carried out at Sequiserve (Munich).

The following different human VL-region sequences were identified (FIGS. 11-35):

| | | |
|---|---|---|
| B32oN-10 (FIG. 11) | B32oN-33 (FIG. 12) | B32oN-44 (FIG. 13) |
| B32oN-45 (FIG. 14) | B32oN-48 (FIG. 15) | B32oN-49 (FIG. 16) |
| B32oN-67 (FIG. 17) | B32oN-73 (FIG. 18) | B33oN-115 (FIG. 21) |
| B33oN-8 (FIG. 26) | B33oN-21 (FIG. 19) | B33oN-22 (FIG. 20) |
| B33oN-35 (FIG. 22) | B33oN-66 (FIG. 23) | B33oN-67 (FIG. 24) |
| B33oN-69 (FIG. 25) | C32oN-10 (FIG. 27) | C32oN-34 (FIG. 29) |
| C32oN-21 (FIG. 28) | C32oN-46 (FIG. 30) | C32oN-89 (FIG. 31) |
| C32oN-92 (FIG. 32) | C33oN-32 (FIG. 33) | C33oN-33 (FIG. 34) |
| C33oN-49 (FIG. 35) | | |

4.2 Characterisation of SCA Lead Constructs Combining a huVL with the VH of the Maternal SCA 4.2.1 Large Scale Production and Purification of SCA Leads Constructs Produced by the Method Described in Example 3

The SCA leads were isolated in a two-step purification process of immobilized metal affinity chromatography (IMAC) and gel filtration. All leads were purified according to this method. Äkta® FPLC System (Pharmacia) and Unicorn® Software were used for chromatography. All chemicals were of research grade and purchased from Sigma (Deisenhofen) or Merck (Darmstadt).

IMAC was performed using a Quiagen Ni-NTA Superflow column according to the protocol provided by the manufacturer. The column was equilibrated with buffer A2 (20 mM sodium phosphate pH 7.2, 0.4 M NaCl) and the PPP (100 mL) was applied to the column (2 mL) at a flow rate of 2 mL/min. The column was washed with 5 column volumes 5% buffer B2 (20 mM sodium phosphate pH 7.2, 0.4 M NaCl, 0.5 M Imidazol) to remove unbound sample. Bound protein was eluted using 100% buffer B2 in 5 column volumes. Eluted protein fractions were pooled for further purification.

Gel filtration chromatography was performed on a HiLoad™ 16/60 Superdex 75 Prep Grade column (Pharmacia) equilibrated with PBS (Gibco). Eluted protein samples (flow rate 1 mL/min) were subjected to standard SDS-PAGE and Western Blot for detection. Prior to purification, the column was calibrated for molecular weight determination (molecular weight marker kit, Sigma MW GF-200). The size dependent separation on the Superdex 75 Prep Grade column resulted in clearly distinguishable monomer and associative dimer peak fractions of the SCA leads. Protein concentrations were determined measuring OD at 280 nm and calculated using the sequence specific molecular extinction coefficient of the respective SCA leads.

4.2.2 Kinetic Binding Analysis of SCA Leads by SPR

The aim of the experiment is the in-depth characterisation of the SCA leads selected with focus on the preserved functionality in comparison to the parent maternal mAb. Binding to the naive antigen—here rhGM-CSF—is one of the attributes the maternal mAb-derived SCA leads.

Binding kinetics (kd and ka) of the SCA leads were measured injecting 10 μL of purified protein in dilution series ranging from 10 μg/mL to 1 pg/mL purified SCA and monitoring the dissociation at 25° C. for 100 sec. Protein was buffered in HBS-EP. The data were fitted using BIAevaluation™ software determining the rate constant for dissociation and association kinetics with a 1:1 Langmuir binding equation (1, 2), where A is the concentration of injected analyte and B is the concentration of the ligand.

$$dB/dt = -(ka*[A]*[B] - kd*[AB])  \quad (1)$$

$$dAB/dt = -(ka*[A]*[B] - kd*[AB])  \quad (2)$$

Kinetic binding curves were determined using up to 8 concentrations of each SCA lead analyzed. The independent fitting of the raw data resulted in dissociation and association rate constants that were used to calculate the equilibrium dissociation constant (KD) (FIGS. 36A, 36B). The data of the maternal SCA B32oN-45 represent a typical sensogram and results are summarized in Table 1. The maternal SCA B32oN-45, derived from the method as described above, demonstrates specific binding to rhGM-CSF with an apparent KD of 50 nM. The binding specificity of the parent maternal mAb with a KD of 30 nM has been preserved in this SCA lead.

4.2.3 Inhibition of thGM-CSF Dependent Proliferation of TF-1 Cells by SCA Leads

After confirming that the strength of specific binding was preserved in the SCA leads described in section 4.2.2, the aim of this experiment was to assess the specificity of the interaction of the SCA lead with the antigen hGM-CSF. The inhibition of the biological function of the antigen hGM-CSF by binding of the SCA was characterized in a TF-1 proliferation-inhibition experiment.

TF-1 proliferation-inhibition experiments were performed as described above in section 2.5.3. Cells were resuspended at a final concentration of 1×10exp5 cells/mL in RPMI 1640, 10% FCS and 90 μL cell suspension per well were used (0.9×10exp4 cells/well). A final concentration of 0.3 ng/mL rhGM-CSF was used to stimulate the proliferation of the TF-1 cells. For neutralization of hGM-CSF dependent proliferation purified SCA in 1× PBS was added in a dilution series with final protein concentrations ranging from 100 μg/mL to 10 pg/mL. 10 μL of dialyzed and sterile filtered protein solution (0.22 μm filter) was added to 100 μL TF-1 and rhGM-CSF solution. The samples were incubated at 37° C. at 5% $CO_2$ for 72 h. After 72 h the proliferative status of the TF-1 cells was determined adding WST-1 and monitoring the calorimetric change with an ELISA reader at 450 nm (FIG. 37).

The half maximal inhibition constant ($IC_{50}$) of the maternal SCA B32oN-45, generated by the method described above, is 6 nM. The $IC_{50}$s of the characterized SCA leads are in the same nanomolar inhibition range, implying the potential of the methodology as described in Example 3. The selected and characterized SCAs all preserve the binding specificity (KD determined by SPR as described in section 4.2.2) and neutralization potential of the parent maternal mAb (i.e. the "source immunoglobulin"). In addition to preservation of the original functional specificities of the parent maternal mAb the SCA leads produced via the method of Example 3 show satisfying expression and folding properties that were not observed in the original maternal SCA (i.e. the "corresponding antibody fragment").

TABLE 1

| | ka (1/Ms) | kd (1/s) | Conc of analyte (nM) | KA (1/M) | KD (M) |
|---|---|---|---|---|---|
| SCA B32ON-45 | 5.43exp4 | 5.14exp−3 | 3120 | 1.06exp7 | 9.46exp−8 |
| SCA B32ON-45 | 8.71exp4 | 4.6exp−3 | 1040 | 1.89exp7 | 5.28exp−8 |
| SCA B32ON-45 | 4.4exp5 | 4.77exp−3 | 347 | 9.22exp7 | 1.08exp−8 |

TABLE 1-continued

| | ka (1/Ms) | kd (1/s) | Conc of analyte (nM) | KA (1/M) | KD (M) |
|---|---|---|---|---|---|
| SCA B32ON-45 | 7.72exp5 | 4.64exp−3 | 116 | 1.66exp8 | 6.01exp−9 |
| SCA B32ON-45 | 9.75exp5 | 4.44exp−3 | 38.5 | 2.2exp8 | 4.55exp−9 |
| SCA B32ON-45 | 1.25exp6 | 3.84exp−3 | 12.8 | 3.25exp8 | 3.07exp−9 |

The present invention is, in addition to the disclosure presented above, defined by the following preferred embodiments:

1. A first antibody fragment obtainable by the method of any of claims 1 to 3 and 6 to 15.

2. The first antibody fragment of embodiment 1, wherein the first antibody variable region comprised in the first antibody fragment is present in modified form as compared to the form in which it is comprised in the source immunoglobulin.

3. The first antibody fragment of embodiment 2, wherein the first antibody variable region has been modified so as to render it less likely to elicit a host immune response when administered to a subject as a therapeutic agent.

4. The first antibody fragment of embodiment 3, wherein the first antibody variable region has been humanized and/or deimmunized.

5. The first antibody fragment of embodiment 4, wherein the first antibody variable region has an amino acid sequence as set out in SEQ ID NO: 1.

6. A first or second antibody variable region or fragment thereof derived from the first antibody fragment of embodiment 1.

7. The second antibody variable region or fragment thereof of embodiment 6, wherein the second antibody variable region or fragment thereof is a VL.

8. The VL of embodiment 7, wherein the VL has an amino acid sequence corresponding to a VL sequence in any of FIGS. 11-35.

9. A polypeptide comprising the VL of embodiment 8.

10. A nucleic acid molecule encoding a VL of embodiment 8 or a polypeptide of embodiment 9 or of an antibody fragment of embodiments 1 and 11, or a nucleic acid molecule hybridizing therewith under stringent conditions as described in the description above.

11. A second antibody fragment obtainable by the method of any of claims 4-15.

12. A second or third antibody variable region or fragment thereof derived from the second antibody fragment of embodiment 11.

13. The third antibody variable region or fragment thereof of embodiment 12, wherein the third antibody variable region or fragment thereof is a VH.

14. An antibody fragment which specifically binds at least a portion of the area of the antigen of interest specifically bound by the first antibody fragment of embodiment 16 or the second antibody fragment of embodiment 11.

15. The antibody fragment of embodiment 14, wherein the antibody fragment is a single chain antibody fragment.

16. The antibody fragment of embodiment 14 or 15, wherein the antibody fragment exhibits an amino acid sequence bearing a degree of homology of at least 65% as compared to that of human germline.

Definition of homology: the degree of homology may be determined by standard sequence alignment programs such as Vector NTI (InforMax™, Maryland, USA). Such programs compare aligned sequences on an amino acid-by-amino acid basis, and can be set to various levels of stringency for the comparison (e.g. identical amino acid, conservative amino acid substitution, etc.). Within the meaning of this embodiment, two amino acids in question are considered as being "homologous" when they are either identical to one another or conservative substitutions of one another. By way of non-limiting example, two different amino acids belonging to the class of lipophilic amino acids would be considered homologous in the sense of this embodiment, even if these two amino acids were not identical, whereas a lipophilic amino acid on the one hand and a charged acidic amino acid on the other hand would not be considered homologous.

17. A composition comprising
   a first and/or second antibody fragment according to any of embodiments 1-5 or 11;
   an antibody fragment of any of embodiments 14-16;
   a first, second and or third antibody variable region according to any of embodiments 6-8 or 13;
   A VL of embodiment 8;
   A polypeptide of embodiment 9, and/or
   a carrier or an excipient.

18. The composition of embodiment 17 for use in human and veterinary medicine.

19. Use of the composition of embodiment 18 in the manufacture of a medicament for the treatment of an autoimmune disease or an inflammatory condition.

20. Use of embodiment 19, wherein the autoimmune disease is chosen from rheumatoid arthritis, chronic obstructive pulmonary disease (COPD), asthma, multiple sclerosis (MS) or psoriasis.

21. Use of embodiment 19, wherein the inflammatory condition is a chronic inflammatory condition and/or airway inflammation.

---

The invention claimed is:

1. A method of preparing an antibody fragment of a source immunoglobulin, which source immunoglobulin specifically binds to an antigen of interest, a corresponding antibody fragment of which source immunoglobulin exhibits insufficient soluble recombinant expression, comprising:
(a) providing a nucleic acid molecule encoding a first antibody variable region comprised in the source immunoglobulin, wherein the first antibody variable region is a heavy chain variable region (VH) or a light chain variable region (VL);
(b) respectively combining (i) the nucleic acid molecule encoding the first antibody VH or VL region with (ii) a plurality of nucleic acid molecules encoding a diverse population of a second antibody variable region, wherein the second antibody variable region is a light chain variable region (VL) or a heavy chain variable region (VH), whereby a first population of combined nucleic acid molecules is obtained;
(c) introducing the first population of combined nucleic acid molecules into a display system chosen from a phage display system, a prokaryotic display system, a eukaryotic display system, or an mRNA display system, whereby the nucleic acid molecule encoding the first antibody variable region or the nucleic acid molecule encoding the second antibody variable region is operably linked to a nucleic acid molecule encoding an N-terminal, cis-acting amphipathic polypeptide moiety such that said N-terminal, cis-acting amphipathic polypeptide moiety, when translated, is linked to the N-terminal end of the first or second antibody variable region;
(d) selecting at least one first antibody fragment displayed in step (c) and comprising the VH and VL region, which specifically binds to the antigen of interest and is in soluble form; and
(e) isolating the at least one first antibody fragment selected in step (d);
wherein the amphipathic polypeptide moiety is chosen from the pro regions of any of the following polypeptides: papain, cruzain, thermolysin, cathepsin B, cathepsin L, protease A, protease B, IgA protease and carboxypeptidase Y, or the N2 domain of a filamentous phage.

2. The method of claim 1, wherein the nucleic acid molecule encoding the first antibody variable region is obtained:
(i) by PCR amplification of at least one polynucleotide comprised in a hybridoma cell or B cell which produces the source immunoglobulin; or
(ii) by peptide sequencing of at least one portion of the source immunoglobulin to determine the primary amino acid sequence of the at least one portion of the source immunoglobulin, followed by synthesis of a corresponding nucleic acid molecule capable of encoding the at least one portion of the source immunoglobulin sequenced.

3. The method of claim 1, further comprising:
(i) evaluating the ability of the isolated first antibody fragment to be recombinantly expressed in soluble form; and
(ii) isolating at least one first antibody fragment, the soluble recombinant expression properties of which have been improved relative to those of said corresponding antibody fragment of the source immunoglobulin.

4. The method of claim 1, further comprising:
(a) respectively combining (i) the nucleic acid molecule encoding the second antibody variable region with (ii) a plurality of nucleic acid molecules encoding a diverse population of a third antibody variable region, wherein the third antibody variable region is a heavy chain variable region (VH) or a light chain variable region (VL), whereby a second population of combined nucleic acid molecules is obtained;
(b) introducing the second population of combined nucleic acid molecules into a display system chosen from a phage display system, a prokaryotic display system, a eukaryotic display system, or an mRNA display system;
(c) selecting at least one second antibody fragment displayed in step (b) and comprising the VH and VL region, which specifically binds to the antigen of interest; and
(d) isolating the at least one second antibody fragment selected in step (c);
wherein the nucleic acid molecule encoding the second antibody variable region or the nucleic acid molecule encoding the third antibody variable region is operably linked to a nucleic acid molecule encoding an N-terminal, cis-acting amphipathic polypeptide moiety such that said N-terminal, cis-acting amphipathic polypeptide moiety, when translated, is linked to the N-terminal end of the second or third antibody variable region.

5. The method of claim 4, further comprising:
(i) evaluating the ability of the isolated second antibody fragment to be recombinantly expressed in soluble form; and
(ii) isolating at least one second antibody fragment, the soluble recombinant expression properties of which have been improved relative to those of said corresponding antibody fragment of the source immunoglobulin and/or to those of said first antibody fragment.

6. The method of claim 1, wherein
(i) the nucleic acid molecules encoding the first and the second antibody variable regions making up the first population of combined nucleic acid molecules; and/or
(ii) the nucleic acid molecules encoding the second and the third antibody variable regions making up the second population of combined nucleic acid molecules are introduced into said display system as a single continuous nucleic acid molecule or as two discrete nucleic acid molecules.

7. The method of claim 1, wherein the phage display system is a Cys-display system.

8. The method of claim 1, wherein the mRNA display system is a ribosome display system or a covalent display system.

9. The method of claim 8 wherein the mRNA display system is a puromycin display system.

10. The method of claim 1, wherein the prokaryotic display system is an *Escherichia coli* display system.

11. The method of claim 1, wherein the eukaryotic display system is a yeast display system.

12. The method of claim 1, wherein the nucleic acid molecules encoding the first, second and/or third antibody variable regions is/are from the same or different species.

13. The method of claim 1, wherein:
(i) the source immunoglobulin and the nucleic acid molecule encoding the first antibody variable region are of non-human origin, and
(ii) the nucleic acid molecule encoding the second and third antibody variable region are of human origin.

14. The method of claim 1, wherein:
(i) the first antibody variable region is a VH region, the second antibody variable region is a VL region, and the third antibody variable region is a VH region; or
(ii) the first antibody variable region is a VL region, the second antibody variable region is a VH region, and the third antibody variable region is a VL region.

15. The method of claim 1, wherein the first and/or second antibody fragment/fragments is/are independently chosen from scFv, Fab, (Fab')$_2$, wherein, in the event that a Fab or (Fab)2 antibody fragment is/are chosen, mRNA display is not used.

* * * * *

SEQUENCE LISTING

<160> NUMBER OF SEQ ID NOS: 88

<210> SEQ ID NO 1
<211> LENGTH: 120
<212> TYPE: PRT
<213> ORGANISM: artificial sequence
<220> FEATURE:
<223> OTHER INFORMATION: VH of anti-GM-CSF immunoglobulin

<400> SEQUENCE: 1

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser
        115                 120

<210> SEQ ID NO 2
<211> LENGTH: 726
<212> TYPE: DNA
<213> ORGANISM: artificial sequence
<220> FEATURE:
<223> OTHER INFORMATION: B32oN-10 (nuc)

<400> SEQUENCE: 2
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300

```
ggtctgatag cagtctactt tgattactgg ggccaaggga ccacggtcac cgtctcctca    360
ggtggtggtg gttctggcgg cggcggctcc ggtggtggtg gttctgagct ccagatgacc    420
cagtctccat cctccctgtc tgcatctgta ggagacagag tcaccatcac ttgccggaca    480
agtcagacca ttagcagtct tttaaattgg tatcagcaga aaccagggaa agcccctaag    540
ctcctgatct atgctgcatc caatttgcaa agtggggtcc catcaaggtt cagtggcagt    600
ggatctggga cagatttcac tctcaccatc agcggtctgc aacctgaaga ttttcaact     660 tacttctgtc aacagagtta cagtttccct cgaacgttcg gccaagggac caaagtggat    720
atcaaa                                                                726
```

<210> SEQ ID NO 3
<211> LENGTH: 242
<212> TYPE: PRT
<213> ORGANISM: artificial sequence
<220> FEATURE:
<223> OTHER INFORMATION: B32oN-10 (prot)

<400> SEQUENCE: 3

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Gln Met Thr Gln Ser Pro Ser
    130                 135                 140

Ser Leu Ser Ala Ser Val Gly Asp Arg Val Thr Ile Thr Cys Arg Thr
145                 150                 155                 160

Ser Gln Thr Ile Ser Ser Leu Leu Asn Trp Tyr Gln Gln Lys Pro Gly
                165                 170                 175

Lys Ala Pro Lys Leu Leu Ile Tyr Ala Ala Ser Asn Leu Gln Ser Gly
            180                 185                 190

Val Pro Ser Arg Phe Ser Gly Ser Gly Ser Gly Thr Asp Phe Thr Leu
        195                 200                 205

Thr Ile Ser Gly Leu Gln Pro Glu Asp Phe Ser Thr Tyr Phe Cys Gln
    210                 215                 220

Gln Ser Tyr Ser Phe Pro Arg Thr Phe Gly Gln Gly Thr Lys Val Asp
225                 230                 235                 240

Ile Lys
```

<210> SEQ ID NO 4
<211> LENGTH: 726
<212> TYPE: DNA
<213> ORGANISM: artificial sequence
<220> FEATURE:
<223> OTHER INFORMATION: B32oN-33 (nuc)

<400> SEQUENCE: 4

```
gagctgcagc tggtcgagca gtctggagct gcactggtga agcctgggga ctctgtgaag    60
atgtcttgca aagcttctgg ttatccattc actgactata ttgtacactg ggtgaagcag   120
agtcatggaa agagccttga ctggattggt tatattaatc cttacagtgg tgatactaag   180
ttcaatgaaa agttcaagag taaggccacg ttgactgttg acaagtccag cagcacagcc   240
tatatggagt ttagccgatt gacatctgag gattctgcaa tctattactg tgcaagatcg   300
ggtctgatag cagtctactt tgattactgg ggccaaggga ccacggtcac cgtctcctca   360
gtggtggtg gttctggcgg cggcggctcc ggtggtggtg gttctgagct cgtgatgacg   420
cagtctccag ccaccctgtc tttgtctcca ggggaaagag ccaccctctc ctgcagggcc   480
agtcagagtg ttaggaccta cttagcctgg taccaacaga aacctggcca ggctcccagg   540
ctcctcatct atgctgcatc ccacagggcc actggcatcc cagccaggtt cagtggcagt   600
gggtctggga cagacttcac tctcaccatc agcagactgg agcctgaaga ttttgcagtg   660
tattactgtc agcagtatgg tagctcacct ccgacgttcg gccaagggac caaggtagag   720
atcaaa                                                              726
```

<210> SEQ ID NO 5
<211> LENGTH: 242
<212> TYPE: PRT
<213> ORGANISM: artificial sequence
<220> FEATURE:
<223> OTHER INFORMATION: B32oN-33 (prot)

<400> SEQUENCE: 5

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Ser Val Arg Thr Tyr Leu Ala Trp Tyr Gln Gln Lys Pro Gly
                165                 170                 175

Gln Ala Pro Arg Leu Leu Ile Tyr Ala Ala Ser His Arg Ala Thr Gly
            180                 185                 190

Ile Pro Ala Arg Phe Ser Gly Ser Gly Ser Gly Thr Asp Phe Thr Leu
        195                 200                 205

Thr Ile Ser Arg Leu Glu Pro Glu Asp Phe Ala Val Tyr Tyr Cys Gln
    210                 215                 220
```

Gln Tyr Gly Ser Ser Pro Pro Thr Phe Gly Gln Gly Thr Lys Val Glu
225                 230                 235                 240

Ile Lys

<210> SEQ ID NO 6
<211> LENGTH: 726
<212> TYPE: DNA
<213> ORGANISM: artificial sequence
<220> FEATURE:
<223> OTHER INFORMATION: B32oN-44  (nuc)

<400> SEQUENCE: 6

```
gagctgcagc tggtcgagca gtctggagct gcactggtga agcctgggga ctctgtgaag    60
atgtcttgca agcttctgg ttatccattc actgactata ttgtacactg ggtgaagcag   120
agtcatggaa agagccttga ctggattggt tatattaatc cttacagtgg tgatactaag   180
ttcaatgaaa agttcaagag taaggccacg ttgactgttg acaagtccag cagcacagcc   240
tatatggagt ttagccgatt gacatctgag gattctgcaa tctattactg tgcaagatcg   300
ggtctgatag cagtctactt tgattactgg ggccaaggga ccacggtcac cgtctcctca   360
ggtggtggtg gttctggcgg cggcggctcc ggtggtggtg gttctgagct cgtgctgact   420
cagtctccgg actttcagtc tgtgactcca aggagaaag tcaccatcac ctgccgggcc   480
agtcagagca ttggtagtag cttacactgg taccagcaga accagatca gcctccaaag   540
ctcctcatca aatttgcttc ccagtccatc tcaagggtcc cctcgaggtt cagtggcact   600
ggatctggga cagatttcac cctcaccatc aatagcctgg aagctgaaga tgctgcaacg   660
tattactgtc agcagagctt tagtttcccg tacacttttg gccaggggac caagctggag   720
atcaaa                                                             726
```

<210> SEQ ID NO 7
<211> LENGTH: 242
<212> TYPE: PRT
<213> ORGANISM: artificial sequence
<220> FEATURE:
<223> OTHER INFORMATION: B32oN-44 (prot)

<400> SEQUENCE: 7

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
                20                  25                  30

Tyr Ile Val His Trp Val Lys Gln Ser His Gly Lys Ser Leu Asp Trp
            35                  40                  45

Ile Gly Tyr Ile Asn Pro Tyr Ser Gly Asp Thr Lys Phe Asn Glu Lys
        50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala

```
                145                 150                 155                 160
Ser Gln Ser Ile Gly Ser Ser Leu His Trp Tyr Gln Gln Lys Pro Asp
                        165                 170                 175

Gln Pro Pro Lys Leu Leu Ile Lys Phe Ala Ser Gln Ser Ile Ser Arg
                180                 185                 190

Val Pro Ser Arg Phe Ser Gly Thr Gly Ser Gly Thr Asp Phe Thr Leu
                195                 200                 205

Thr Ile Asn Ser Leu Glu Ala Glu Asp Ala Ala Thr Tyr Tyr Cys Gln
            210                 215                 220

Gln Ser Phe Ser Phe Pro Tyr Thr Phe Gly Gln Gly Thr Lys Leu Glu
225                 230                 235                 240

Ile Lys

<210> SEQ ID NO 8
<211> LENGTH: 726
<212> TYPE: DNA
<213> ORGANISM: artificial sequence
<220> FEATURE:
<223> OTHER INFORMATION: B32oN-45 (nuc)

<400> SEQUENCE: 8
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg gttctggcgg cggcggctcc ggtggtggtg gttctgagct cgtgatgacc     420
cagtctccat cttccgtgtc tgcatctgta ggagacagag tcaccatcgc ttgtcgggcg     480
agtcagaaca ttagaaacat tttaaattgg tatcaacaga gaccagggaa ggcccctcaa     540
ctcctgatct atgctgcctc caatttacaa agtggcgtcc catcaaggtt cagtggcagt     600
ggatctggga cagatttcac tctcaccatc aacagtctgc aacctgaaga ttttgcaact     660
tactactgtc aacagagtta cagtatgcct cgaactttcg gcggagggac caaggtggaa     720
atcaaa                                                                726

<210> SEQ ID NO 9
<211> LENGTH: 242
<212> TYPE: PRT
<213> ORGANISM: artificial sequence
<220> FEATURE:
<223> OTHER INFORMATION: B32oN-45 (prot)

<400> SEQUENCE: 9

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
                20                  25                  30

Tyr Ile Val His Trp Val Lys Gln Ser His Gly Lys Ser Leu Asp Trp
            35                  40                  45

Ile Gly Tyr Ile Asn Pro Tyr Ser Gly Asp Thr Lys Phe Asn Glu Lys
        50                  55                  60

Phe Lys Ser Lys Ala Thr Leu Thr Val Asp Lys Ser Ser Ser Thr Ala
65                  70                  75                  80
```

```
Tyr Met Glu Phe Ser Arg Leu Thr Ser Glu Asp Ser Ala Ile Tyr Tyr
            85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
            115                 120                 125

Gly Ser Gly Gly Gly Ser Glu Leu Val Met Thr Gln Ser Pro Ser
            130                 135                 140

Ser Val Ser Ala Ser Val Gly Asp Arg Val Thr Ile Ala Cys Arg Ala
145                 150                 155                 160

Ser Gln Asn Ile Arg Asn Ile Leu Asn Trp Tyr Gln Arg Pro Gly
            165                 170                 175

Lys Ala Pro Gln Leu Leu Ile Tyr Ala Ala Ser Asn Leu Gln Ser Gly
            180                 185                 190

Val Pro Ser Arg Phe Ser Gly Ser Gly Ser Gly Thr Asp Phe Thr Leu
            195                 200                 205

Thr Ile Asn Ser Leu Gln Pro Glu Asp Phe Ala Thr Tyr Tyr Cys Gln
            210                 215                 220

Gln Ser Tyr Ser Met Pro Arg Thr Phe Gly Gly Gly Thr Lys Val Glu
225                 230                 235                 240

Ile Lys
```

<210> SEQ ID NO 10
<211> LENGTH: 726
<212> TYPE: DNA
<213> ORGANISM: artificial sequence
<220> FEATURE:
<223> OTHER INFORMATION: B32oN-48 (nuc)

<400> SEQUENCE: 10

```
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg gttctggcgg cggcggctcc ggtggtggtg gttctgagct cgtgctgact     420
cagtctccag gctttcagtc tgtgactcca aaggagaaag tcaccatcac ctgccgggcc     480
agtcagagca ttggtagtag cttacactgg taccagcaga accagatca gcctccaaag     540
ctcctcatca aatttgcttc ccagtccatc tcagggtcc cctcgaggtt cagtggcagt     600
ggatctggga caatttcac cctcaccatc aatagcctgg aagctgaaga tgctgcaacc     660
tattactgtc agcagagtag tactttacct cccacttttg gccagggac caaggtggag     720
atcaaa                                                                726
```

<210> SEQ ID NO 11
<211> LENGTH: 242
<212> TYPE: PRT
<213> ORGANISM: artificial sequence
<220> FEATURE:
<223> OTHER INFORMATION: B32oN-48 (prot)

<400> SEQUENCE: 11

```
Glu Leu Gln Leu Val Glu Gln Ser Gly Ala Ala Leu Val Lys Pro Gly
1               5                   10                  15
```

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
 50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Gly
130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Pro Pro Lys Leu Leu Ile Lys Phe Ala Ser Gln Ser Ile Ser Gly
            180                 185                 190

Val Pro Ser Arg Phe Ser Gly Ser Gly Ser Gly Thr Asn Phe Thr Leu
        195                 200                 205

Thr Ile Asn Ser Leu Glu Ala Glu Asp Ala Ala Thr Tyr Tyr Cys Gln
 210                 215                 220

Gln Ser Ser Thr Leu Pro Pro Thr Phe Gly Gln Gly Thr Lys Val Glu
225                 230                 235                 240

Ile Lys

<210> SEQ ID NO 12
<211> LENGTH: 726
<212> TYPE: DNA
<213> ORGANISM: artificial sequence
<220> FEATURE:
<223> OTHER INFORMATION: B32oN-49 (nuc)

<400> SEQUENCE: 12

```
gagctgcagc tggtcgagca gtctggagct gcactggtga agcctgggga ctctgtgaag     60
atgtcttgca aagcttctgg ttatccattc actgactata ttgtacactg ggtgaagcag    120
agtcatggaa agagccttga ctggattggt tatattaatc cttacagtgg tgatactaag    180
ttcaatgaaa agttcaagag taaggccacg ttgactgttg acaagtccag cagcacagcc    240
tatatggagt ttagccgatt gacatctgag gattctgcaa tctattactg tgcaagatcg    300
ggtctgatag cagtctactt tgattactgg ggccaaggga ccacggtcac cgtctcctca    360
ggtggtggtg gttctggcgg cggcggctcc ggtggtggtg gttctgagct cgtgctgact    420
cagtctccag actttcagtc tgtgactcca aaggagaaag tcaccatcac ctgccgggcc    480
agtcagagca ttggtagtag cttacactgg taccagcaga aaccagatca gtctccaaag    540
ctcctcatca gttttgcttc ccagtccctc tcagggtcc cctcgaggtt cagtggcagt    600
ggatctggga cagatttcac tctcaccatc agcagtctac aacctgaaga ttttgcaact    660
tactactgtc aacagagtta cactacccc cccactttcg gcggagggac caaggtggaa    720
atcaaa                                                               726
```

<210> SEQ ID NO 13
<211> LENGTH: 242
<212> TYPE: PRT
<213> ORGANISM: artificial sequence
<220> FEATURE:
<223> OTHER INFORMATION: B32oN-49 (prot)

<400> SEQUENCE: 13

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Thr Thr Pro Pro Thr Phe Gly Gly Gly Thr Lys Val Glu
225                 230                 235                 240

Ile Lys

<210> SEQ ID NO 14
<211> LENGTH: 726
<212> TYPE: DNA
<213> ORGANISM: artificial sequence
<220> FEATURE:
<223> OTHER INFORMATION: B32oN-67 (nuc)

<400> SEQUENCE: 14
gagctgcagc tggtcgagca gtctggagct gcactggtga agcctgggga ctctgtgaag        60
atgtcttgca aagcttctgg ttatccattc actgactata ttgtacactg ggtgaagcag       120
agtcatggaa agagccttga ctggattggt tatattaatc cttacagtgg tgatactaag       180
ttcaatgaaa agttcaagag taaggccacg ttgactgttg acaagtccag cagcacagcc       240
tatatggagt ttagccgatt gacatctgag gattctgcaa tctattactg tgcaagatcg       300
ggtctgatag cagtctactt tgattactgg ggccaaggga ccacggtcac cgtctcctca       360

```
ggtggtggtg gttctggcgg cggcggctcc ggtggtggtg gttctgagct cgtgctgact      420
cagtctcccg gctttcagtc tgtgactcca aaggagaaag tcaccatcac ctgccgggcc      480
agtcagagca ttggtagtag cttacactgg taccagcaga aaccagatca gtctccaaag      540
ctcctcatca aatttgcttc ccagtccatc tcagggtcc cctcgaggtt cactggcagt       600
ggatctggga cagatttcac tctcaccatc agcagtctgc aacctgaaga tattgcaact      660
tactactgtc aacagagtta cagtacccct tggacgttcg gccaagggac caagctggag      720
atcaaa                                                                 726
```

```
<210> SEQ ID NO 15
<211> LENGTH: 242
<212> TYPE: PRT
<213> ORGANISM: artificial sequence
<220> FEATURE:
<223> OTHER INFORMATION: B32oN-67 (prot)

<400> SEQUENCE: 15
```

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Gly
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Ile Ser Gly
            180                 185                 190

Val Pro Ser Arg Phe Thr Gly Ser Gly Ser Gly Thr Asp Phe Thr Leu
        195                 200                 205

Thr Ile Ser Ser Leu Gln Pro Glu Asp Ile Ala Thr Tyr Tyr Cys Gln
    210                 215                 220

Gln Ser Tyr Ser Thr Pro Trp Thr Phe Gly Gln Gly Thr Lys Leu Glu
225                 230                 235                 240

Ile Lys

```
<210> SEQ ID NO 16
<211> LENGTH: 726
<212> TYPE: DNA
<213> ORGANISM: artificial sequence
<220> FEATURE:
<223> OTHER INFORMATION: B32oN-73 (nuc)

<400> SEQUENCE: 16
```

```
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg gttctggcgg cggcggctcc ggtggtggtg gttctgagct cgtgctgact     420
cagtctcccg gctttcagtc tgtgactcca aaggagaaag tcaccatcac ctgccgggcc     480
agtcagagca ttggtagtag cttacactgg taccagcaga aaccagatca gtctccaaag     540
ctcctcatca aatttgcttc ccagtccatc tcagggtcc cctcgaggtt cagtggcact      600
ggatctggga cagatttcac tctcaccatc agcagtctgc aacctgaaga tattgcaact     660
tactactgtc aacagagtta cagtacccct tggacgttcg gccaagggac caagctggag     720
atcaaa                                                                 726
```

```
<210> SEQ ID NO 17
<211> LENGTH: 242
<212> TYPE: PRT
<213> ORGANISM: artificial sequence
<220> FEATURE:
<223> OTHER INFORMATION: B32oN-73 (prot)

<400> SEQUENCE: 17
```

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Gly
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Ile Ser Gly
            180                 185                 190

Val Pro Ser Arg Phe Ser Gly Thr Gly Ser Gly Thr Asp Phe Thr Leu
        195                 200                 205

Thr Ile Ser Ser Leu Gln Pro Glu Asp Ile Ala Thr Tyr Tyr Cys Gln
    210                 215                 220

Gln Ser Tyr Ser Thr Pro Trp Thr Phe Gly Gln Gly Thr Lys Leu Glu

```
                    225                 230                 235                 240

Ile Lys

<210> SEQ ID NO 18
<211> LENGTH: 726
<212> TYPE: DNA
<213> ORGANISM: artificial sequence
<220> FEATURE:
<223> OTHER INFORMATION: B33oN-8 (nuc)

<400> SEQUENCE: 18
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg gttctggcgg cggcggctcc ggtggtggtg gttctgagct cgtgctgact     420
cagtctccag gctttcagtc tgtgactcca aaggagaaag tcaccatcac ctgccgggcc     480
agtcagagca ttggtagtag cttaaactgg taccagcaga aaccagatca gcctccaaag     540
ctcctcatca aattcgcttc gcagtccatc tcagggtctc ttcgaggttc agtggcact      600 ggatctggga cagatttcac cctcactatc agcagcctgc agcctgaaga tgttgcaact     660
tattactgtc aacagagtta cagtacccct ccgacgttcg gccaagggac caagctggag     720
atcaaa                                                                726

<210> SEQ ID NO 19
<211> LENGTH: 242
<212> TYPE: PRT
<213> ORGANISM: artificial sequence
<220> FEATURE:
<223> OTHER INFORMATION: B33oN-8 (prot)

<400> SEQUENCE: 19

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Ser Glu Leu Val Leu Thr Gln Ser Pro Gly
    130                 135                 140

Phe Gln Ser Val Thr Pro Lys Glu Lys Val Thr Ile Thr Cys Arg Ala
145                 150                 155                 160
```

```
Ser Gln Ser Ile Gly Ser Ser Leu Asn Trp Tyr Gln Lys Pro Asp
            165                 170                 175

Gln Pro Pro Lys Leu Leu Ile Lys Phe Ala Ser Gln Ser Ile Ser Gly
            180                 185                 190

Val Ser Ser Arg Phe Ser Gly Thr Gly Ser Gly Thr Asp Phe Thr Leu
        195                 200                 205

Thr Ile Ser Ser Leu Gln Pro Glu Asp Val Ala Thr Tyr Tyr Cys Gln
        210                 215                 220

Gln Ser Tyr Ser Thr Pro Pro Thr Phe Gly Gln Gly Thr Lys Leu Glu
225                 230                 235                 240

Ile Lys
```

<210> SEQ ID NO 20
<211> LENGTH: 726
<212> TYPE: DNA
<213> ORGANISM: artificial sequence
<220> FEATURE:
<223> OTHER INFORMATION: B33oN-21 (nuc)

<400> SEQUENCE: 20

```
gagctgcagc tggtcgagca gtctggagct gcactggtga agcctgggga ctctgtgaag    60
atgtcttgca aagcttctgg ttatccattc actgactata ttgtacactg ggtgaagcag   120
agtcatggaa agagccttga ctggattggt tatattaatc cttacagtgg tgatactaag   180
ttcaatgaaa agttcaagag taaggccacg ttgactgttg acaagtccag cagcacagcc   240
tatatggagt ttagccgatt gacatctgag gattctgcaa tctattactg tgcaagatcg   300
ggtctgatag cagtctactt tgattactgg ggccaaggga ccacggtcac cgtctcctca   360
ggtggtggtg gttctggcgg cggcggctcc ggtggtggtg gttctgagct cgtgctgact   420
cagtctccag actttcagtc tgtgactcca aaggagaaag tcaccatcac ctgccgggcc   480
agtcagagca ttggtagtag cttacactgg taccagcaga aaccagatca gtctccaaag   540
ctcctcatca gtttgcttc ccagtccctc tcaggggtcc cctcgaggtt cagtggcagt   600
ggatccggga cagatttcac cctcaccatc aatagcctgg aagctgaaga tgctgcaacg   660
tattactgtc aacagagtta cagtaccccg tggacgttcg gccaagggac caagctggag   720
atcaaa                                                              726
```

<210> SEQ ID NO 21
<211> LENGTH: 242
<212> TYPE: PRT
<213> ORGANISM: artificial sequence
<220> FEATURE:
<223> OTHER INFORMATION: B33oN-21 (prot)

<400> SEQUENCE: 21

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95
```

Cys Ala Arg Ser Gly Leu Ile Ala Val Tyr Phe Asp Tyr Trp Gly Gln
                100                 105                 110

Gly Thr Thr Val Thr Val Ser Ser Gly Gly Gly Ser Gly Gly Gly
            115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Thr Leu
        195                 200                 205

Thr Ile Asn Ser Leu Glu Ala Glu Asp Ala Ala Thr Tyr Tyr Cys Gln
    210                 215                 220

Gln Ser Tyr Ser Thr Pro Trp Thr Phe Gly Gln Gly Thr Lys Leu Glu
225                 230                 235                 240

Ile Lys

<210> SEQ ID NO 22
<211> LENGTH: 726
<212> TYPE: DNA
<213> ORGANISM: artificial sequence
<220> FEATURE:
<223> OTHER INFORMATION: B33oN-22 (nuc)

<400> SEQUENCE: 22
gagctgcagc tggtcgagca gtctggagct gcactggtga agcctgggga ctctgtgaag    60
atgtcttgca aagcttctgg ttatccattc actgactata ttgtacactg ggtgaagcag   120
agtcatggaa agagccttga ctggattggt tatattaatc cttacagtgg tgatactaag   180
ttcaatgaaa agttcaagag taaggccacg ttgactgttg acaagtccag cagcacagcc   240
tatatggagt ttagccgatt gacatctgag gattctgcaa tctattactg tgcaagatcg   300
ggtctgatag cagtctactt tgattactgg ggccaaggga ccacggtcac cgtctcctca   360
ggtggtggtg gttctggcgg cggcggctcc ggtggtggtg gttctgagct cgtgctgact   420
cagtctccag actttcagtc tgtgactcca aaggagaaag tcaccatcac ctgccgggcc   480
agtcagagca ttggtagtag cttacactgg taccagcaga aaccagatca gtctccaaag   540
ctcctcatca gtttgcttc ccagtccttc tcaggggtcc cctcgaggtt cagtggcagt   600
ggatctggga cagatttcac cctcaccatc aatagcctgg aagctgaaga tgctgcaacg   660
tattactgtc aacagagtta cagtacccct ccgacgttcg gccaagggac caaggtggag   720
atcaaa                                                             726

<210> SEQ ID NO 23
<211> LENGTH: 242
<212> TYPE: PRT
<213> ORGANISM: artificial sequence
<220> FEATURE:
<223> OTHER INFORMATION: B33oN-22 (prot)

<400> SEQUENCE: 23

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp

```
                20                  25                  30
Tyr Ile Val His Trp Val Lys Gln Ser His Gly Lys Ser Leu Asp Trp
            35                  40                  45
Ile Gly Tyr Ile Asn Pro Tyr Ser Gly Asp Thr Lys Phe Asn Glu Lys
            50                  55                  60
Phe Lys Ser Lys Ala Thr Leu Thr Val Asp Lys Ser Ser Ser Thr Ala
65                  70                  75                  80
Tyr Met Glu Phe Ser Arg Leu Thr Ser Glu Asp Ser Ala Ile Tyr Tyr
                85                  90                  95
Cys Ala Arg Ser Gly Leu Ile Ala Val Tyr Phe Asp Tyr Trp Gly Gln
            100                 105                 110
Gly Thr Thr Val Thr Val Ser Ser Gly Gly Gly Gly Ser Gly Gly Gly
            115                 120                 125
Gly Ser Gly Gly Gly Ser Glu Leu Val Leu Thr Gln Ser Pro Asp
            130                 135                 140
Phe Gln Ser Val Thr Pro Lys Glu Lys Val Thr Ile Thr Cys Arg Ala
145                 150                 155                 160
Ser Gln Ser Ile Gly Ser Ser Leu His Trp Tyr Gln Gln Lys Pro Asp
                165                 170                 175
Gln Ser Pro Lys Leu Leu Ile Lys Phe Ala Ser Gln Ser Phe Ser Gly
            180                 185                 190
Val Pro Ser Arg Phe Ser Gly Ser Gly Ser Gly Thr Asp Phe Thr Leu
            195                 200                 205
Thr Ile Asn Ser Leu Glu Ala Glu Asp Ala Ala Thr Tyr Tyr Cys Gln
            210                 215                 220
Gln Ser Tyr Ser Thr Pro Pro Thr Phe Gly Gln Gly Thr Lys Val Glu
225                 230                 235                 240
Ile Lys

<210> SEQ ID NO 24
<211> LENGTH: 726
<212> TYPE: DNA
<213> ORGANISM: artificial sequence
<220> FEATURE:
<223> OTHER INFORMATION: B33oN-35 (nuc)

<400> SEQUENCE: 24
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg gttctggcgg cggcggctcc ggtggtggtg gttctgagct ccagatgacc     420
cagtctccat cctccctgtc tgcatctgta ggagacagag tcaccatcac ctgccgggcc     480
agtcagagca ttggtagtag cttacactgg taccagcaga aaccagatca gtctccaaag     540
ctcctcatca gtttgcttc ccagtccttc tcagggtcc cctcgaggtt cggtggcagt     600
ggatctggga caaatttcac cctcaccatc aatagcctgg aagctgaaga tgctgcaacc     660
tattactgtc agcagagtag tactttacct cccactttg gccaggggac caagctggag     720
atcaaa                                                              726
```

<210> SEQ ID NO 25
<211> LENGTH: 242
<212> TYPE: PRT
<213> ORGANISM: artificial sequence
<220> FEATURE:
<223> OTHER INFORMATION: B33oN-35 (prot)

<400> SEQUENCE: 25

```
Glu Leu Gln Leu Val Glu Gln Ser Gly Ala Ala Leu Val Lys Pro Gly
1               5                   10                  15
Asp Ser Val Lys Met Ser Cys Lys Ala Ser Gly Tyr Pro Phe Thr Asp
            20                  25                  30
Tyr Ile Val His Trp Val Lys Gln Ser His Gly Lys Ser Leu Asp Trp
        35                  40                  45
Ile Gly Tyr Ile Asn Pro Tyr Ser Gly Asp Thr Lys Phe Asn Glu Lys
    50                  55                  60
Phe Lys Ser Lys Ala Thr Leu Thr Val Asp Lys Ser Ser Ser Thr Ala
65                  70                  75                  80
Tyr Met Glu Phe Ser Arg Leu Thr Ser Glu Asp Ser Ala Ile Tyr Tyr
                85                  90                  95
Cys Ala Arg Ser Gly Leu Ile Ala Val Tyr Phe Asp Tyr Trp Gly Gln
            100                 105                 110
Gly Thr Thr Val Thr Val Ser Ser Gly Gly Gly Gly Ser Gly Gly Gly
        115                 120                 125
Gly Ser Gly Gly Gly Ser Glu Leu Gln Met Thr Gln Ser Pro Ser
    130                 135                 140
Ser Leu Ser Ala Ser Val Gly Asp Arg Val Thr Ile Thr Cys Arg Ala
145                 150                 155                 160
Ser Gln Ser Ile Gly Ser Ser Leu His Trp Tyr Gln Gln Lys Pro Asp
                165                 170                 175
Gln Ser Pro Lys Leu Leu Ile Lys Phe Ala Ser Gln Ser Phe Ser Gly
            180                 185                 190
Val Pro Ser Arg Phe Gly Gly Ser Gly Ser Gly Thr Asn Phe Thr Leu
        195                 200                 205
Thr Ile Asn Ser Leu Glu Ala Glu Asp Ala Ala Thr Tyr Tyr Cys Gln
    210                 215                 220
Gln Ser Ser Thr Leu Pro Pro Thr Phe Gly Gln Gly Thr Lys Leu Glu
225                 230                 235                 240
Ile Lys
```

<210> SEQ ID NO 26
<211> LENGTH: 726
<212> TYPE: DNA
<213> ORGANISM: artificial sequence
<220> FEATURE:
<223> OTHER INFORMATION: B33oN-66 (nuc)

<400> SEQUENCE: 26

```
gagctgcagc tggtcgagca gtctggagct gcactggtga agcctgggga ctctgtgaag    60
atgtcttgca agcttctggt tatccattc actgactata ttgtacactg ggtgaagcag   120
agtcatggaa agagccttga ctggattggt tatattaatc cttacagtgg tgatactaag   180
ttcaatgaaa agttcaagag taaggccacg ttgactgttg acaagtccag cagcacagcc   240
tatatggagt ttagccgatt gacatctgag gattctgcaa tctattactg tgcaagatcg   300
ggtctgatag cagtctactt tgattactgg ggccaaggga ccacggtcac cgtctcctca   360
ggtggtggtg gttctggcgg cggcggctcc ggtggtggtg gttctgagct cgtgctgact   420
```

```
cagtctccag actttcagtc tgtgactcca aggagaaag tcaccatcac ctgccgggcc      480
agtcagagca ttggtagtaa cttacactgg taccagcaga aaccagatca gtctccaaag    540
ctcctcatca agtttgcttc ccagtccttc tcaggggtcc cctcgaggtt cagtggcagt    600
ggatctggga cagatttcag cctcaccatc aatagcctgg aagctgaaga tgctgcaact    660
tactactgtc aacagagtta cagtacccct cccaccttcg gccaagggac acgactggag    720
attaaa                                                                726
```

<210> SEQ ID NO 27
<211> LENGTH: 242
<212> TYPE: PRT
<213> ORGANISM: artificial sequence
<220> FEATURE:
<223> OTHER INFORMATION: B33oN-66 (prot)

<400> SEQUENCE: 27

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Asn Leu His Trp Tyr Gln Gln Lys Pro Asp
                165                 170                 175

Gln Ser Pro Lys Leu Leu Ile Lys Phe Ala Ser Gln Ser Phe Ser Gly
            180                 185                 190

Val Pro Ser Arg Phe Ser Gly Ser Gly Ser Gly Thr Asp Phe Ser Leu
        195                 200                 205

Thr Ile Asn Ser Leu Glu Ala Glu Asp Ala Ala Thr Tyr Tyr Cys Gln
    210                 215                 220

Gln Ser Tyr Ser Thr Pro Pro Thr Phe Gly Gln Gly Thr Arg Leu Glu
225                 230                 235                 240

Ile Lys
```

<210> SEQ ID NO 28
<211> LENGTH: 726
<212> TYPE: DNA
<213> ORGANISM: artificial sequence
<220> FEATURE:
<223> OTHER INFORMATION: B33oN-67 (nuc)

<400> SEQUENCE: 28

```
gagctgcagc tggtcgagca gtctggagct gcactggtga agcctgggga ctctgtgaag    60
```

```
atgtcttgca aagcttctgg ttatccattc actgactata ttgtacactg ggtgaagcag    120
agtcatggaa agagccttga ctggattggt tatattaatc cttacagtgg tgatactaag    180
ttcaatgaaa agttcaagag taaggccacg ttgactgttg acaagtccag cagcacagcc    240
tatatggagt ttagccgatt gacatctgag gattctgcaa tctattactg tgcaagatcg    300
ggtctgatag cagtctactt tgattactgg ggccaaggga ccacggtcac cgtctcctca    360
ggtggtggtg gttctggcgg cggcggctcc ggtggtggtg gttctgagct cgtgctgact    420
cagtctccag actttcagtc tgtgactcca aaggagaaag tcaccatcac ctgccgggcc    480
agtcagagca ttggtagtag cttacactgg taccagcaga accagatca gtctccaaag    540 ctcctcatca aatttgcttc ccagtccatc tcagggtcc catcgaggtt cagtggcagt    600
ggatctggga cagatttcac tctcaccatc agcagtctgc aacctgaaga ttttgcaact    660
tactactgtc aacagagtta cagtacccct cccactttcg gccctgggac caagctggag    720
atcaaa                                                                726
```

<210> SEQ ID NO 29
<211> LENGTH: 242
<212> TYPE: PRT
<213> ORGANISM: artificial sequence
<220> FEATURE:
<223> OTHER INFORMATION: B33oN-67 (prot)

<400> SEQUENCE: 29

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Ile Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Ser Thr Pro Pro Thr Phe Gly Pro Gly Thr Lys Leu Glu
225                 230                 235                 240
```

Ile Lys

<210> SEQ ID NO 30
<211> LENGTH: 726
<212> TYPE: DNA
<213> ORGANISM: artificial sequence
<220> FEATURE:
<223> OTHER INFORMATION: B33oN-69 (nuc)

<400> SEQUENCE: 30

```
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg gttctggcgg cggcggctcc ggtggtggtg gttctgagct cgtgctgact     420
cagtctccag actttcaatc tgtgactcca aaggagaaag tcaccatcac ctgccgggcc     480
agtcagagca ttggtactgg cttacactgg taccagcaga aaccggatca gtctccaaag     540
ctcctcatca aatttgcttc ccagtccttc tcagggtccc ctcgaggtt cagtggcagt      600
ggatctggga cagatttcac cctcaccatc aatggcctgg aagctgaaga tgctgcaacg     660
tattactgtc agcagagtag tactttacct cccacttttg gccaggggac caagctggag     720
atcaaa                                                                726
```

<210> SEQ ID NO 31
<211> LENGTH: 242
<212> TYPE: PRT
<213> ORGANISM: artificial sequence
<220> FEATURE:
<223> OTHER INFORMATION: B33oN-69 (prot)

<400> SEQUENCE: 31

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
                20                  25                  30

Tyr Ile Val His Trp Val Lys Gln Ser His Gly Lys Ser Leu Asp Trp
            35                  40                  45

Ile Gly Tyr Ile Asn Pro Tyr Ser Gly Asp Thr Lys Phe Asn Glu Lys
        50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Thr Gly Leu His Trp Tyr Gln Gln Lys Pro Asp
                165                 170                 175
```

Gln Ser Pro Lys Leu Leu Ile Lys Phe Ala Ser Gln Ser Phe Ser Gly
            180                 185                 190

Val Pro Ser Arg Phe Ser Gly Ser Gly Ser Gly Thr Asp Phe Thr Leu
            195                 200                 205

Thr Ile Asn Gly Leu Glu Ala Glu Asp Ala Ala Thr Tyr Tyr Cys Gln
            210                 215                 220

Gln Ser Ser Thr Leu Pro Pro Thr Phe Gly Gln Gly Thr Lys Leu Glu
225                 230                 235                 240

Ile Lys

<210> SEQ ID NO 32
<211> LENGTH: 726
<212> TYPE: DNA
<213> ORGANISM: artificial sequence
<220> FEATURE:
<223> OTHER INFORMATION: B33oN-115 (nuc)

<400> SEQUENCE: 32
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg gttctggcgg cggcggctcc ggtggtggtg gttctgagct cgtgctgact     420
cagtctccag actttcagtc tgtgactcca aaggagaaag tcaccatcac ctgccgggcc     480
agtcagagca ttggtagtag cttacactgg taccagcaga accagatcag tctccaaag     540
ctcctcatca gttttgcttc ccagtccctc tcagggtgtcc cctcgaggtt cagtggcagt     600
ggatctggga cagatttcac tctcaccatc agcagtctgc aacctgaaga ttttgcaact     660
tactactgtc aacagagtta cagtacccct agtactttcg gccctgggac caaggtggag     720
atcaaa                                                                  726

<210> SEQ ID NO 33
<211> LENGTH: 242
<212> TYPE: PRT
<213> ORGANISM: artificial sequence
<220> FEATURE:
<223> OTHER INFORMATION: B33oN-115 (prot)

<400> SEQUENCE: 33

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln

Gly Thr Thr Val Thr Val Ser Ser Gly Gly Gly Ser Gly Gly Gly
                115                 120                 125

Gly Ser Gly Gly Gly Ser Glu Leu Val Leu Thr Gln Ser Pro Asp
        130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Lys Pro Asp
                165                 170                 175

Gln Ser Pro Lys Leu Leu Ile Lys Phe Ala Ser Gln Ser Leu Ser Gly
                180                 185                 190

Val Pro Ser Arg Phe Ser Gly Ser Gly Ser Gly Thr Asp Phe Thr Leu
                195                 200                 205

Thr Ile Ser Ser Leu Gln Pro Glu Asp Phe Ala Thr Tyr Tyr Cys Gln
                210                 215                 220

Gln Ser Tyr Ser Thr Pro Ser Thr Phe Gly Pro Gly Thr Lys Val Glu
225                 230                 235                 240

Ile Lys

<210> SEQ ID NO 34
<211> LENGTH: 726
<212> TYPE: DNA
<213> ORGANISM: artificial sequence
<220> FEATURE:
<223> OTHER INFORMATION: C32oN-10 (nuc)

<400> SEQUENCE: 34
gagctgcagc tggtcgagca gtctggagct gcactggtga agcctgggga ctctgtgaag    60
atgtcttgca aagcttctgg ttatccattc actgactata ttgtacactg ggtgaagcag   120
agtcatggaa agagccttga ctggattggt tatattaatc cttacagtgg tgatactaag   180
ttcaatgaaa agttcaagag taaggccacg ttgactgttg acaagtccag cagcacagcc   240
tatatggagt ttagccgatt gacatctgag gattctgcaa tctattactg tgcaagatcg   300
ggtctgatag cagtctactt tgattactgg ggccaaggga ccacggtcac cgtctcctca   360
ggtggtggtg gttctggcgg cggcggctcc ggtggtggtg gttctgagct cgtgctgact   420
cagtctccag actttcagtc tgtgactcca aaggagaaag tcaccatcac ctgccgggcc   480
agtcagagca ttggtagtag cttacactgg taccagcaga accagatca gtctccaaag   540
ctcctcatca agtttgcttc ccagtccctc tcaggggtcc cctcgaggtt cagtggcagt   600
ggatctggga cagatttcac cctcaccatc aatagcctgg aagctgaaga ttttgcaact   660
tactactgtc aacagagtta cagtacccct agtactttcg gccctgggac caaggtggag   720
atcaaa                                                              726

<210> SEQ ID NO 35
<211> LENGTH: 242
<212> TYPE: PRT
<213> ORGANISM: artificial sequence
<220> FEATURE:
<223> OTHER INFORMATION: C32oN-10 (prot)

<400> SEQUENCE: 35

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
                20                  25                  30

Tyr Ile Val His Trp Val Lys Gln Ser His Gly Lys Ser Leu Asp Trp
            35                  40                  45

Ile Gly Tyr Ile Asn Pro Tyr Ser Gly Asp Thr Lys Phe Asn Glu Lys
 50                  55                  60

Phe Lys Ser Lys Ala Thr Leu Thr Val Asp Lys Ser Ser Ser Thr Ala
 65                  70                  75                  80

Tyr Met Glu Phe Ser Arg Leu Thr Ser Glu Asp Ser Ala Ile Tyr Tyr
                 85                  90                  95

Cys Ala Arg Ser Gly Leu Ile Ala Val Tyr Phe Asp Tyr Trp Gly Gln
                100                 105                 110

Gly Thr Thr Val Thr Val Ser Ser Gly Gly Gly Gly Ser Gly Gly Gly
            115                 120                 125

Gly Ser Gly Gly Gly Gly Ser Glu Leu Val Leu Thr Gln Ser Pro Asp
130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Thr Leu
        195                 200                 205

Thr Ile Asn Ser Leu Glu Ala Glu Asp Phe Ala Thr Tyr Tyr Cys Gln
210                 215                 220

Gln Ser Tyr Ser Thr Pro Ser Thr Phe Gly Pro Gly Thr Lys Val Glu
225                 230                 235                 240

Ile Lys

<210> SEQ ID NO 36
<211> LENGTH: 726
<212> TYPE: DNA
<213> ORGANISM: artificial sequence
<220> FEATURE:
<223> OTHER INFORMATION: C32oN-21 (nuc)

<400> SEQUENCE: 36
gagctgcagc tggtcgagca gtctggagct gcactggtga agcctgggga ctctgtgaag    60
atgtcttgca aagcttctgg ttatccattc actgactata ttgtacactg ggtgaagcag   120
agtcatggaa agagccttga ctggattggt tatattaatc cttacagtgg tgatactaag   180
ttcaatgaaa agttcaagag taaggccacg ttgactgttg acaagtccag cagcacagcc   240
tatatggagt ttagccgatt gacatctgag gattctgcaa tctattactg tgcaagatcg   300
ggtctgatag cagtctactt tgattactgg ggccaaggga ccacggtcac cgtctcctca   360
ggtggtggtg gttctggcgg cggcggctcc ggtggtggtg gttctgagct cgtgctgact   420
cagtctcccg gctttcagtc tgtgactcca aaggagaaag tcaccatcac ctgccgggcc   480
agtcagagca ttggtagtag cttacactgg taccagcaga aaccagatca gtctccaaag   540
ctcctcatca aatttgcttc ccagtccatc tcagggtgtcc cctcgaggtt cagtggcact   600
ggatctggga cagatttcac cctcaccatc aatagcctgg aagctgaaga tgctgcaacc   660
tattactgtc agcagagtag tactttacct cccactttg gccaggggac caagctggag   720
atcaaa                                                               726

<210> SEQ ID NO 37
<211> LENGTH: 242

<212> TYPE: PRT
<213> ORGANISM: artificial sequence
<220> FEATURE:
<223> OTHER INFORMATION: C32oN-21 (prot)

<400> SEQUENCE: 37

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Gly
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Lys Pro Asp
                165                 170                 175

Gln Ser Pro Lys Leu Leu Ile Lys Phe Ala Ser Gln Ser Ile Ser Gly
            180                 185                 190

Val Pro Ser Arg Phe Ser Gly Thr Gly Ser Gly Thr Asp Phe Thr Leu
        195                 200                 205

Thr Ile Asn Ser Leu Glu Ala Glu Asp Ala Ala Thr Tyr Tyr Cys Gln
    210                 215                 220

Gln Ser Ser Thr Leu Pro Pro Thr Phe Gly Gln Gly Thr Lys Leu Glu
225                 230                 235                 240

Ile Lys

<210> SEQ ID NO 38
<211> LENGTH: 726
<212> TYPE: DNA
<213> ORGANISM: artificial sequence
<220> FEATURE:
<223> OTHER INFORMATION: C32oN-34 (nuc)

<400> SEQUENCE: 38
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg gttctggcgg cggcggctcc ggtggtggtg gttctgagct cgtgctgact     420
cagtctccag actttcagtc tgtgactcca aaggagagag tcaccatcac ctgccgggcc     480

```
agtcagacca ttggtaataa cttacactgg taccagcaga aaccaggtca gtctccaaag   540
ctcctcatca agtttgcttc ccagtccttc tcagggtcc cctcgaggtt cagtggcagt    600
ggatctggga cagatttcac cctcaccatc aatagcctgg aagctgaaga tgctgcaact   660
tattactgtc aacagagtta cagtaccccg tggacgttcg gccaagggac caaggtggaa   720
atcaaa                                                              726
```

```
<210> SEQ ID NO 39
<211> LENGTH: 242
<212> TYPE: PRT
<213> ORGANISM: artificial sequence
<220> FEATURE:
<223> OTHER INFORMATION: C32oN-34 (prot)

<400> SEQUENCE: 39
```

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Asp
    130                 135                 140

Phe Gln Ser Val Thr Pro Lys Glu Arg Val Thr Ile Thr Cys Arg Ala
145                 150                 155                 160

Ser Gln Thr Ile Gly Asn Asn Leu His Trp Tyr Gln Gln Lys Pro Gly
                165                 170                 175

Gln Ser Pro Lys Leu Leu Ile Lys Phe Ala Ser Gln Ser Phe Ser Gly
            180                 185                 190

Val Pro Ser Arg Phe Ser Gly Ser Gly Ser Gly Thr Asp Phe Thr Leu
        195                 200                 205

Thr Ile Asn Ser Leu Glu Ala Glu Asp Ala Ala Thr Tyr Tyr Cys Gln
    210                 215                 220

Gln Ser Tyr Ser Thr Pro Trp Thr Phe Gly Gln Gly Thr Lys Val Glu
225                 230                 235                 240

Ile Lys

```
<210> SEQ ID NO 40
<211> LENGTH: 726
<212> TYPE: DNA
<213> ORGANISM: artificial sequence
<220> FEATURE:
<223> OTHER INFORMATION: C32oN-46 (nuc)

<400> SEQUENCE: 40
gagctgcagc tggtcgagca gtctggagct gcactggtga agcctgggga ctctgtgaag   60
atgtcttgca aagcttctgg ttatccattc actgactata ttgtacactg ggtgaagcag   120
```

```
agtcatggaa agagccttga ctggattggt tatattaatc cttacagtgg tgatactaag    180
ttcaatgaaa agttcaagag taaggccacg ttgactgttg acaagtccag cagcacagcc    240
tatatggagt ttagccgatt gacatctgag gattctgcaa tctattactg tgcaagatcg    300
ggtctgatag cagtctactt tgattactgg ggccaaggga ccacggtcac cgtctcctca    360
ggtggtggtg gttctggcgg cggcggctcc ggtggtggtg gttctgagct cgtgctgact    420
cagtctccag actttcagtc tgtgactcca aaggagaaag tcaccatcac ctgccgggcc    480
agtcagagta ttggtagtag cttacactgg taccagcaga aaccagatca gtctccaaag    540
ctcctcatca gtttgcttc ccagtccctc tcaggggtcc catcaaggtt cagtggcagt    600
ggatctggga cagatttcac tctcaccatc agcagtctgc aacctgaaga ttttgcaact    660
tactactgtc aacagagtta cagtacccct ccaacgttcg gccaagggac caaggtggaa    720
atcaaa                                                                726
```

```
<210> SEQ ID NO 41
<211> LENGTH: 242
<212> TYPE: PRT
<213> ORGANISM: artificial sequence
<220> FEATURE:
<223> OTHER INFORMATION: C32oN-46 (prot)

<400> SEQUENCE: 41

Glu Leu Gln Leu Val Glu Gln Ser Gly Ala Ala Leu Val Lys Pro Gly
 1               5                  10                  15

Asp Ser Val Lys Met Ser Cys Lys Ala Ser Gly Tyr Pro Phe Thr Asp
                20                  25                  30

Tyr Ile Val His Trp Val Lys Gln Ser His Gly Lys Ser Leu Asp Trp
             35                  40                  45

Ile Gly Tyr Ile Asn Pro Tyr Ser Gly Asp Thr Lys Phe Asn Glu Lys
         50                  55                  60

Phe Lys Ser Lys Ala Thr Leu Thr Val Asp Lys Ser Ser Ser Thr Ala
 65                  70                  75                  80

Tyr Met Glu Phe Ser Arg Leu Ser Glu Asp Ser Ala Ile Tyr Tyr
                 85                  90                  95

Cys Ala Arg Ser Gly Leu Ile Ala Val Tyr Phe Asp Tyr Trp Gly Gln
                100                 105                 110

Gly Thr Thr Val Thr Val Ser Ser Gly Gly Gly Gly Ser Gly Gly Gly
            115                 120                 125

Gly Ser Gly Gly Gly Gly Ser Glu Leu Val Leu Thr Gln Ser Pro Asp
        130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Ser Tyr Ser Thr Pro Pro Thr Phe Gly Gln Gly Thr Lys Val Glu
225                 230                 235                 240

Ile Lys
```

<210> SEQ ID NO 42
<211> LENGTH: 726
<212> TYPE: DNA
<213> ORGANISM: artificial sequence
<220> FEATURE:
<223> OTHER INFORMATION: C32oN-89 (nuc)

<400> SEQUENCE: 42

```
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg gttctggcgg cggcggctcc ggtggtggtg gttctgagct cgtgttgacg     420
cagtctccat cctccctgtc tgcatctgta ggagacagag tcaccatcac ttgccgggca     480
agtcagagca ttagcaggta tttaaattgg tatcaacaaa aaccagggaa accccctaag     540
ctcctgatct tgttgcatc caatttgcaa actggggtcc catcaaggtt cagtggcagt     600
ggatctggga cagatttcac tctcaccatc agcagcctag agcctgaaga ttttgcagtt     660
tattactgtc agcagcgtag caactggccc ctcactttcg gcggagggac caaagtggat     720
atcaaa                                                                726
```

<210> SEQ ID NO 43
<211> LENGTH: 242
<212> TYPE: PRT
<213> ORGANISM: artificial sequence
<220> FEATURE:
<223> OTHER INFORMATION: C32oN-89 (prot)

<400> SEQUENCE: 43

```
Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Glu Leu Val Leu Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Ser Arg Tyr Leu Asn Trp Tyr Gln Gln Lys Pro Gly
                165                 170                 175

Lys Pro Pro Lys Leu Leu Ile Phe Val Ala Ser Asn Leu Gln Thr Gly
```

```
                180             185             190
Val Pro Ser Arg Phe Gly Ser Gly Ser Gly Thr Asp Phe Thr Leu
            195             200             205

Thr Ile Ser Ser Leu Glu Pro Glu Asp Phe Ala Val Tyr Tyr Cys Gln
        210             215             220

Gln Arg Ser Asn Trp Pro Leu Thr Phe Gly Gly Gly Thr Lys Val Asp
225             230             235             240

Ile Lys

<210> SEQ ID NO 44
<211> LENGTH: 726
<212> TYPE: DNA
<213> ORGANISM: artificial sequence
<220> FEATURE:
<223> OTHER INFORMATION: C32oN-92 (nuc)

<400> SEQUENCE: 44
gagctgcagc tggtcgagca gtctggagct gcactggtga agcctgggga ctctgtgaag    60
atgtcttgca aagcttctgg ttatccattc actgactata ttgtacactg ggtgaagcag   120
agtcatggaa agagccttga ctggattggt tatattaatc cttacagtgg tgatactaag   180
ttcaatgaaa agttcaagag taaggccacg ttgactgttg acaagtccag cagcacagcc   240
tatatggagt ttagccgatt gacatctgag gattctgcaa tctattactg tgcaagatcg   300
ggtctgatag cagtctactt tgattactgg ggccaaggga ccacggtcac cgtctcctca   360
ggtggtggtg gttctggcgg cggcggctcc ggtggtggtg gttctgagct cgtgctgact   420
cagtctccag actttcagtc tgtgactcca aaggagaaag tcaccatcac ctgccgggcc   480
agtcagagca ttggtagtag cttacactgg taccagcaga aaccagatca gtctccaaag   540
ctcctcatca gtttgcttc ccagtccctc tcaggggtcc cctcgaggtt cagtggcagt   600
ggatctggga cagatttcgc cctcaccatc aatagcctgg aagctgaaga tgctgcaacc   660
tattactgtc agcagagtag tactttacct cccactttg gccaggggac caagctggag   720
atcaaa                                                               726

<210> SEQ ID NO 45
<211> LENGTH: 242
<212> TYPE: PRT
<213> ORGANISM: artificial sequence
<220> FEATURE:
<223> OTHER INFORMATION: C32oN-92 (prot)

<400> SEQUENCE: 45

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
    50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110
```

```
Gly Thr Thr Val Thr Val Ser Ser Gly Gly Gly Ser Gly Gly
        115                 120                 125

Gly Ser Gly Gly Gly Ser Glu Leu Val Leu Thr Gln Ser Pro Asp
    130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Ala Leu
        195                 200                 205

Thr Ile Asn Ser Leu Glu Ala Glu Asp Ala Ala Thr Tyr Tyr Cys Gln
    210                 215                 220

Gln Ser Ser Thr Leu Pro Pro Thr Phe Gly Gln Gly Thr Lys Leu Glu
225                 230                 235                 240

Ile Lys

<210> SEQ ID NO 46
<211> LENGTH: 726
<212> TYPE: DNA
<213> ORGANISM: artificial sequence
<220> FEATURE:
<223> OTHER INFORMATION: C33oN-32 (nuc)

<400> SEQUENCE: 46
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg ttctggcgg cggcggctcc ggtggtggtg ttctgagct cgtgctgact     420 cagtctccag agtttcagtc tgtggctcca aggagaaag tcaccatcac ctgccgggcc     480
agtcagagca ttggtagtag cttacactgg taccagcaga aaccagatca gtctccaaag     540
ctcctcatca gtttgcttc ccagtccttc tcaggggtcc cctcgaggtt cggtggcagt     600
ggatctggga caatttcac cctcaccatc aatagcctgg aagctgaaga tgctgcaacc     660
tattactgtc agcagagtag taccttacct cccactttg gccagggac caagctggag     720 atcaaa                                                                 726

<210> SEQ ID NO 47
<211> LENGTH: 242
<212> TYPE: PRT
<213> ORGANISM: artificial sequence
<220> FEATURE:
<223> OTHER INFORMATION: C33oN-32 (prot)

<400> SEQUENCE: 47

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45
```

Ile Gly Tyr Ile Asn Pro Tyr Ser Gly Asp Thr Lys Phe Asn Glu Lys
 50                  55                  60

Phe Lys Ser Lys Ala Thr Leu Thr Val Asp Lys Ser Ser Ser Thr Ala
 65                  70                  75                  80

Tyr Met Glu Phe Ser Arg Leu Thr Ser Glu Asp Ser Ala Ile Tyr Tyr
             85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Ser Gly Gly Gly
            115                 120                 125

Gly Ser Gly Gly Gly Ser Glu Leu Val Leu Thr Gln Ser Pro Glu
        130                 135                 140

Phe Gln Ser Val Ala Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
            165                 170                 175

Gln Ser Pro Lys Leu Leu Ile Lys Phe Ala Ser Gln Ser Phe Ser Gly
            180                 185                 190

Val Pro Ser Arg Phe Gly Ser Gly Ser Gly Thr Asn Phe Thr Leu
        195                 200                 205

Thr Ile Asn Ser Leu Glu Ala Glu Asp Ala Ala Thr Tyr Tyr Cys Gln
210                 215                 220

Gln Ser Ser Thr Leu Pro Pro Thr Phe Gly Gln Gly Thr Lys Leu Glu
225                 230                 235                 240

Ile Lys

<210> SEQ ID NO 48
<211> LENGTH: 726
<212> TYPE: DNA
<213> ORGANISM: artificial sequence
<220> FEATURE:
<223> OTHER INFORMATION: C33oN-33 (nuc)

<400> SEQUENCE: 48
gagctgcagc tggtcgagca gtctggagct gcactggtga agcctgggga ctctgtgaag    60
atgtcttgca aagcttctgg ttatccattc actgactata ttgtacactg ggtgaagcag   120
agtcatggaa agagccttga ctggattggt tatattaatc cttacagtgg tgatactaag   180
ttcaatgaaa agttcaagag taaggccacg ttgactgttg acaagtccag cagcacagcc   240
tatatggagt ttagccgatt gacatctgag gattctgcaa tctattactg tgcaagatcg   300
ggtctgatag cagtctactt tgattactgg ggccaaggga ccacggtcac cgtctcctca   360
ggtggtggtg gttctggcgg cggcggctcc ggtggtggtg gttctgagct cgtgctgact   420
cagtctccag actttcagtc tgtgactcca aaggagaaag tcaccatcac ctgccgggcc   480
agtcagagca ttggtagtag cttacactgg taccagcaga accagatcag tctccaaag    540
ctcctcatca gtttgcttc ccagtccctc tcagggtcc cctcgaggtt cagtggcagt    600
ggatctggga cagatttcac cctcaccatc aatagcctgg aagctgaaga tgctgcaact   660
tactactgtc aacagagtta cagtaccccct agtactttcg gccctgggac caaggtggag   720
atcaaa                                                              726

<210> SEQ ID NO 49
<211> LENGTH: 242
<212> TYPE: PRT
<213> ORGANISM: artificial sequence

```
<220> FEATURE:
<223> OTHER INFORMATION: C33oN-33 (prot)

<400> SEQUENCE: 49

Glu Leu Gln Leu Val Glu Gln Ser Gly Ala Ala Leu Val Lys Pro Gly
1               5                   10                  15

Asp Ser Val Lys Met Ser Cys Lys Ala Ser Gly Tyr Pro Phe Thr Asp
            20                  25                  30

Tyr Ile Val His Trp Val Lys Gln Ser His Gly Lys Ser Leu Asp Trp
        35                  40                  45

Ile Gly Tyr Ile Asn Pro Tyr Ser Gly Asp Thr Lys Phe Asn Glu Lys
50                  55                  60

Phe Lys Ser Lys Ala Thr Leu Thr Val Asp Lys Ser Ser Ser Thr Ala
65                  70                  75                  80

Tyr Met Glu Phe Ser Arg Leu Thr Ser Glu Asp Ser Ala Ile Tyr Tyr
                85                  90                  95

Cys Ala Arg Ser Gly Leu Ile Ala Val Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Ser Glu Leu Val Leu Thr Gln Ser Pro Asp
130                 135                 140

Phe Gln Ser Val Thr Pro Lys Glu Lys Val Thr Ile Thr Cys Arg Ala
145                 150                 155                 160

Ser Gln Ser Ile Gly Ser Ser Leu His Trp Tyr Gln Gln Lys Pro Asp
                165                 170                 175

Gln Ser Pro Lys Leu Leu Ile Lys Phe Ala Ser Gln Ser Leu Ser Gly
            180                 185                 190

Val Pro Ser Arg Phe Ser Gly Ser Gly Ser Gly Thr Asp Phe Thr Leu
        195                 200                 205

Thr Ile Asn Ser Leu Glu Ala Glu Asp Ala Ala Thr Tyr Tyr Cys Gln
210                 215                 220

Gln Ser Tyr Ser Thr Pro Ser Thr Phe Gly Pro Gly Thr Lys Val Glu
225                 230                 235                 240

Ile Lys

<210> SEQ ID NO 50
<211> LENGTH: 726
<212> TYPE: DNA
<213> ORGANISM: artificial sequence
<220> FEATURE:
<223> OTHER INFORMATION: C33oN-49 (nuc)

<400> SEQUENCE: 50
gagctgcagc tggtcgagca gtctggagct gcactggtga agcctgggga ctctgtgaag      60
atgtcttgca aagcttctgg ttatccattc actgactata ttgtacactg ggtgaagcag     120
agtcatggaa agagccttga ctggattggt tatattaatc cttacagtgg tgatactaag     180
ttcaatgaaa agttcaagag taaggccacg ttgactgttg acaagtccag cagcacagcc     240
tatatggagt ttagccgatt gacatctgag gattctgcaa tctattactg tgcaagatcg     300
ggtctgatag cagtctactt tgattactgg ggccaaggga ccacggtcac cgtctcctca     360
ggtggtggtg gttctggcgg cggcggctcc ggtggtggtg gttctgagct cgtgctgact     420
cagtctccag actttcagtc tgtgactcca aaggagaaag tcaccatcac ctgccgggcc     480
agtcagagca ttggtagtag cttacactgg taccagcaga aaccagatca gtctccaaag     540
```

-continued

```
ctcctcatca agtttgcttc ccagtccttc tcaggggtcc cctcgaggtt cagtggcagt    600
ggatctggga cagatttcac cctcaccatc aatagcctgg aagctgaaga tgctgcaacg    660
tattactgtc aacagagtta cagtaccccg tggacgttcg gccaagggac caagctggag    720
atcaaa                                                               726
```

<210> SEQ ID NO 51
<211> LENGTH: 242
<212> TYPE: PRT
<213> ORGANISM: artificial sequence
<220> FEATURE:
<223> OTHER INFORMATION: C33oN-49 (prot)

<400> SEQUENCE: 51

| Glu | Leu | Gln | Leu | Val | Glu | Gln | Ser | Gly | Ala | Ala | Leu | Val | Lys | Pro | Gly |
| 1 | | | | 5 | | | | | 10 | | | | | 15 | |

| Asp | Ser | Val | Lys | Met | Ser | Cys | Lys | Ala | Ser | Gly | Tyr | Pro | Phe | Thr | Asp |
| | | | 20 | | | | | 25 | | | | | 30 | | |

| Tyr | Ile | Val | His | Trp | Val | Lys | Gln | Ser | His | Gly | Lys | Ser | Leu | Asp | Trp |
| | | 35 | | | | | 40 | | | | | 45 | | | |

| Ile | Gly | Tyr | Ile | Asn | Pro | Tyr | Ser | Gly | Asp | Thr | Lys | Phe | Asn | Glu | Lys |
| | 50 | | | | | 55 | | | | | 60 | | | | |

| Phe | Lys | Ser | Lys | Ala | Thr | Leu | Thr | Val | Asp | Lys | Ser | Ser | Ser | Thr | Ala |
| 65 | | | | | 70 | | | | | 75 | | | | | 80 |

| Tyr | Met | Glu | Phe | Ser | Arg | Leu | Thr | Ser | Glu | Asp | Ser | Ala | Ile | Tyr | Tyr |
| | | | | 85 | | | | | 90 | | | | | 95 | |

| Cys | Ala | Arg | Ser | Gly | Leu | Ile | Ala | Val | Tyr | Phe | Asp | Tyr | Trp | Gly | Gln |
| | | | 100 | | | | | 105 | | | | | 110 | | |

| Gly | Thr | Thr | Val | Thr | Val | Ser | Ser | Gly | Gly | Gly | Ser | Gly | Gly | Gly |
| | | 115 | | | | | 120 | | | | | 125 | | | |

| Gly | Ser | Gly | Gly | Gly | Gly | Ser | Glu | Leu | Val | Leu | Thr | Gln | Ser | Pro | Asp |
| | 130 | | | | | 135 | | | | | 140 | | | | |

| Phe | Gln | Ser | Val | Thr | Pro | Lys | Glu | Lys | Val | Thr | Ile | Thr | Cys | Arg | Ala |
| 145 | | | | | 150 | | | | | 155 | | | | | 160 |

| Ser | Gln | Ser | Ile | Gly | Ser | Ser | Leu | His | Trp | Tyr | Gln | Gln | Lys | Pro | Asp |
| | | | | 165 | | | | | 170 | | | | | 175 | |

| Gln | Ser | Pro | Lys | Leu | Leu | Ile | Lys | Phe | Ala | Ser | Gln | Ser | Phe | Ser | Gly |
| | | | 180 | | | | | 185 | | | | | 190 | | |

| Val | Pro | Ser | Arg | Phe | Ser | Gly | Ser | Gly | Ser | Gly | Thr | Asp | Phe | Thr | Leu |
| | | 195 | | | | | 200 | | | | | 205 | | | |

| Thr | Ile | Asn | Ser | Leu | Glu | Ala | Glu | Asp | Ala | Ala | Thr | Tyr | Tyr | Cys | Gln |
| | 210 | | | | | 215 | | | | | 220 | | | | |

| Gln | Ser | Tyr | Ser | Thr | Pro | Trp | Thr | Phe | Gly | Gln | Gly | Thr | Lys | Leu | Glu |
| 225 | | | | | 230 | | | | | 235 | | | | | 240 |

| Ile | Lys |
| | |

<210> SEQ ID NO 52
<211> LENGTH: 35
<212> TYPE: DNA
<213> ORGANISM: Artificial Sequence
<220> FEATURE:
<223> OTHER INFORMATION: Synthetic primer

<400> SEQUENCE: 52

```
tttgcggccg cgtcgactaa cactcattcc tgttg                                35
```

<210> SEQ ID NO 53
<211> LENGTH: 40

```
<212> TYPE: DNA
<213> ORGANISM: Artificial Sequence
<220> FEATURE:
<223> OTHER INFORMATION: Synthetic primer

<400> SEQUENCE: 53
gccgaattcc accatgragt cacakacyca ggtcttyrta                    40

<210> SEQ ID NO 54
<211> LENGTH: 39
<212> TYPE: DNA
<213> ORGANISM: Artificial Sequence
<220> FEATURE:
<223> OTHER INFORMATION: Synthetic primer

<400> SEQUENCE: 54
gccgaattcc accatggrat gsagctgkgt matsctctt                     39

<210> SEQ ID NO 55
<211> LENGTH: 29
<212> TYPE: DNA
<213> ORGANISM: Artificial Sequence
<220> FEATURE:
<223> OTHER INFORMATION: Synthetic primer

<400> SEQUENCE: 55
cacaccgctg gacagggctc cagagttcc                                29

<210> SEQ ID NO 56
<211> LENGTH: 30
<212> TYPE: DNA
<213> ORGANISM: Artificial Sequence
<220> FEATURE:
<223> OTHER INFORMATION: Synthetic primer

<400> SEQUENCE: 56
tgggagctct gacatcgtgc tgactcagtc                               30

<210> SEQ ID NO 57
<211> LENGTH: 31
<212> TYPE: DNA
<213> ORGANISM: Artificial Sequence
<220> FEATURE:
<223> OTHER INFORMATION: Synthetic primer

<400> SEQUENCE: 57
attgcggccg ctttcagttc cagcttggtc c                             31

<210> SEQ ID NO 58
<211> LENGTH: 27
<212> TYPE: DNA
<213> ORGANISM: Artificial Sequence
<220> FEATURE:
<223> OTHER INFORMATION: Synthetic primer

<400> SEQUENCE: 58
aaagtcgaca aactgctgca gtctggg                                  27

<210> SEQ ID NO 59
<211> LENGTH: 28
<212> TYPE: DNA
<213> ORGANISM: Artificial Sequence
<220> FEATURE:
<223> OTHER INFORMATION: Synthetic primer

<400> SEQUENCE: 59
atttccggat gaggagactg tgaccatg                                 28
```

<210> SEQ ID NO 60
<211> LENGTH: 27
<212> TYPE: DNA
<213> ORGANISM: Artificial Sequence
<220> FEATURE:
<223> OTHER INFORMATION: Synthetic primer

<400> SEQUENCE: 60
gaggttcagc tcgagcagtc tggagct                                      27

<210> SEQ ID NO 61
<211> LENGTH: 34
<212> TYPE: DNA
<213> ORGANISM: Artificial Sequence
<220> FEATURE:
<223> OTHER INFORMATION: Synthetic primer

<400> SEQUENCE: 61
tgaggagacg gtgaccgtgg tcccttggcc ccag                              34

<210> SEQ ID NO 62
<211> LENGTH: 32
<212> TYPE: DNA
<213> ORGANISM: Artificial Sequence
<220> FEATURE:
<223> OTHER INFORMATION: Synthetic primer

<400> SEQUENCE: 62
ccagttccga gctcgtgctc acccagtctc ca                                32

<210> SEQ ID NO 63
<211> LENGTH: 39
<212> TYPE: DNA
<213> ORGANISM: Artificial Sequence
<220> FEATURE:
<223> OTHER INFORMATION: Synthetic primer

<400> SEQUENCE: 63
tggtgcacta gtcgtacgtt tgatctcaag cttggtccc                         39

<210> SEQ ID NO 64
<211> LENGTH: 38
<212> TYPE: DNA
<213> ORGANISM: Artificial Sequence
<220> FEATURE:
<223> OTHER INFORMATION: Synthetic primer

<400> SEQUENCE: 64
gagccgcacg agcccgagct ccagatgacc cagtctcc                          38

<210> SEQ ID NO 65
<211> LENGTH: 38
<212> TYPE: DNA
<213> ORGANISM: Artificial Sequence
<220> FEATURE:
<223> OTHER INFORMATION: Synthetic primer

<400> SEQUENCE: 65
gagccgcacg agcccgagct cgtgatgacy cagtctcc                          38

<210> SEQ ID NO 66
<211> LENGTH: 38
<212> TYPE: DNA
<213> ORGANISM: Artificial Sequence
<220> FEATURE:
<223> OTHER INFORMATION: Synthetic primer

<400> SEQUENCE: 66
gagccgcacg agcccgagct cgtgwtgacr cagtctcc                       38

<210> SEQ ID NO 67
<211> LENGTH: 38
<212> TYPE: DNA
<213> ORGANISM: Artificial Sequence
<220> FEATURE:
<223> OTHER INFORMATION: Synthetic primer

<400> SEQUENCE: 67
gagccgcacg agcccgagct cacactcacg cagtctcc                       38

<210> SEQ ID NO 68
<211> LENGTH: 38
<212> TYPE: DNA
<213> ORGANISM: Artificial Sequence
<220> FEATURE:
<223> OTHER INFORMATION: Synthetic primer

<400> SEQUENCE: 68
gagccgcacg agcccgagct cgtgctgact cagtctcc                       38

<210> SEQ ID NO 69
<211> LENGTH: 47
<212> TYPE: DNA
<213> ORGANISM: Artificial Sequence
<220> FEATURE:
<223> OTHER INFORMATION: Synthetic primer

<400> SEQUENCE: 69
gacgacacta gttgcagcca ccgtacgttt gatttccacc ttggtcc             47

<210> SEQ ID NO 70
<211> LENGTH: 47
<212> TYPE: DNA
<213> ORGANISM: Artificial Sequence
<220> FEATURE:
<223> OTHER INFORMATION: Synthetic primer

<400> SEQUENCE: 70
gacgacacta gttgcagcca ccgtacgttt gatctccasc ttggtcc             47

<210> SEQ ID NO 71
<211> LENGTH: 47
<212> TYPE: DNA
<213> ORGANISM: Artificial Sequence
<220> FEATURE:
<223> OTHER INFORMATION: Synthetic primer

<400> SEQUENCE: 71
gacgacacta gttgcagcca ccgtacgttt gatatccact ttggtcc             47

<210> SEQ ID NO 72
<211> LENGTH: 47
<212> TYPE: DNA
<213> ORGANISM: Artificial Sequence
<220> FEATURE:
<223> OTHER INFORMATION: Synthetic primer

<400> SEQUENCE: 72
gacgacacta gttgcagcca ccgtacgttt aatctccagt cgtgtcc             47

<210> SEQ ID NO 73
<211> LENGTH: 27

```
<212> TYPE: DNA
<213> ORGANISM: Artificial Sequence
<220> FEATURE:
<223> OTHER INFORMATION: Synthetic primer

<400> SEQUENCE: 73
gaggttcagc tcgagcagtc tggagct                                              27

<210> SEQ ID NO 74
<211> LENGTH: 34
<212> TYPE: DNA
<213> ORGANISM: Artificial Sequence
<220> FEATURE:
<223> OTHER INFORMATION: Synthetic primer

<400> SEQUENCE: 74
tgaggagacg gtgaccgtgg tcccttggcc ccag                                      34

<210> SEQ ID NO 75
<211> LENGTH: 10
<212> TYPE: PRT
<213> ORGANISM: Artificial Sequence
<220> FEATURE:
<223> OTHER INFORMATION: Synthetic peptide

<400> SEQUENCE: 75

Thr Gly Asp Tyr Lys Asp Asp Asp Asp Lys
1               5                   10

<210> SEQ ID NO 76
<211> LENGTH: 22
<212> TYPE: DNA
<213> ORGANISM: Artificial Sequence
<220> FEATURE:
<223> OTHER INFORMATION: Synthetic primer

<400> SEQUENCE: 76
aggtgcagct gctcgagtct gg                                                   22

<210> SEQ ID NO 77
<211> LENGTH: 23
<212> TYPE: DNA
<213> ORGANISM: Artificial Sequence
<220> FEATURE:
<223> OTHER INFORMATION: Synthetic primer

<400> SEQUENCE: 77
cagrtcacct tgctcgagtc tgg                                                  23

<210> SEQ ID NO 78
<211> LENGTH: 23
<212> TYPE: DNA
<213> ORGANISM: Artificial Sequence
<220> FEATURE:
<223> OTHER INFORMATION: Synthetic primer

<400> SEQUENCE: 78
caggtgcagc tgctcgagtc ggg                                                  23

<210> SEQ ID NO 79
<211> LENGTH: 23
<212> TYPE: DNA
<213> ORGANISM: Artificial Sequence
<220> FEATURE:
<223> OTHER INFORMATION: Synthetic primer

<400> SEQUENCE: 79
```

```
caggtgcagc tactcgagtg ggg                                          23

<210> SEQ ID NO 80
<211> LENGTH: 23
<212> TYPE: DNA
<213> ORGANISM: Artificial Sequence
<220> FEATURE:
<223> OTHER INFORMATION: Synthetic primer

<400> SEQUENCE: 80
caggtacagc tgctcgagtc agg                                          23

<210> SEQ ID NO 81
<211> LENGTH: 17
<212> TYPE: DNA
<213> ORGANISM: Artificial Sequence
<220> FEATURE:
<223> OTHER INFORMATION: Synthetic primer

<400> SEQUENCE: 81
ctgaggagac ggtgacc                                                 17

<210> SEQ ID NO 82
<211> LENGTH: 17
<212> TYPE: DNA
<213> ORGANISM: Artificial Sequence
<220> FEATURE:
<223> OTHER INFORMATION: Synthetic primer

<400> SEQUENCE: 82
ctgaagagac ggtgacc                                                 17

<210> SEQ ID NO 83
<211> LENGTH: 51
<212> TYPE: DNA
<213> ORGANISM: Artificial Sequence
<220> FEATURE:
<223> OTHER INFORMATION: Synthetic primer

<400> SEQUENCE: 83
gtaatcaaag tagactgcta tcagacccga tctygcacag taatacacgg c           51

<210> SEQ ID NO 84
<211> LENGTH: 51
<212> TYPE: DNA
<213> ORGANISM: Artificial Sequence
<220> FEATURE:
<223> OTHER INFORMATION: Synthetic primer

<400> SEQUENCE: 84
gtaatcaaag tagactgcta tcagacccga tctygcacag taatacayrg c           51

<210> SEQ ID NO 85
<211> LENGTH: 51
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (34)..(34)
<223> OTHER INFORMATION: n is a, c, g, or t

<400> SEQUENCE: 85
gtaatcaaag tagactgcta tcagacccga tctngyacag taatacacrg c           51

<210> SEQ ID NO 86
```

```
<211> LENGTH: 51
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (34)..(34)
<223> OTHER INFORMATION: n is a, c, g, or t

<400> SEQUENCE: 86
gtaatcaaag tagactgcta tcagacccga tctngcacag taatacaarg c          51

<210> SEQ ID NO 87
<211> LENGTH: 51
<212> TYPE: DNA
<213> ORGANISM: Artificial Sequence
<220> FEATURE:
<223> OTHER INFORMATION: Synthetic primer

<400> SEQUENCE: 87
gtaatcaaag tagactgcta tcagacccga tctsgcacag taatacacrg c          51

<210> SEQ ID NO 88
<211> LENGTH: 48
<212> TYPE: DNA
<213> ORGANISM: Artificial Sequence
<220> FEATURE:
<223> OTHER INFORMATION: Synthetic primer

<400> SEQUENCE: 88
agagacggtg accattgtcc cttggcccca gtaatcaaag tagactgc              48
```